(12) United States Patent
Hanson et al.

(10) Patent No.: US 9,511,129 B2
(45) Date of Patent: Dec. 6, 2016

(54) FACULTATIVELY ATTENUATED BACTERIAL SPECIES AND METHODS OF PREPARATION AND USE THEREOF

(71) Applicant: ADURO BIOTECH, Berkeley, CA (US)

(72) Inventors: William G. Hanson, Walnut Creek, CA (US); Justin Skoble, Berkeley, CA (US); Peter M. Lauer, Albany, CA (US)

(73) Assignee: ADURO BIOTECH, INC., Berkeley, CA (US)

( * ) Notice: Subject to any disclaimer, the term of this patent is extended or adjusted under 35 U.S.C. 154(b) by 0 days.

(21) Appl. No.: 14/073,737

(22) Filed: Nov. 6, 2013

(65) Prior Publication Data

US 2014/0127816 A1 May 8, 2014

Related U.S. Application Data

(60) Provisional application No. 61/723,234, filed on Nov. 6, 2012.

(51) Int. Cl.
*A61K 39/02* (2006.01)
*A61K 39/00* (2006.01)

(52) U.S. Cl.
CPC ........... *A61K 39/02* (2013.01); *A61K 39/0208* (2013.01); *A61K 2039/522* (2013.01); *C12N 2800/30* (2013.01)

(58) Field of Classification Search
None
See application file for complete search history.

(56) References Cited

U.S. PATENT DOCUMENTS

| | | | |
|---|---|---|---|
| 5,767,063 A | 6/1998 | Lee et al. | |
| 5,830,702 A | 11/1998 | Portnoy et al. | |
| 5,888,530 A | 3/1999 | Netti et al. | |
| 6,051,237 A | 4/2000 | Paterson | |
| 6,090,611 A | 7/2000 | Covacci et al. | |
| 6,099,848 A | 8/2000 | Frankel et al. | |
| 6,379,943 B1 | 4/2002 | Graham et al. | |
| 7,790,694 B2 * | 9/2010 | Geller et al. | 514/44 A |
| 8,580,939 B2 | 11/2013 | Dubensky, Jr. et al. | |
| 2002/0150588 A1 | 10/2002 | Allison et al. | |
| 2003/0203472 A1 * | 10/2003 | Portnoy et al. | 435/252.3 |
| 2004/0013690 A1 | 1/2004 | Portnoy et al. | |
| 2005/0048081 A1 | 3/2005 | Frankel et al. | |
| 2005/0281783 A1 | 12/2005 | Kinch et al. | |
| 2007/0135333 A1 | 6/2007 | Geller et al. | |
| 2012/0121643 A1 | 5/2012 | Dubensky, Jr. et al. | |
| 2012/0321662 A1 | 12/2012 | Portnoy et al. | |

FOREIGN PATENT DOCUMENTS

| | | |
|---|---|---|
| EP | 1483367 B1 | 5/2010 |
| WO | 9614087 A1 | 5/1996 |
| WO | 9925376 A1 | 5/1999 |
| WO | 2004006837 A2 | 1/2004 |
| WO | 2007103225 A2 | 9/2007 |
| WO | 2007117371 A2 | 10/2007 |
| WO | 2009143085 A1 | 11/2009 |
| WO | 2012068360 A1 | 5/2012 |

OTHER PUBLICATIONS

GenBank ID AJ012255.1 Apr. 15, 2005, dlt operon Listeria Monocytogenes.*
Weaver et al., Venezuelan Equine Encephalitis. Annu Rev Entomol. 2004;49:141-174.
Weiskirch et al., Listeria monocytogenes: a potent vaccine vector for neoplastic and infectious disease. Immunol Rev. Aug. 1997;158:159-169.
Wells et al., Swine Influenza Virus Infections. Transmission From Ill Pigs to Humans at a Wisconsin Agricultural Fair and Subsequent Probable Person-To-Person Transmission. JAMA. Jan. 23-30, 1991;265(4):478-481.
Wentworth et al., An Influenza A (HINI) Virus, Closely Related to Swine Influenza Virus, Responsible for a Fatal Case of Human Influenza. J Virol. Apr. 1994;68(4):2051-2058.
Wong and Freitag, A Novel Mutation within the Central Listeria monocytogenes Regulator PrfA That Results in Constitutive Expression of Virulence Gene Products. J Bacteriol. Sep. 2004;186(18):6265-6276.
Woycechowsky and Raines, Native Disulfide Bond Formation in Proteins. Curr Opin Chem Biol. Oct. 2000;4(5):533-539.
Zaremba, Identification of an Enhancer Agonist Cytotoxic T Lymphocyte Peptide from Human Carcinoembryonic Antigen. Cancer Res. Oct. 15, 1997;57(20):4570-4577.
Zeier et al., New Ecological Aspects of Hantavirus Infection: A Change of a Paradigm and a Challenge of Prevention—A Review. Virus Genes. Mar. 2005;30(2):157-180.
Zhao et al., Pathogenicity and Immunogenicity of a Vaccine Strain of Listeria monocytogenes That Relies on a Suicide Plasmid to Supply an Essential Gene Product. Infect Immun. Sep. 2005;73(9):5789-5798.
Zimmerman et al., Expression of annexin II in conventional renal cell carcinoma is correlated with Fuhrman grade and clinical outcome. Virchows Arch. Oct. 2004;445(4):368-374.
Ziyaeyan et al., The Seroprevalence of Parvovirus BI9 Infection among To-Be-Married Girls, Pregnant Women, and Their Neonates in Shi raz, Iran. Jpn J Infect Dis. Apr. 2005;58(2):95-97.

(Continued)

*Primary Examiner* — Oluwatosin Ogunbiyi
(74) *Attorney, Agent, or Firm* — Acuity Law Group, P.C.; Michael A. Whittaker

(57) ABSTRACT

The present invention provides facultatively attenuated bacterial species and methods of preparation and use thereof. The term "facultatively attenuated" as used herein refers to a bacterium which comprises a set of defined recombinant modifications which have substantially no effect on the ability of the bacterium to grow by multiplication when the bacterium is outside of its host organism, but which result in deletion of one or more genes essential for multiplication of the bacterium when the bacterium is introduced into its host organism, for example within host cells of a vaccinate recipient. These recombinant modifications take advantage of regulatory sequences which preferentially induce expression of genes within the mammalian host.

21 Claims, 11 Drawing Sheets

(56) References Cited

OTHER PUBLICATIONS

Muminova et al., Characterization of human mesothelin transcripts in ovarian and pancreatic cancer. BMC Cancer. May 12, 2004;4:19.
Munson and Rodbard, Ligand: A Versatile Computerized Approach for Characterization of Ligand-Binding Systems. Anal Biochem. Sep. 1, 1980;107(1):220-239.
Nair et al., Induction of cytotoxic T cell responses and tumor immunity against unrelated tumors using telomerase reverse transcriptase RNA transfected dendritic cells. Nat Med. Sep. 2000;6(9):1011-1017.
Nakatsura et al., Cellular and humoral immune responses to a human pancreatic cancer antigen, coactosin-like protein, originally defined by the SEREX method. Eur J Immunol. Mar. 2002;32(3):826-836.
Nakatsura et al., Glypican-3, overexpressed specifically in human hepatocellular carcinoma, is a novel tumor marker. Biochem Biophys Res Commun. Jun. 20, 2003;306(1):16-25.
Nakatsura et al., Identification of Glypican-3 as a Novel Tumor Marker for Melanoma. Clin Cancer Res. Oct. 1, 2004;10(19):6612-6621.
Neumann et al., Identification of an HLA-DR-Restricted Peptide Epitope with a Promiscuous Binding Pattern Derived from the Cancer Testis Antigen HOM-MEL-40/SSX2. Int J Cancer. Nov. 20, 2004;112(4):661-668.
Nicoletto et al., BRCA-1 and BRCA-2 mutations as prognostic factors in clinical practice and genetic counselling. Cancer Treat Rev. Oct. 2001;27(5):295-304.
Nunes-Duby et al., Similarities and differences among 105 members of the Int family of site-specific recombinases. Nucleic Acids Res. Jan. 15, 1998;26(2):391-406.
Oberste et al., Evidence for Frequent Recombination within Species Human Enterovirus B Based on Complete Genomic Sequences of All Thirty-Seven Serotypes. J Virol. Jan. 2004;78(2):855-867.
Oberthuer et al., The Tumor-Associated Antigen PRAME is Universally Expressed in High-Stage Neuroblastoma and Associated with Poor Outcome. Clin Cancer Res. Jul. 1, 2004;10(13):4307-4313.
Oliveira-Perreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.
O'Riordan et al., Listeria Intracellular Growth and Virulence Require Host-Derived Lipoic Acid. Science. Oct. 17, 2003;302(5644):462-464.
Orvell et al., Antigenic relationships between six genotypes of the small hydrophobic protein gene of mumps virus. J Gen Virol. Oct. 2002;83(Pt 10):2489-2496.
Otte et al., MAGE—A Gene Expression Pattern in Primary Breast Cancer. Cancer Res. Sep. 15, 2001;61(18):6682-6687.
Oyston and Quarry, Tularemia vaccine: past, present and future. Antonie Van Leeuwenhoek. May 2005;87(4):277-281.
Padilla et al., Imaging of the Varicella Zoster Virion in the Viral Highways: Comparison With Herpes Simplex Viruses 1 and 2, Cytomegalovirus, Pseudorabies Virus, and Human Herpes Viruses 6 and 7. J Med Virol. 2003;70 Suppl 1: S103-S110.
Patel et al., Development of a simple restriction fragment length polymorphism assay for subtyping of coxsackie B viruses. J Virol Methods. Sep. 15, 2004;120(2):167-172.
Peh et al., Frequent presence of subtype A virus in Epstein-Barr virus-associated malignancies. Pathology. Oct. 2002; 34(5):446-450.
Pisarev et al., Full-Length Dominant-Negative Survivin for Cancer Immunotherapy. Clin Cancer Res. Dec. 15, 2003;9(17):6523-6533.
Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. Nov. 2004;11(6):1008-1015.
Portnoy et al., Role of Hemolysin for the Intracellular Growth of Listeria Monocytogenes. J Exp Med. Apr. 1, 1988;167(4):1459-1471.
Portnoy et al., The cell biology of Listeria monocytogenes infection: the intersection of bacterial pathogenesis and cell-mediated immunity. J Cell Biol. Aug. 5, 2002;158(3):409-414.
Ramsay et al., DNA vaccination against virus infection and enhancement of antiviral immunity following consecutive immunization with DNA and viral vectors. Immunol Cell Biol. Aug. 1997;75(4):382-388.
Renkvist et al., A listing of human tumor antigens recognized by T cells. Cancer Immunol Immunother. Mar. 2001;50(1):3-15.
Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.
Rezig et al., Molecular Characterization of Coxsackievirus B5 Isolates. J Med Virol. Feb. 2004;72(2):268-274.
Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26(3):817-824.
Ripio et al., A Gly145Ser Substitution in the Transcriptional Activator PrfA Causes Constitutive Overexpression of Virulence Factors in Listeria monocytogenes. J Bacteriol. Mar. 1997;179(5):1533-1540.
Roden and Wu, Preventative and therapeutic vaccines for cervical cancer. Expert Rev Vaccines. Aug. 2003;2(4):495-516.
Roner et al., Identification of signals required for the insertion of heterologous genome segments into the reovirus genome. Proc Natl Acad Sci USA. Dec. 9, 1995;92(26):12362-12366.
Rozinov and Nolan, Evolution of peptides that modulate the spectral qualities of bound, small-molecule fluorophores. Chem Biol. Dec. 1998;5(12):713-728.
Salazar-Onfray et al., Synthetic Peptides Derived from the Melanocyte-Stimulating Hormone Receptor MC1R Can Stimulate HLA-A2-Restricted Cytotoxic T Lymphocytes That Recognize Naturally Processed Peptides on Human Melanoma Cells. Cancer Res. Oct. 1, 1997;57(19):4348-4355.
Santin et al., The serine protease stratum corneum chymotryptic enzyme (kallikrein 7) is highly overexpressed in squamous cervical cancer cells. Gynecol Oncol. Aug. 2004;94(2):283-288.
Sarcevic et al., Expression of Cancer/Testis Tumor Associated Antigens in Cervical Squamous Cell Carcinoma. Oncology. 2003;64(4):443-449.
Sarobe et al., Carcinoembryonic Antigen as a Target to Induce Anti-Tumor Immune Responses. Curr Cancer Drug Targets. Aug. 2004;4(5):443-454.
Sasaki et al., SAGE mRNA expression in advanced-stage lung cancers. Eur J Surg Oncol. Dec. 2003;29(10):900-903.
Sasatomi et al., Expression of Tumor Rejection Antigens in Colorectal Carcinomas. Cancer. Mar. 15, 2002;94(6):1636-1641.
Scanlan et al., Antigens Recognized by Autologous Antibody in Patients with Renal-Cell Carcinoma. Int J Cancer. Nov. 12, 1999;83(4):456-464.
Scanlan et al., Cancer-related Serological Recognition of Human Colon Cancer: Identification of Potential Diagnostic and Immunotherapeutic Targets. Cancer Res. Jul. 15, 2002;62(14):4041-4047.
Scanlan et al., Expression of cancer-testis antigens in lung cancer: definition of bromodomain testis-specific gene (BRDT) as a new CT gene, CT9. Cancer Lett. Mar. 31, 2000;150(2):155-164.
Scanlan et al., Humoral immunity to human breast cancer: antigen definition and quantitative analysis of mRNA expression. Cancer Immun. Mar. 30, 2001;1:4 (17 pp).
Scanlan et al., The cancer/testis genes: Review, standardization, and commentary. Cancer Immun. Jan. 23, 2004;4:1 (15 pp).
Scarcella et al., Expression of MAGE and GAGE in High-Grade Brain Tumors: A Potential Target for Specific Immunotherapy and Diagnostic Markers. Clin Cancer Res. Feb. 1999;5(2):335-341.
Schmittgen et al., Expression of Prostate Specific Membrane Antigen and Three Alternatively Spliced Variants of PSMA in Prostate Cancer Patients. Int J Cancer. Nov. 1, 2003;107(2):323-329.

(56) References Cited

OTHER PUBLICATIONS

Schwartz et al., Novel Targeted and Immunotherapeutic Strategies in Chronic Myeloid Leukemia. Semin Hematol. Jan. 2003;40(1):87-96.
Sepehr et al., Distinct pattern of TP53 mutations in squamous cell carcinoma of the esophagus in Iran. Oncogene. Nov. 1, 2001;20(50):7368-7374.
Sepulveda-Amor et al., A randomized trial demonstrating successful boosting responses following simultaneous aerosols of measles and rubella (MR) vaccines in school age children. Vaccine. Jun. 21, 2002;20(21-22):2790-2795.
Shen et al., Cloned Dendritic Cells Can Present Exogenous Antigens on Both MHC Class I and Class II Molecules. J Immunol. Mar. 15, 1997;158(6)2723-2730.
Shen et al., Recombinant Listeria monocytogenes as a live vaccine vehicle for the induction of protective anti-viral cell-mediated immunity. Proc Natl Acad Sci USA. Apr. 25, 1995;92(9):3987-3991.
Das et al., Evaluation of a Western Equine Encephalitis recombinant E1 protein for protective immunity and diagnostics. Antiviral Res. Nov. 2004;64(2):85-92.
Davies et al., Characterisation of a recombinant Fv fragment of anti-MUC1 antibody HMFG1. Cancer Lett. Jul. 29, 1994;82(2):179-184.
De Backer et al., Characterization of the GAGE Genes That Are Expressed in Various Human Cancers and in Normal Testis. Cancer Res. Jul. 1, 1999;59(13):3157-3165.
de Villiers et al., Classification of papillomaviruses. Virology. Jun. 20, 2004;324(1):17-24.
Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64(10):3653-3660.
Disis and Cheever, HER-2/Neu Protein: A Target for Antigen-Specific Immunotherapy of Human Cancer. Adv Cancer Res. 1997;71:343-371.
Disis et al., Humoral Epitope-Spreading Following Immunization with a HER-2/neu Peptide Based Vaccine in Cancer Patients. J Clin Immunol. Sep. 2004;24(5):571-578.
Dosaka-Akita et al., Expression of N-Acetylglucosaminyltransferase V is Associated with Prognosis and Histology in Non-Small Cell Lung Cancers. Clin Cancer Res. Mar. 1, 2004;10(5):1773-1779.
Duxbury et al., CEACAM6 as a novel target for indirect type 1 immunotoxin-based therapy in pancreatic adenocarcinoma. Biochem Biophys Res Commun. May 7, 2004;317(3):837-843.
Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbiol. May 1997;35(5):1122-1130.
Engels et al., Serologic Evidence for Exposure to Simian Virus 40 in North American Zoo Workers. J Infect Dis. Dec. 15, 2004;190(12):2065-2069.
Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.
Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.
Estrada-Franco et al., Venezuelan Equine Encephalitis Virus, Southern Mexico. Emerg Infect Dis. Dec. 2004;10(12):2113-2121.
Fang et al., Expression of Dnmt1, demethylase, MeCP2 and methylation of tumor-related genes in human gastric cancer. World J Gastroenterol. Dec. 1, 2004;10(23):3394-3398.
Faure et al., Inducible Hsp70 as Target of Anticancer Immunotherapy: Identification of HLA-A*0201-Restricted Epitopes. Int J Cancer. Mar. 1, 2004;108(6):863-870.
Fleishhauer et al., The DAM Gene Family Encodes a New Group of Tumor-specific Antigens Recognized by Human Leukocyte Antigen Al-restricted Cytotoxic T Lymphocytes. Cancer Res. Jul. 15, 1998;58(14):2969-2972.
Fong et al., Altered peptide ligand vaccination with Flt3 ligand expanded dendritic cells for tumor immunotherapy. Proc Natl Acad Sci U S A. Jul. 17, 2001;98(15):8809-8814.
Fuessel et al., Multiple tumor marker analyses (PSA, hK2, PSCA, trp-p8) in primary prostate cancers using quantitative RT-PCR. Int J Oncol. Jul. 2003;23(1):221-228.
Gaillard et al., Entry of L. monocytogenes into Cells is Mediated by Internalin, a Repeat Protein Reminiscent of Surface Antigens from Gram-Positive Cocci. Cell. Jun. 28, 1991;65(7):1127-1141.
Gambus et al., Epitope mapping of a mouse monoclonal anti-MUC2 antibody suggests the existence of an immunodominant region in the COOH terminus of the MUC2 tandem-repeat sequence. Int J Cancer. Jan. 3, 1995;60(1):146-148.
Geisbert and Jahrling, Differentiation of filoviruses by electron microscopy. Virus Res. Dec. 1995;39(2-3):129-150.
Ghazizadeh et al., Role of cdk4, p16INK4, and Rb Expression in the Prognosis of Bronchioloalveolar Carcinomas. Respiration. Jan.-Feb. 2005;72(1):68-73.
Gherardi et al., Towards a new generation of vaccines: the cytokine IL-12 as an adjuvant to enhance cellular immune responses to pathogens during prime-booster vaccination regimens. Histol Histopathol. Apr. 2001;16(2):655-667.
Gilliam et al., A phase II study of G17DT in gastric carcinoma. Eur J Surg Oncol. Jun. 2004;30(5):536-543.
Gonzalez et al., A comparative sequence analysis to revise the current taxonomy of the family Coronaviridae. Arch Virol. Nov. 2003;148(11):2207-2235.
Good et al., Development and regulation of cell-mediated immune responses to the blood stages of malaria: implications mplications for vaccine research. Annu Rev Immunol. 2005;23:69-99.
Good et al., The immunological challenge to developing a vaccine to the blood stages of malaria parasites. Immunol Rev. Oct. 2004;201:254-267.
Greiner et al., Vaccine-Based Therapy Directed against Carcinoembryonic Antigen Demonstrates Antitumor Activity on Spontaneous Intestinal Tumors in the Absence of Autoimmunity. Cancer Res. Dec. 1, 2002;62(23):6944-6951.
Grimm et al., Mouse alpha-fetoprotein-specific DNA-based immunotherapy of hepatocellular carcinoma leads to tumor regression in mice. Gastroenterology. Oct. 2000;119(4):1104-1112.
Groh et al., Efficient cross-priming of tumor antigen-specific T cells by dendritic cells sensitized with diverse anti-MICA opsonized tumor cells. Proc Natl Acad Sci USA. May 3, 2005;102(18):6461-6466.
Groth and Calos, Phage Integrases: Biology and Applications. J Mol Biol. Jan. 16, 2004;335(3):667-678.
Gueguen et al., An Antigen Recognized by Autologous CTLs on a Human Bladder Carcinoma. J Immunol. Jun. 15, 1998;160(12):6188-6194.
Gulmann et al., Adenomatous Polyposis Coli Gene, beta-Catenin, and E-Cadherin Expression in Proximal and Distal Gastric Cancers and Precursor Lesions. Appl Immunohistochem Mol Morphol. Sep. 2003;11(3):230-237.
Gunn et al., Two Listeria Monocytogenes Vaccine Vectors That Express Different Molecular Forms of Human Papilloma Virus-16 (HPV-16) E7 Induce Qualitatively Different T Cell Immunity That Correlates With Their Ability to Induce Regression of Established Tumors Immortalized by HPV-16. J Immunol. Dec. 1, 2001;167(11):6471-6479.
Gupta et al., Refolding, purification, and crystallization of apical membrane antigen 1 from Plasmodium falciparum. Protein Expr Purif. May 2005;41(1):186-198.
Haddad et al., Novel antigen identification method for discovery of protective malaria antigens by rapid testing of DNA vaccines encoding exons from the parasite genome. Infect Immun. Mar. 2004;72(3):1594-1602.

(56) References Cited

OTHER PUBLICATIONS

Hakansson et al., Establishment and phenotypic characterization of human U937 cells with inducible P210 BCR/ABL expression reveals upregulation of CEACAM1 (CD66a). (2004) Leukemia 18:538-547.

Harris et al., The Biological and Therapeutic Importance of Gastrin Gene Expression in Pancreatic Adenocarcinomas. Cancer Res. Aug. 15. 2004;64(16):5624-5631.

Hashido et al., Evaluation of an Enzyme-Linked Immunosorbent Assay Based on Binding Inhibition for Type-Specific Quantification of Poliovirus Neutralization-Relevant Antibodies. Microbiol Immunol. 1999;43(1):73-77.

Hassan et al., Mesothelin: A New Target for Immunotherapy. Clin Cancer Res. Jun. 15, 2004;10(12 Pt 1):3937-3942.

Havlasova et al., Mapping of immunoreactive antigens of Francisella tularensis live vaccine strain. Proteomics. Jul. 2002;2(7):857-867.

Havlasova et al., Proteomic analysis of anti-Francisella tularensis LVS antibody response in murine model of tularemia. Proteomics. May 2005;5(8):2090-2103.

He et al., Complexes of Poliovirus Serotypes with Their Common Cellular Receptor, CD155. J Virol. Apr. 2003;77 (8):4827-4835.

Hirose et al., Incidence of Diffuse Large B-Cell Lymphoma of Germinal Center B-Cell Origin in Whole Diffuse Large B-Cell Lymphoma: Tissue Fluorescence in Situ Hybridization Using t(14;18) Compared with Immunohistochemistry. Int J Hematol. Jan. 2005;81(1):48-57.

Hoffman et al., Strategy for development of a pre-erythrocytic Plasmodium falciparum DNA vaccine for human use. Vaccine. Jun. 1997;15(8):842-845.

Hoke, History of U.S. Military Contributions to the Study of Viral Encephalitis. Mil Med. Apr. 2005;170(4 Suppl):92-105.

Horton, In Vitro Recombination and Mutagenesis of DNA: SOEing Together Tailor-Made Genes. Methods Mol Biol. 1993;15:251-261.

Howard et al., Differentiation of Listeria monocytogenes, Listeria innocua, Listeria ivanovii, and Listeria seeligeri by pulsed-field gel electrophoresis. Appl Environ Microbiol. Feb. 1992;58(2):709-712.

Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.

Hutchinson et al., Multiplex Analysis of Cytokines in the Blood of Cynomolgus Macaques Naturally Infected With Ebola Virus (Reston Serotype). J Med Virol. Nov. 2001;65(3):561-566.

Iacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 15, 2003;63(24):8614-8622.

Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.

Isherwood et al., Vaccination strategies for Francisella tularensis. Adv Drug Deily Rev. Jun. 17, 2005;57 (9):1403-1414.

Ito et al., Prostate Carcinoma Detection and Increased Prostate-Specific Antigen Levels after 4 Years in Dutch and Japanese Males Who Had No Evidence of Disease at Initial Screening. Cancer. Jan. 15, 2005;103(2):242-250.

Jainkittivong and Langlais, Herpes B virus infection. Oral Surg Oral Med Oral Pathol Oral Radiol Endod. Apr. 1998; 85(4):399-403.

Jamieson et al., Human Torovirus: A New Nosocomial Gastrointestinal Pathogen. J Infect Dis. Nov. 1998;178(5):1263-1269.

Jansen and Shaw, Human Papillomavirus Vaccines and Prevention of Cervical Cancer. Annu Rev Med. 2004;55:319-331.

Johnson et al., Natural Atypical Listeria innocua Strains with Listeria monocytogenes Pathogenicity Island 1 Genes. Appl Environ Microbiol. Jul. 2004;70(7):4256-4266.

Jones and Portnoy, Characterization of Listeria monocytogenes Pathogenesis in a Strain Expressing Perfringolysin O in Place of Listeriolysin O. Infect Immun. Dec. 1994;62(12):5608-5613.

Jung et al., Strategies Against Human Papillomavirus Infection and Cervical Cancer. J Microbiol. Dec. 2004;42 (4):255-266.

Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.

Kann and Goldstein, Performance Evaluation of a New Algorithm for the Detection of Remote Homologs With Sequence Comparison. Proteins. Aug. 1, 2002;48(2):367-376.

Kaufman et al., Parvovirus B19 does not bind to membrane-associated globoside in vitro. Virology. Feb. 5, 2005;332 (1):189-198.

Kedl et al., Comparative Sequence Analysis of the Reovirus S4 Genes from 13 Serotype 1 and Serotype 3 Field Isolates. (1995) J. Virol. 69:552-559.

Kim et al., Comparison of HPV DNA vaccines employing intracellular targeting strategies. Gene Ther. Jun. 2004;11(12):1011-1018.

Krzych et al., T Lymphocytes from Volunteers Immunized with Irradiated Plasmodium Falciparum Sporozoites Recognize Liver and Blood Stage Malaria Antigens. J Immunol. Oct. 15, 1995;155(8):4072-4077.

Kubuschok et al., Expression of Cancer Testis Antigens in Pancreatic Carcinoma Cell Lines, Pancreatic Adenocarcinoma and Chronic Pancreatitis. Int J Cancer. Apr. 20, 2004;109(4):568-575.

Kumamuru et al., T-Cell Receptor Vbeta Gene Usage by T Cells Reactive with the Tumor-Rejection Antigen SART-1 in Oral Squamous Cell Carcinoma. Int J Cancer. Feb. 20, 2004;108(5):686-695.

Kyte and Doolittle, A Simple Method for Displaying the Hydropathic Character of a Protein. J Mol Biol. May 5, 1982;157(1):105-132.

Laheru and Jaffee, Immunotherapy for Pancreatic Cancer—Science Driving Clinical Progress. Nat Rev Cancer. Jun. 2005;5(6):459-467.

Lalic-Multhaler et al., In vitro transcription of PrfA-dependent and -independent genes of Listeria monocytogenes. Mol Microbiol. Oct. 2001;42(1):111-120.

Le et al., A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction. Clin Cancer Res. Feb. 1, 2012;18 (3):858-868.

Lee et al., Immunomic analysis of human sarcoma. Proc Natl Acad Sci USA. Mar. 4, 2003;100(5):2651-2656.

Leroux-Roels et al., Prevention of Hepatitis B Infections: Vaccination and its Limitations. Acta Clin Belg. Jul.-Aug. 2001;56(4):209-219.

Li et al., Advanced Glycation End Products Induce Tubular Epithelial-Myofibroblast Transition through the RAGE-ERK112 MAP Kinase Signaling Pathway. Am J Pathol. Apr. 2004;164(4):1389-1397.

Li et al., Expression Profile of Cancer-Testis Genes in 121 Human Colorectal Cancer Tissue and Adjacent Normal Tissue. Clin Cancer Res. Mar. 1, 2005;11(5):1809-1814.

Liang et al., Microvessel density, cyclo-oxygenase 2 expression, K-ras mutation and p53 overexpression in colonic cancer. Br J Surg. Mar. 2004;91(3):355-361.

Liau et al., Tumor Immunity within the Central Nervous System Stimulated by Recombinant Listeria Monocytogenes Vaccination. Cancer Res. Apr. 15, 2002;62(8):2287-2293.

Lim et al., Molecular and phenotypic spectrum of de novo Philadelphia positive acute leukemia. Int J Mol Med. Dec. 1999;4(6):665-667.

Lin et al., Melanoma-Associated Antigens in Esophageal Adenocarcinoma: Identification of Novel MAGE-A10 Splice Variants. Clin Cancer Res. Sep. 1, 2004;10(17):5708-5716.

Lingnau et al., Expression of the Listeria monocytogenes EGD inIA and inIB Genes, Whose Products Mediate Bacterial Entry into Tissue Culture Cell Lines, by PrfA-Dependent and -Independent Mechanisms. Infect Immun. Oct. 1995,63(10):3896-3903.

Lucas et al., MAGE-B5, MAGE-B6, MAGE-C2, and MAGE-C3: Four New Members of the MAGE Family with Tumor-Specific Expression. Int J Cancer. Jul. 1, 2000;87(1):55-60.

(56) References Cited

OTHER PUBLICATIONS

Luo et al., in vitro transcription of the Listeria monocytogenes virulence genes inlC and mpl reveals overlapping PrfA-dependent and -independent promoters that are differentially activated by GTP. Mol Microbiol. Apr. 2004;52(1):39-52.
Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.
Mandruzzato et al., A CASP-8 Mutation Recognized by Cytolytic T Lymphocytes on a Human Head and Neck Carcinoma. J Exp Med. Aug. 29, 1997;186(5):785-793.
Marth, Booster Policy for Adults. Biologicals. Jun. 1997;25(2):199-203.
Matsumoto et al., Expression of the SART-1 Antigens in Uterine Cancers. Jpn J Cancer Res. Dec. 1998;89(12):1292-1295.
Matsushita et alPreferentially Expressed Antigen of Melanoma (PRAME) in the Development of Diagnostic and Therapeutic Methods for Hematological Malignancies. Leuk Lymphoma. Mar. 2003;44(3):439-444.
Mayo et al., Mdm-2 Phosphorylation by DNA-dependent Protein Kinase Prevents Interaction with p53l. Cancer Res. Nov. 15, 1997;57(22):5013-5016.
McCool et al., Roles of calreticulin and calnexin during mucin synthesis in LS180 and HT29/A1 human colonic adenocarcinoma cells. Biochem J. Aug. 1, 1999;341 ( Pt 3):593-600.
Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.
Molijn et al., Molecular diagnosis of human papillomavirus (HPV) infections. J Clin Virol. Mar. 2005;32 Suppl 1: S43-51-S51.
Moreau-Aubry et al., A Processed Pseudogene Codes for a New Antigen Recognized by a CD8+ T Cell Clone on Melanoma. J Exp Med. May 1, 2000;191(9):1617-1624.
Morse et al., A Phase I Study of Active Immunotherapy with Carcinoembryonic Antigen Peptide (CAP-1)-Pulsed, Autologous Human Cultured Dendritic Cells in Patients with Metastatic Malignancies Expressing Carcinoembryonic Antigen. Clin Cancer Res. Jun. 1999;5(6):1331-1338.
Moutaftsi et al., A consensus epitope prediction approach identifies the breadth of murine TCD8+-cell responses to vaccinia virus. Nat Biotechnol. Jul. 2006;24(7):817-819.
Mueller and Freitag, Pleiotropic Enhancement of Bacterial Pathogenesis Resulting from the Constitutive Activation of the Listeria monocytogenes Regulatory Factor PrfA. Infect Immun. Apr. 2005;73(4):1917-1926.
Mukhopadhyay et al., A Structural Perspective of the Flavivirus Life Cycle. Nat Rev Microbiol. Jan. 2005;3(1):13-22.
Mulders et al., Tumor antigens and markers in renal cell carcinoma. Urol Clin North Am. Aug. 2003;30(3):455-465.
Muller et al., MeCP2 and MBD2 expression in human neoplastic and non-neoplastic breast tissue and its association with oestrogen receptor status. Br J Cancer. Nov. 17, 2003;89(10):1934-1939.
Shetron-Rama et al., Intracellular Induction of Listeria monocytogenes actA Expression. Infect Immun. Mar. 2002;70 (3):1087-1096.
Shetron-Rama et al., Isolation of Listeria monocytogenes mutants with high-level in vitro expression of host cytosol-induced gene products. Mol Microbiol. Jun. 2003;48(6):1537-1551.
Shigemasa et al., Expression of the protease inhibitor antileukoprotease and the serine protease stratum corneum chymotryptic enzyme (SCCE) is coordinated in ovarian tumors. Int J Gynecol Cancer. Nov.-Dec. 2001;11(6):454-461.
Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.
Shirasawa et al., Receptor for advanced glycation end-products is a marker of type I lung alveolar cells. Genes Cells. Feb. 2004;9(2):165-174.
Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64 (11):3757-3760.
Siegel et al., Induction of antitumour immunity using survivin peptide-pulsed dendritic cells in a murine lymphoma model. Br J Haematol. Sep. 2003;122(6):911-914.
Simon et al., A Broad Host Range Mobilization System for In Vivo Genetic Engineering: Transposon Mutagenesis in Gram Negative Bacteria. Nature Biotechnology 1983;1:784-791.
Simon et al., Cervical response to vaccination against HPV16 E7 in case of severe dysplasia. Eur J Obstet Gynecol Reprod Biol. Aug. 15, 2003;109(2):219-223.
Sjolander et al., Serological divergence of Dobrava and Saaremaa hantaviruses: evidence for two distinct serotypes. Epidemiol Infect. Feb. 2002;128(1):99-103.
Skoble et al., Three Regions within ActA Promote Arp2/3 Complex-Mediated Actin Nucleation and Listeria monocytogenes Motility. J Cell Biol. Aug. 7, 2000;150(3):527-538.
Slager et al., Identification of Multiple HLA-DR-Restricted Epitopes of the Tumor-Associated Antigen CAMEL by CD4+ Th1/Th2 Lymphocytes. J Immunol. Apr. 15, 2004;172(8):5095-5102.
Slager et al., Induction of CAMEL/NY-ESO-ORF2-specific CD8+ T cells upon stimulation with dendritic cells infected with a modified Ad5 vector expressing a chimeric Ad5/35 fiber. Cancer Gene Ther. Mar. 2004:11(3):227-236.
Slansky et al., Enhanced Antigen-Specific Antitumor Immunity with Altered Peptide Ligands that Stabilize the MHC-Peptide-TCR Complex. Immunity. Oct. 2000;13(4):529-538.
Small et al., Immunotherapy of Hormone-Refractory Prostate Cancer With Antigen-Loaded Dendritic Cells. J Clin Oncol. Dec. 1, 2000;18(23):3894-3903.
Smith and Thorpe, Diversity in the serine recombinases. Mol Microbiol. Apr. 2002;44(2):299-307.
Smith and Youngman, Use of a new integrational vector to investigate compartment-specific expression of the Bacillus subtilis spoIIM gene. Biochimie. Jul.-Aug. 1992;74(7-8):705-711.
Smith et al., Measurement of Cell-Mediated Immunity With a Varicella-Zoster Virus-specific Interferon-gamma Elispot Assay: Responses in an Elderly Population Receiving a Booster Immunization. J Med Virol. 2003;70 Suppl 1:S38-S41.
Smith et al., Neutralization of HIV-1 Subtypes: Implications for Vaccine Formulations. J Med Virol. Nov. 1998;56 (3):264-268.
Smits et al., Phylogenetic and Evolutionary Relationships among Torovirus Field Variants: Evidence for Multiple Intertypic Recombination Events. J Virol. Sep. 2003;77(17):9567-9577.
Stams et al., Expression Levels ofTEL, AML1, and the Fusion ProductsTEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8):2974-2980.
Steffens et al., Immunohistochemical Analysis of Tumor Antigen Saturation Following Injection of Monoclonal Antibody G250. Anticancer Res. Mar.-Apr. 1999:19(2A):1197-1200.
Stirnadel et al., Assessment of different sources of variation in the antibody responses to specific malaria antigens in in children in Papua New Guinea. Int J Epidemiol. Jun. 2000;29(3):579-586.
Stolier et al., Initial Experience with Surgical Treatment Planning in the Newly Diagnosed Breast Cancer Patient at High Risk for BRCA-1 or BRCA-2 Mutation. Breast J. Nov.-Dec. 2004;10(6):475-480.
Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.
Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.
Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8):1363-1370.

(56) References Cited

OTHER PUBLICATIONS

Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.
Tanaka et al., Expression of Tumor-rejection Antigens in Gynecologic Cancers. Jpn J Cancer Res. Nov. 2000;91 (11):1177-1184.
Tannapfel et al., BRAF Gene Mutations Are Rare Events in Gastroenteropancreatic Neuroendocrine Tumors. Am J Clin Pathol. Feb. 2005;123(2):256-260.
Topalian et al., Cancer Immunotherapy Comes of Age. J Clin Oncol. Dec. 20, 2011;29(36):4828-4836.
Treurnicht et al., HHV-8 Subtypes in South Africa: Identification of a Case Suggesting a Novel B Variant. J Med Virol. Feb. 2002;66(2):235-240.
Trimble et al., Comparison of the CD8+ T cell responses and antitumor effects generated by DNA vaccine administered through gene gun, biojector, and syringe. Vaccine. Sep. 8, 2003;21(25-26):4036-4042.
Trincado et al., Human Cytomegalovirus Strains Associated With Congenital and Perinatal Infections. J Med Virol. Aug. 2000;61(4):481-487.
Tsang et al., Phenotypic Stability of a Cytotoxic T-Cell Line Directed against an Immunodominant Epitope of Human Carcinoembryonic Antigen. Clin Cancer Res. Dec. 1997;3(12 Pt 1):2439-2449.
Tsao and Sober, Melanoma Treatment Update. Dermatol Clin. Apr. 2005;23(2):323-333.
Tsuruma et al., Phase I clinical study of anti-apoptosis protein, survivin-derived peptide vaccine therapy for patients with advanced or recurrent colorectal cancer J Transl Med. Jun. 13, 2004;2(1):19 (11 pages).
Vallejo et al., Nucleotide Sequence and Restriction Fragment-Length Polymorphism Analysis of Human T-Cell Lymphotropic Virus Type II (HTLV-II) in Southern Europe: Evidence for the HTLV-IIA and HTLV-IIB Subtypes. J Acquir Immune Defic Syndr Hum Retrovirol. Dec. 1, 1996;13(4):384-391.
Van Den Eynde et al., A New Antigen Recognized by Cytolytic T Lymphocytes on a Human Kidney Tumor Results from Reverse Strand Transcription. J Exp Med. Dec. 20, 1999;190(12):1793-1800.
Vandamme et al., African Origin of Human T-Lymphotropic Virus Type 2 (HTLV-2) Supported by a Potential New HTLV-2d Subtype in Congolese Bambuti Efe Pygmies. J Virol. May 1998;72(5):4327-4340.
Vazquez-Boland et al., Nucleotide Sequence of the Lecithinase Operon of Listeria monocytogenes and Possible Role of Lecithinase in Cell-to-Cell Spread. Infect Immun. Jan. 1992;60(1):219-230.
Vilas Boas et al., Cytomegalovirus Glycoprotein B Genotypes and Central Nervous System Disease in AIDS Patients. J Med Virol. Nov. 2003;71(3):404-407.
Vilchez and Butel, Emergent Human Pathogen Simian Virus 40 and Its Role in Cancer. Clin Microbiol Rev. Jul. 2004;17(3):495-508.
Virok et al., Chlamydial Infection Induces Pathobiotype-Specific Protein Tyrosine Phosphorylation in Epithelial Cells. Infect Immun. Apr. 2005;73(4):1939-1946.
Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4):1687-1697.
Waltregny et al., Screening of histone deacetylases (HDAC) expression in human prostate cancer reveals distinct class I HDAC profiles between epithelial and stromal cells. Eur J Histochem. Jul.-Sep. 2004;48(3):273-290.
Wang et al., Alterations of APC, c-met, and p53 Genes in Tumor Tissue and Serum of Patients with Gastric Cancers. J Surg Res. Aug. 2004;120(2):242-248.

Wang et al., Cloning Genes Encoding MHC Class II—Restricted Antigens: Mutated CDC27 as a Tumor Antigen. Science. May 21, 1999;284(5418):1351-1354.
Wang et al., Identification of a Novel Major Histocompatibility Complex Class II—restricted Tumor Antigen Resulting from a Chromosomal Rearrangement Recognized by CD4+ T Cells. J Exp Med. May 17, 1999;189(10):1659-1667.
Weaver et al., Genetic determinants of Venezuelan equine encephalitis emergence. Arch Virol Suppl. 2004; (18):43-64.
Abutaily et al., Cadherins, catenins and APC in pleural malignant mesothelioma. J Pathol. Nov. 2003;201(3):355-362.
Aguilar et al., Endemic Venezuelan equine encephalitis in northern Peru. Emerg Infect Dis. May 2004;10(5):880-888.
Ahn et al., All CVB Serotypes and Clinical Isolates Induce Irreversible Cytopathic Effects in Primary Cardiomyocytes. J Med Virol. Feb. 2005;75(2):290-294.
Albert et al., Site-specific integration of DNA into wild-type and mutant lox sites placed in the plant genome. Plant J. Apr. 1995;7(4):649-659.
Altwein and Luboldt, Prognostic Factors for Carcinoma of the Prostate. Urol Int. 1999;63(1):62-71.
Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. May 2005;64(5):780-782.
Andersen and thor Straten, Survivin—a universal tumor antigen. Histol Histopathol. Apr. 2002;17(2):669-675.
Argani et al., Discovery of New Markers of Cancer through Serial Analysis of Gene Expression Prostate Stem Cell Antigen is Overexpressed in Pancreatic Adenocarcinoma. Cancer Res. Jun. 1, 2001;61(11):4320-4324.
Arora et al., Identification of Differentially Expressed Genes in Oral Squamous Cell Carcinoma. Mol Carcinog. Feb. 2005;42(2):97-108.
Arslan et al., A new approach to sequence comparison: normalized sequence alignment. Bioinformatics. Apr. 2001;17(4):327-337.
Attoui et al., Comparative sequence analysis of American, European and Asian isolates of viruses in the genus Coltivirus. J Gen Virol. Oct. 1998;79 ( Pt 10):2481-2489.
Auerbuch et al., Development of a Competitive Index Assay to Evaluate the Virulence of Listeria monocytogenes actA Mutants during Primary and Secondary Infection of Mice. Infect Immun. Sep. 2001;69(9):5953-5957.
Bahjat et al., Cytosolic Entry Controls CD8+-T-Cell Potency during Bacterial Infection. Infect Immun. Nov. 2006;74 (11):6387-6397.
Barbanti-Brodano et al., Simian virus 40 infection in humans and association with human diseases: results and hypotheses. Virology. Jan. 5, 2004;318(1):1-9.
Barthold et al., Infectivity, Disease Patterns, and Serologic Profiles of Reovirus Serotypes 1, 2, and 3 in Infant and Weanling Mice. Lab Anim Sci. Oct. 1993;43(5):425-430.
Baurain et al., High Frequency of Autologous Anti-Melanoma CTL Directed Against an Antigen Generated by a Point Mutation in a New Helicase Gene. J Immunol. Jun. 1, 2000;164(11):6057-6066.
Belyakov et al., The Importance of Local Mucosal HIV-Specific CD8+ Cytotoxic T Lymphocytes for Resistance to Mucosal Viral Transmission in Mice and Enhancement of Resistance by Local Administration of IL-12. J Clin Invest. Dec. 15, 1998;102(12):2072-2081.
Berche et al., Intracellular Growth of Listeria monocytogenes as a Prerequisite for In Vivo Induction of T Cell-Mediated Immunity. J Immunol. Apr. 1, 1987;138(7):2266-2271.
Bevanger et al., Competitive Enzyme Immunoassay for Antibodies to a 43,000-Molecular-Weight Francisella tularensis Outer Membrane Protein for the Diagnosis of Tularemia. J Clin Microbiol. May 1989;27(5):922-926.
Bhigjee et al., Sequence of the env gene of some KwaZulu-Natal, South African strains of HTLV type I. AIDS Res Hum Retroviruses. Sep. 1, 1999;15(13):1229-1233.
Biagini et al., Simultaneous measurement of specific serum IgG responses to five select agents. Anal Bioanal Chem. Jun. 2005;382(4):1027-1034.

(56) References Cited

OTHER PUBLICATIONS

Bishop and Hinrichs, Adoptive transfer of immunity to Listeria monocytogenes. The influence of in vitro stimulation on lymphocyte subset requirements. J Immunol. Sep. 15, 1987;139(6):2005-2009.
Blankenstein et al., The determinants of tumour immunogenicity. Nature reviews. Nat Rev Cancer. Mar. 1, 2012;12(4):307-313.
Bondurant et al., Definition of an Immunogenic RegionWithin the OvarianTumor Antigen Stratum Corneum Chymotryptic Enzyme. Clin Cancer Res. May 1, 2005;11(9):3446-3454.
Brezniceanu et al., HMGB1 inhibits cell death in yeast and mammalian cells and is abundantly expressed in human breast carcinoma. FASEB J. Jul. 2003;17(10):1295-1297.
Brian and Baric, Coronavirus Genome Structure and Replication. Curr Top Microbiol Immunol. 2005;287:1-30.
Brinkmann et al., Novel Genes in the PAGE and GAGE Family of Tumor Antigens Found by Homology Walking in the dbEST Database. Cancer Res. Apr. 1, 1999;59(7):1445-1448.
Brockstedt et al., Killed but metabolically active microbes: a new vaccine paradigm for eliciting effector T-cell responses and protective immunity. Nat Med. Aug. 2005;11(8):853-860.
Brockstedt et al., Listeria-based cancer vaccines that segregate immunogenicity from toxicity. Proc Natl Acad Sci U S A. Sep. 21, 2004;101(38):13832-13837.
Bronte et al., Genetic Vaccination with "Self" Tyrosinase-related Protein 2 Causes Melanoma Eradication but not Vitiligo. Cancer Res. Jan. 15, 2000;60(2):253-258.
Brown et al., Complete Genomic Sequencing Shows that Polioviruses and Members of Human Enterovirus Species C are Closely Related in the Noncapsid Coding Region. J Virol. Aug. 2003;77(16):8973-8984.
Brown, Variants of B19. Dev Biol (Basel). 2004;118:71-77.
Camilli et al., Dual roles of plcA in Listeria monocytogenes pathogenesis. Mol Microbiol. Apr. 1993;8(1):143-157.
Capdepont et al., New Insights in HTLV-I Phylogeny by Sequencing and Analyzing the Entire Envelope Gene. AIDS Res Hum Retroviruses. Jan. 2005;21(1):28- 42.
Capurro et al., Glypican-3: A Novel Serum and Histochemical Marker for Hepatocellular Carcinoma. Gastroenterology. Jul. 2003;125(1):89-97.
Carbone et al., New developments about the association of SV40 with human mesothelioma. Oncogene. Aug. 11, 2003;22(33):5173-5180.
Chan et al., In Situ Hybridization Study of PSP94 (Prostatic Secretory Protein of 94 Amino Acids) Expression in Human Prostates. Prostate. Oct. 1, 1999;41(2):99-109.
Chang et al., A Phase I Trial of Tumor Lysate-Pulsed Dendritic Cells in the Treatment of Advanced Cancer. Clin Cancer Res. Apr. 2002;8(4):1021-1032.
Chen et al., Immunodominant CD41 responses identified in a patient vaccinated with full-length NY-ESO-1 formulated with ISCOMATRIX adjuvant. Proc Natl Acad Sci USA. Jun. 22, 2004;101(25):9363-9368.
Chern et al., Glycoprotein B Subtyping of Cytomegalovirus (CMV) in the Vitreous of Patients with AIDS and CMV Retinitis. J Infect Dis. Oct. 1998;178(4):1149-1153.
Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.
Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.
Clements et al., Adenomatous Polyposis Coli/β-Catenin Interaction and Downstream Targets: Altered Gene Expression in Gastrointestinal Tumors. Clin Colorectal Cancer. Aug. 2003;3(2):113-120.
Clifton et al., A chlamydial type III translocated protein is tyrosine-phosphorylated at the site of entry and associated with recruitment of actin. Proc Natl Acad Sci USA. Jul. 6, 2004;101(27):10166-10171.
Clinton et al., A Comparative Study of Four Serological Tumor Markers for the Detection of Breast Cancer. Biomed Sci Instrum. 2003;39:408-414.
Cobaleda et al., A primitive hematopoietic cell is the target for the leukemic transformation in human Philadelphia-positive acute lymphoblastic leukemia. Blood. Feb. 1, 2000;95(3):1007-1013.
Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.
Creighton et al., Mechanisms and catalysts of disulfide bond formation in proteins. Trends Biotechnol. Jan. 1995;13(1):18-23.
Dalerba et al., MAGE, BAGE and GAGE gene expression in human rhabdomyosarcomas. Int J Cancer. Jul. 1, 2001;93(1):85-90.
Damasus-Awatai and Freeman-Wang, Human papilloma virus and cervical screening. Curr Opin Obstet Gynecol. Dec. 2003;15(6):473-477.
International Search Report and Written Opinion issued in PCT/US2013/068800 dated Feb. 20. 2014.
Lauer et al., Constitutive Activation of the PrfA Regulon Enhances the Potency of Vaccines Based on Live-Attenuated and Killed but Metabolically Active Listeria monocytogenes Strains. Infect Immun. Aug. 2008;76(8):3742-3753.
Lauer et al., Construction, Characterization, and Use of Two Listeria monocytogenes Site-Specific Phage Integration Vectors. J Bacteriol. Aug. 2002;184(15):4177-4186.
Mandali et al., The site-specific integration reaction of Listeria phage A 118 integrase, a serine recombinase. Mob DNA. Jan. 3, 2013;4(1):2 (17 pages).
Search Report and Written Opinion issued by IPOS in Singapore application No. 11201502770P dated Nov. 8, 2015.
Extended European Search Report isued in EP 13853070 dated May 20, 2016.
Beare et al., Two Systems for Targeted Gene Deletion in Coxiella burnetii. Appl Environ Microbiol. Jul. 2012;78(13):4580-4589.
Lambert et al., Cre-lox-based system for multiple gene deletions and selectable-marker removal in Lactobacillus plantarum. Appl Environ Microbiol. Feb. 2007;73(4):1126-1135.
Lui et al., An in vivo gene deletion system for determining temporal requirement of bacterial virulence factors. Proc Natl Acad Sci U S A. Jul. 8, 2008;105(27):9385-9390.
Yin et al., Protective immunity induced by a LLO-deficient Listeria monocytogenes. Microbiol lmmunol. Apr. 2010;(4):175-183.

\* cited by examiner

Fig. 3
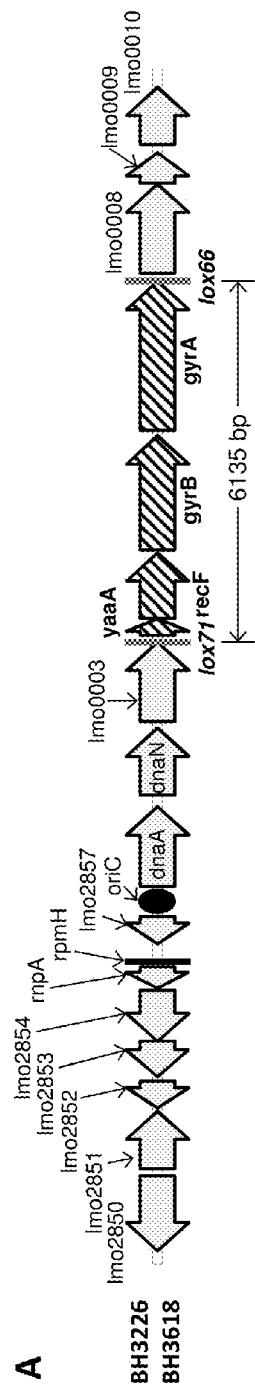
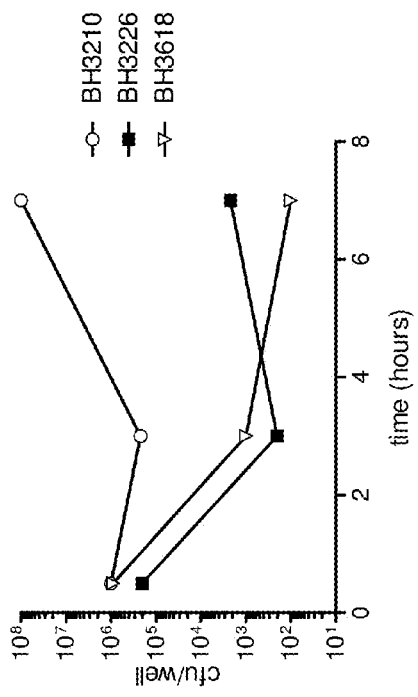
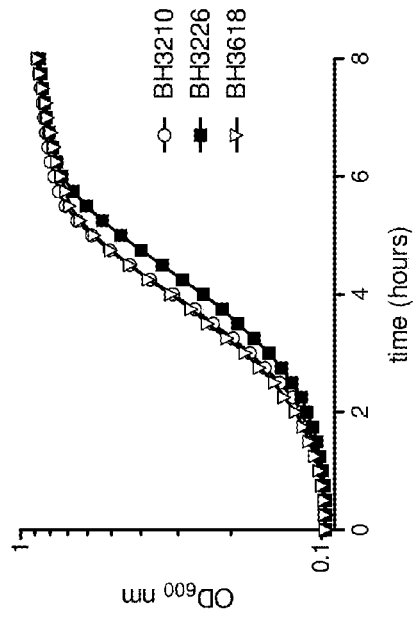

ial vaccine vector platforms have been developed for both prophylactic and therapeutic applications. Attenuated strains of many otherwise pathogenic bacteria are now available and the ease of manipulation for generating recombinant strains provides a means for using bacteria as efficacious delivery vehicles for a number of foreign proteins such as antigens associated with infectious diseases and cancer. Live attenuated bacterial vaccine strains have been developed from, inter alia, *Listeria, Escherichia, Salmonella, Shigella, Lactobacillus*, and *Yersinia* species.

SEQUENCE LISTING

```
<160> NUMBER OF SEQ ID NOS: 57

<210> SEQ ID NO 1
<211> LENGTH: 237
<212> TYPE: PRT
<213> ORGANISM: Listeria monocytogenes

<400> SEQUENCE: 1

Met Asn Ala Gln Ala Glu Glu Phe Lys Lys Tyr Leu Glu Thr Asn Gly
1               5                   10                  15

Ile Lys Pro Lys Gln Phe His Lys Lys Glu Leu Ile Phe Asn Gln Trp
            20                  25                  30

Asp Pro Gln Glu Tyr Cys Ile Phe Leu Tyr Asp Gly Ile Thr Lys Leu
        35                  40                  45

Thr Ser Ile Ser Glu Asn Gly Thr Ile Met Asn Leu Gln Tyr Tyr Lys
    50                  55                  60

Gly Ala Phe Val Ile Met Ser Gly Phe Ile Asp Thr Glu Thr Ser Val
65                  70                  75                  80

Gly Tyr Tyr Asn Leu Glu Val Ile Ser Glu Gln Ala Thr Ala Tyr Val
                85                  90                  95

Ile Lys Ile Asn Glu Leu Lys Glu Leu Leu Ser Lys Asn Leu Thr His
            100                 105                 110

Phe Phe Tyr Val Phe Gln Thr Leu Gln Lys Gln Val Ser Tyr Ser Leu
```

```
                115                 120                 125
Ala Lys Phe Asn Asp Phe Ser Ile Asn Gly Lys Leu Gly Ser Ile Cys
    130                 135                 140

Gly Gln Leu Leu Ile Leu Thr Tyr Val Tyr Gly Lys Glu Thr Pro Asp
145                 150                 155                 160

Gly Ile Lys Ile Thr Leu Asp Asn Leu Thr Met Gln Glu Leu Gly Tyr
                165                 170                 175

Ser Ser Gly Ile Ala His Ser Ser Ala Val Ser Arg Ile Ile Ser Lys
            180                 185                 190

Leu Lys Gln Glu Lys Val Ile Val Tyr Lys Asn Ser Cys Phe Tyr Val
        195                 200                 205

Gln Asn Leu Asp Tyr Leu Lys Arg Tyr Ala Pro Lys Leu Asp Glu Trp
    210                 215                 220

Phe Tyr Leu Ala Cys Pro Ala Thr Trp Gly Lys Leu Asn
225                 230                 235

<210> SEQ ID NO 2
<211> LENGTH: 29
<212> TYPE: PRT
<213> ORGANISM: Listeria monocytogenes

<400> SEQUENCE: 2

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala
            20                  25

<210> SEQ ID NO 3
<211> LENGTH: 100
<212> TYPE: PRT
<213> ORGANISM: Listeria monocytogenes

<400> SEQUENCE: 3

Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly
            100

<210> SEQ ID NO 4
<211> LENGTH: 100
<212> TYPE: PRT
<213> ORGANISM: Listeria monocytogenes

<400> SEQUENCE: 4

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30
```

-continued

Ser Glu Asp Ser Ser Leu Asn Thr Asp Glu Trp Glu Glu Lys Thr
         35                  40                  45

Glu Glu Gln Pro Ser Glu Val Asn Thr Gly Pro Arg Tyr Glu Thr Ala
     50                  55                  60

Arg Glu Val Ser Arg Asp Ile Glu Glu Leu Glu Lys Ser Asn Lys
 65                  70                  75                  80

Val Lys Asn Thr Asn Lys Ala Asp Leu Ile Ala Met Leu Lys Ala Lys
             85                  90                  95

Ala Glu Lys Gly
         100

<210> SEQ ID NO 5
<211> LENGTH: 102
<212> TYPE: PRT
<213> ORGANISM: Listeria monocytogenes

<400> SEQUENCE: 5

Val Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
             20                  25                  30

Ser Glu Asp Ser Ser Leu Asn Thr Asp Glu Trp Glu Glu Lys Thr
         35                  40                  45

Glu Glu Gln Pro Ser Glu Val Asn Thr Gly Pro Arg Tyr Glu Thr Ala
     50                  55                  60

Arg Glu Val Ser Arg Asp Ile Glu Glu Leu Glu Lys Ser Asn Lys
 65                  70                  75                  80

Val Lys Asn Thr Asn Lys Ala Asp Leu Ile Ala Met Leu Lys Ala Lys
             85                  90                  95

Ala Glu Lys Gly Gly Ser
         100

<210> SEQ ID NO 6
<211> LENGTH: 102
<212> TYPE: PRT
<213> ORGANISM: Listeria monocytogenes

<400> SEQUENCE: 6

Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
             20                  25                  30

Ser Glu Asp Ser Ser Leu Asn Thr Asp Glu Trp Glu Glu Lys Thr
         35                  40                  45

Glu Glu Gln Pro Ser Glu Val Asn Thr Gly Pro Arg Tyr Glu Thr Ala
     50                  55                  60

Arg Glu Val Ser Arg Asp Ile Glu Glu Leu Glu Lys Ser Asn Lys
 65                  70                  75                  80

Val Lys Asn Thr Asn Lys Ala Asp Leu Ile Ala Met Leu Lys Ala Lys
             85                  90                  95

Ala Glu Lys Gly Gly Ser
         100

<210> SEQ ID NO 7
<211> LENGTH: 33
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 7
tttcggccga tgagtaacct attaactgtt cat                                33

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tttggatcct tagtctccat cttctaataa t                                  31

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tttggtaccg gtcatgatga cattaataca aca                                33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tttgagctct atcctaaatg gctttatatc agt                                33

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttaagcttt tggaaattcg attaccccac t                                  31

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttggtacct ggttattttc gtcgaataac tgcc                               34

<210> SEQ ID NO 13
<211> LENGTH: 44
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 13
tttggtacct ttgagctctt ttagtaaaaa aacgccagag aagc                    44

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tttgaattct ccgttgttgc aatattcgct                                    30

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tttaagcttt ccctgaagaa gaagtagcaa tta                                33

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tttggtacca gcttgatttt attcttctat gtcgc                              35

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tttggtacct tgagctcgg aaatgactct aatttgcgaa t                        41

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tttgaattct ccatgtatac ccaatcgttt agga                               34

<210> SEQ ID NO 19
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
ataacttcgt atagcataca ttatacgaac ggtaggaaat gactctaatt tgcgaat        57

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tttgaattct ccatgtatac ccaatcgttt agga                                 34

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tttaagcttt ccctgaagaa gaagtagcaa tta                                  33

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
taccgttcgt ataatgtatg ctatacgaag ttatagcttg attttattct tctatgtcgc     60

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tttgaattca cagaaggaga ttgtgaaatg                                      30

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggtctagat ttggtaccaa tagaagcgta ctgcgact                             38

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
gggtctagag tttcacgtga aacattcta                               29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tttaagcttc ggaattggtt caagactgg                               29

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
attggtacct tcgaggagta aacttcccaa                              30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aactctagac accgcggtgg cggccgataa                              30

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tatgcggccg cgggaagcag ttggggttaa ct                           32

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aactctagac ttagtctcca tcttctaata                              30

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 31
aaaggaagtt cctattctct agaaagtata ggaacttctg cggaaatgac tctaatttgc    60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcagaagttc ctatactttc tagagaatag gaacttcctt tagcttgatt ttattcttct    60

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aaaggaagtt cctattctct agaaagtata ggaacttctg cttttagtaa aaaacgcca    60

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcagaagttc ctatactttc tagagaatag gaacttcctt ttggttattt tcgtcgaata    60

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tttctgcagg tggatagaac tcataaagga c                                   31

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tttggtacct cagttaaccc caactgcttc                                     30

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tttggtacct ttagatctaa acacagaacg aaagaaaaag                              40

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tttgaattcc cagtaggttc cactgtatc                                         29

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tttctgcagt ccatgtatac ccaatcgttt agga                                   34

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tttaagcttt ccctgaagaa gaagtagcaa tta                                    33

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tttagatcta aatggttttt ctctctataa                                        30

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tagatctata acttcgtata gcatacatta tacgaacggt attcgaaaat tattgcgtta       60

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tttctgcaga tgattcaatc cttcttgctt                                        30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gggtctagag agttatacaa aacgggaata                                        30

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ataacttcgt atagcataca ttatacgaac ggta                                   34

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
taccgttcgt atagcataca ttatacgaag ttat                                   34

<210> SEQ ID NO 47
<211> LENGTH: 34
<212> TYPE: DNA
<213> ORGANISM: Listeria monocytogenes

<400> SEQUENCE: 47
ataacttcgt ataatgtatg ctatacgaag ttat                                   34

<210> SEQ ID NO 48
<211> LENGTH: 221
<212> TYPE: DNA
<213> ORGANISM: Listeria monocytogenes

<400> SEQUENCE: 48
gggaagcagt tggggttaac tgattaacaa atgttagaga aaaattaatt ctccaagtga       60
tattcttaaa ataattcatg aatattttt cttatattag ctaattaaga agataattaa       120
ctgctaatcc aattttaac ggaataaatt agtgaaaatg aaggccgaat tttccttgtt       180 ctaaaaggt tgtattagcg tatcacgagg agggagtata a                           221

<210> SEQ ID NO 49
<211> LENGTH: 1032
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atgagtaacc tattaactgt tcatcaaaat ttaccagcat taccagtgga tgcaacatca      60

```
gatgaagtaa gaaaaaattt aatggatatg tttagagacc gacaagcctt ttcggagcat    120
acatggaaaa tgttattatc tgtttgtaga tcatgggcag catggtgcaa acttaacaat    180
agaaaatggt ttccagcaga accagaagat gtacgagatt atttattata ccttcaagca    240
agaggattag cagtaaaaac cattcaacaa catttaggac aattaaatat gttacataga    300
cgatcaggat taccaagacc tagcgattct aacgcagtta gtttagttat gagaagaatt    360
agaaaagaaa atgtcgatgc aggcgaacga gcaaaacaag cactagcatt tgaacgtaca    420
gatttcgacc aagtaagatc attaatggaa aatagcgacc gttgtcaaga catccgaaac    480
ttagcttttt taggaatagc atacaacaca ttattaagaa tagcagaaat agccagaatt    540
agagtaaaag acattagtag aacagatgga ggaagaatgt taattcatat tggaagaaca    600
aaaacattag tatcaacagc cggggtagaa aaagcgttat cattaggagt tacaaaatta    660
gtagaacgat ggatttcagt ttcaggagtg gcagatgacc caaataatta tttatttttgt    720 agagtacgaa aaaacggagt agcagcacct tcagcaacaa gtcaattaag tacaagagca    780
ttagaaggaa tattcgaagc aacacatcga ctaatttacg gagcaaaaga tgatagtgga    840
caacgatatt tagcttggag tggacacagt gcgcgagtag gagcagcaag agatatggca    900
agagcgggag ttagtatacc agaaataatg caagcaggag gatggacaaa tgtaaatatt    960
gtaatgaatt atattagaaa tttagatagt gaaaccggtg caatggtacg attattagaa   1020
gatggagact aa                                                       1032

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gaagttccta ttctctagaa agtataggaa cttc                                34

<210> SEQ ID NO 51
<211> LENGTH: 1272
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
atgtcgcaat tgatatact atgtaaaact ccacctaaag tattagtgcg tcaatttgtt     60
gaacgttttg aacgaccaag tggcgaaaag atagcttcct gtgccgcgga acttacttac   120
ttgtgttgga tgattacaca taatggcact gcaatcaaaa gagcaacatt catgtcatac   180
aacaccatca tttctaattc tttatcattt gatattgtta acaaaagttt acaattcaaa   240
tacaaaactc aaaaagcgac gattcttgaa gctagtttga aaaagttaat cccagcatgg   300
gagtttacca tcattcctta caatggacag aaacaccaat ccgacattac agacattgtt   360
tctagtttac aactacaatt tgaaagcagt gaagaagcgg ataaagggaa ctcacattcg   420
aagaaaatgt taaaggcttt gttatctgaa ggagaatcta tctgggagat tacagaaaag   480
attctaaact cttttgagta tacttcacgc tttactaaaa ccaaaacgtt ataccagttt   540 cttttttctag ctacattcat taactgcggt cgatttagtg acattaagaa tgtagatcct   600
```

```
aaatcgttca agttagtcca aaacaagtat ctaggtgtca tcattcaatg cttagttacg    660
gaaacaaaaa cgagtgtaag tagacatatc tatttctttt ctgctagagg tagaattgat    720
ccgcttgtat acttagatga atttctacgt aattcagagc cggtgcttaa acgcgttaat    780
cgtacaggaa atagctcaag caataagcaa gaatatcaac ttttgaaaga caatttggtg    840
cgtagctata acaaagcgtt aaagaagaat gcaccatatc cgatattcgc catcaaaaac    900
gggccaaaat cccacattgg tcgccatctt atgactagct tcctttcgat gaaaggatta    960
acggagttaa caaatgtggt aggtaattgg tccgacaaaa gagcgagtgc tgtagcacga   1020
acgacatata cacatcagat tacagctatt ccagatcact actttgcatt agttagtaga   1080
tactatgcat atgatccaat ttccaaagaa atgattgctc ttaaagatga aacaaatcca   1140
atagaagaat ggcaacatat cgaacaactt aaaggatcgg cagaaggctc tatacgttat   1200
cctgcatgga atggtatcat ttctcaagaa gttttagact atttgtcaag ctatatcaat   1260
cgtcgcattt aa                                                       1272
```

<210> SEQ ID NO 52
<211> LENGTH: 9
<212> TYPE: PRT
<213> ORGANISM: Vaccinia virus

<400> SEQUENCE: 52

Tyr Ala Pro Val Ser Pro Ile Val Ile
1               5

<210> SEQ ID NO 53
<211> LENGTH: 8
<212> TYPE: PRT
<213> ORGANISM: Vaccinia virus

<400> SEQUENCE: 53

Leu Asn Phe Arg Phe Glu Asn Val
1               5

<210> SEQ ID NO 54
<211> LENGTH: 10
<212> TYPE: PRT
<213> ORGANISM: Vaccinia virus

<400> SEQUENCE: 54

Tyr Ser Leu Pro Asn Ala Gly Asp Val Ile
1               5                   10

<210> SEQ ID NO 55
<211> LENGTH: 8
<212> TYPE: PRT
<213> ORGANISM: Vaccinia virus

<400> SEQUENCE: 55

Thr Ser Tyr Lys Phe Glu Ser Val
1               5

<210> SEQ ID NO 56
<211> LENGTH: 8
<212> TYPE: PRT
<213> ORGANISM: Gallus sp.

<400> SEQUENCE: 56

Ser Ile Ile Asn Phe Glu Lys Leu
1               5

```
<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Pro Ser Tyr Ala Tyr His Gln Phe
1               5
```

FACULTATIVELY ATTENUATED BACTERIAL SPECIES AND METHODS OF PREPARATION AND USE THEREOF

CROSS REFERENCES TO RELATED APPLICATIONS

This application claims the benefit of U.S. Provisional Application No. 61/723,234, filed Nov. 6, 2012, which is hereby incorporated in its entirety including all tables, figures, and claims.

SEQUENCE LISTING

The instant application contains a Sequence Listing which has been submitted electronically in ASCII format and is hereby incorporated by reference in its entirety. Said ASCII copy, created on Dec. 9, 2013, is named ANZ7000UT_SeqList_Text.txt and is 20,677 bytes in size.

BACKGROUND OF THE INVENTION

The following discussion of the background of the invention is merely provided to aid the reader in understanding the invention and is not admitted to describe or constitute prior art to the present invention.

Pathogenic organisms are, by definition, capable of causing disease in an infected host. For clinical use of such organisms, attenuated vaccine strains are often created which exhibit reduced or eliminated virulence, but which still retain sufficient viability to stimulate a desired immune response against the pathogen or heterologous antigen(s) of interest. Attenuated vector platforms have been demonstrated to elicit protective responses specific for encoded heterologous antigens in a number of experimental models, including infectious and malignant diseases.

Although most attenuated vaccine vectors are viral, bacterial vaccine vector platforms have been developed for both prophylactic and therapeutic applications. Attenuated strains of many otherwise pathogenic bacteria are now available and the ease of manipulation for generating recombinant strains provides a means for using bacteria as efficacious delivery vehicles for a number of foreign proteins such as antigens associated with infectious diseases and cancer. Live attenuated bacterial vaccine strains have been developed from, inter alia, *Listeria, Escherichia, Salmonella, Shigella, Lactobacillus*, and *Yersinia* species.

While such vaccine strains may exhibit reduced virulence, their safety, particularly in immune compromised individuals, remains a concern. One example of a strategy to further reduce the risk of bacterial vaccines is the so-called Killed But Metabolically Active ("KBMA") approach. KBMA vaccine strains are constructed by abrogating the capacity for nucleotide excision repair through deletion of DNA repair genes such as uvrA and uvrB. The gene deletion renders the bacteria exquisitely sensitive to photochemical inactivation through the combined treatment of psoralens and UVA. Because of their inability to repair the psoralen-induced DNA cross-links formed, KBMA bacterial strains are unable to replicate and are thus functionally noninfectious. This characteristic provides an improved safety profile in comparison to live attenuated strains. The very limited number of cross-links, however, preserves their metabolic activity, including antigen expression, and thus their immune potential. Manufacturing of KBMA strains exhibiting consistent properties, however, may be difficult, as titration of the number of cross-links is dependent on a number of difficult to control variables.

There remains a need in the art to provide attenuated bacterial vaccine strains with advantageous safety profiles for use treatment or prevention of diseases having a risk-benefit profile not appropriate for live attenuated vaccines.

BRIEF SUMMARY OF THE INVENTION

The present invention provides facultatively attenuated bacterial species and methods of preparation and use thereof. The term "facultatively attenuated" as used herein refers to a bacterium which comprises a set of defined recombinant modifications which have substantially no effect on the ability of the bacterium to grow by multiplication when the bacterium is outside of its host organism, but which result in deletion of one or more genes essential for multiplication of the bacterium when the bacterium is introduced into its host organism, for example within host cells of a vaccinate recipient. These recombinant modifications take advantage of regulatory sequences which preferentially induce expression of genes within the mammalian host.

As described hereinafter, the bacterium is most preferably an intracellular pathogen, such as *Listeria monocytogenes*.

In a first aspect of the invention, the invention relates to methods of configuring a bacterium to delete one or more genes in the bacterial genome which are essential for multiplication of the bacterium, the deletion occurring preferentially when the bacterium is introduced into a host. These methods comprise:

(i) recombinantly introducing into the bacterium a nucleic acid encoding a recombinase heterologous to the bacterium, wherein the nucleic acid encoding the recombinase is operably connected to regulatory sequences which preferentially induce expression of the recombinase in a mammalian host cell, and (ii) recombinantly introducing in the bacterial genome a first attachment site for the recombinase upstream from the gene(s) essential for multiplication of the bacterium, and a second attachment site for the recombinase downstream from the gene(s) essential for multiplication of the bacterium.

The recombinase, when specifically induced and expressed in the mammalian host cell, catalyzes a site specific recombination event which deletes the gene(s) essential for multiplication of the bacterium flanked by the first and second attachment sites. Following this site specific recombination event the bacterium is deficient for multiplication.

The phrase "substantially no effect on the ability of the bacterium to grow by multiplication" as used herein refers to a bacterium in which colony formation is at least 75% of that of a bacterium which is otherwise identical, but which lacks the defined recombinant modifications described above. For convenience, such a bacterium which lacks the recombinantly introduced recombinase sequence and the recombinantly introduced first and second attachment sites are referred to herein as a "wild type" bacterium. In preferred embodiments, colony formation is at least 80% of that of a wild type bacterium, more preferably at least 90% of a wild type bacterium, and most preferably at least 95% of a wild type bacterium. Colony formation is determined in an in vitro colony formation assay, and is expressed as colony-forming units (CFU).

As used herein with regard to a gene (or genes), the term "essential for multiplication" refers to a gene that, when deleted, results in a bacterium in which colony formation is reduced to 1% of wild type or less, and/or in which the growth of the bacterium (measured by CFU) in host cells contained in the organism is reduced by at least 1000-fold relative to wild type. Preferably, colony formation is reduced to 0.01% of wild type or less. A bacterium in which such a gene (or genes) has been deleted is referred to herein as being "deficient for multiplication."

In the context of the present invention, deletion of a gene (or genes) essential for multiplication occurs preferentially when the bacterium is introduced into a host organism. As used herein, a deletion event occurs "preferentially in a host" if introduction of the bacterium into the host organism converts a bacterium in which colony formation is at least 75% of that of a wild type bacterium into a bacterium in which colony formation is reduced to 1% of wild type or less. Preferably, colony formation is reduced to 0.01% of wild type or less.

The term "regulatory sequences which preferentially induce expression of the recombinase in the host cell" refer to regulatory sequences which induce expression of a gene under control thereof by at least 10-fold upon introduction of the bacterium into a host organism. By way of example only, expression of genes under the actA promoter of *Listeria* is dependent upon a regulatory factor known as PrfA for transcriptional activation. Relative to broth-grown *Listeria*, gene expression under actA/PrfA regulation is induced approximately 200-fold when *Listeria* is present in host cells. Thus, in certain embodiments the regulatory sequences comprise a *Listeria monocytogenes* promoter which is PrfA-dependent. PrfA-dependent promoters may be selected from the group consisting of the inlA promoter, the inlB promoter, the inlC promoter, the hpt promoter, the hly promoter, the plcA promoter, the mpl promoter, and the actA promoter. Similar systems to induce gene expression in host organisms for other bacterial species are described hereinafter. In preferred embodiments, such preferentially induced expression increases at least 50-fold, more preferably at least 100-fold, and still more preferably at least 1000-fold, upon introduction of the bacterium into a host organism.

The term "host organism" as used herein refer to an organism in which the bacterium of interest is able to multiply in the absence of deletion of a gene (or genes) essential for multiplication as described herein. In certain embodiments, a host organism is a mammalian species, most preferably a human. Also, in certain embodiments, the bacterium is an intracellular pathogen, and the regulatory sequences preferentially induce expression of the recombinase when the bacterium is in a mammalian host cell. Preferred bacterial genuses are selected from the group consisting of *Listeria, Neisseria, Mycobacterium, Francisella, Bacillus, Salmonella, Shigella, Yersinia, Brucella, Legionella, Rickettsia*, and *Chlamydia*. This list is not meant to be limiting. Most preferably, the bacterium is a facultative intracellular bacterium such as *Listeria, Salmonella, Shigella, Francisella, Mycobacterium, Legionella, Burkholderia* and *Brucella*. In certain exemplary embodiments described hereinafter, the bacterium is *Listeria monocytogenes*, including modified such as *Listeria monocytogenes* ΔActA/ΔInlB (a *L. monocytogenes* in which the native ActA and InlB genes have been deleted or rendered functionally deleted by mutation).

As noted above, a recombinase sequence which is recombinantly introduced into a bacterium is heterologous to the bacterium. As used herein, this term refers to a recombinase which is not a normal constituent of the bacterial genome. In various embodiments, the recombinase may be selected from the group consisting of φC31 integrase, R4 integrase, TP901 integrase, φBT1 integrase, BxB1 integrase, PSA integrase, Cre recombinase, Flp recombinase, XerC recombinase, λ integrase, HK022 integrase, P22 integrase, HP1 integrase, L5 integrase, γδ recombinase, Tn3 recombinase, gin recombinase, RV integrase, SPBc integrase, TG1 integrase, φC1 integrase, MR11 integrase, φ370 integrase, φK38 integrase, Wβ integrase, and BL3 integrase. Suitable recombinase attachment sites can include recombinantly introduced attB and attP sites.

In certain embodiments, the gene(s) essential for multiplication of the bacterium comprise at least one gene involved in DNA replication. Such genes may be selected from the group consisting of ori, dnaA, dnaN, gyrA, gyrB, polC, dnaE, ftsK, ftsZ, ligA, dnaG, parC, parE, holB, dnaX, SMC, and ftsY.

As described hereinafter, a plurality of genes essential for multiplication of the bacterium are often grouped together as a single operon. In this case, the first attachment site may be preferentially recombinantly introduced upstream of a portion of the operon, and the second attachment site recombinantly introduced downstream of a portion of the operon, such that the site specific recombination event deletes a plurality of such genes in a single event. Preferably, the first attachment site is upstream of the operon, and the second attachment site is downstream of the operon. The first and second attachment sites can flank a nucleic acid sequence about 20 kb in length or less, about 10 kb in length or less, and about 6 kb in length. The term "about" in this context refers to +/−10% of a given length.

In certain embodiments, the bacterium is utilized as an expression platform for expressing one or more genes which are heterologous to the bacterium, for example for purposes of generating an immune response to the heterologous proteins expressed from those genes. In these embodiments, the bacterium can comprise within the bacterial genome an exogenous nucleic acid sequence encoding a heterologous polypeptide(s), wherein the exogenous nucleic acid sequence is operably connected to regulatory sequences which preferentially induce expression of the heterologous polypeptide when the bacterium is in a mammalian host.

In a related aspect, the invention relates to methods of deleting one or more genes in a bacterial genome which are essential for multiplication of a bacterium. These methods comprise introducing the facultatively attenuated bacterium described herein to a host organism host under conditions wherein the recombinase is expressed by the bacterium, and wherein the expressed recombinase deletes the one or more genes essential for multiplication of the bacterium by the site specific recombination event.

In yet another aspect, the present invention relates to a facultatively attenuated bacterium, or population thereof such as a bacterial culture, as described herein. Such a bacterium comprises:

(i) a nucleic acid encoding a recombinase heterologous to the bacterium, wherein the nucleic acid encoding the recombinase is operably connected to regulatory sequences which preferentially induce expression of the recombinase in the host, and (ii) a first attachment site for the recombinase upstream from the gene(s) essential for multiplication of the bacterium, and a second attachment site for the recombinase downstream from the gene(s) essential for multiplication of the bacterium, wherein the first and second attachment sites are operably linked such that the recombinase, when expressed in the mammalian host, catalyzes a site specific recombination event which deletes the gene(s) essential for multiplication of the bacterium flanked by the first and second attachment sites.

As noted above, in certain embodiments the bacterium is an intracellular pathogen, and is most preferably a facultative intracellular bacterium, and the regulatory sequences preferentially induce expression of the recombinase when the bacterium is in a mammalian host cell. A suitable bacterium is of a genus selected from the group consisting of *Listeria, Neisseria, Mycobacterium, Francisella, Bacillus, Salmonella, Shigella, Yersinia, Brucella, Legionella, Rickettsia*, and *Chlamydia*. This list is not meant to be limiting. Most preferably, the bacterium is a facultative intracellular bacterium such as *Listeria, Salmonella, Shigella, Francisella, Mycobacterium, Legionella, Burkholderia*, and *Brucella*. In certain exemplary embodiments described hereinafter, the bacterium is *Listeria monocytogenes*, including modified such as *Listeria monocytogenes* ΔActA/ΔInlB. In certain embodiments, the gene(s) essential for multiplication of the bacterium comprise at least one gene involved in DNA replication. Such genes may be selected from the group consisting of ori, dnaA, dnaN, gyrA, gyrB, polC, dnaE, ftsK, ftsZ, ligA, dnaG, parC, parE, holB, dnaX, SMC, and ftsY.

As also noted above, a recombinase sequence which is recombinantly introduced into a bacterium is heterologous to the bacterium. As used herein, this term refers to a recombinase which is not a normal constituent of the bacterial genome. In various embodiments, the recombinase may be selected from the group consisting of φC31 integrase, R4 integrase, TP901 integrase, φBT1 integrase, BxB1 integrase, PSA integrase, Cre recombinase, Flp recombinase, XerC recombinase, λ integrase, HK022 integrase, P22 integrase, HP1 integrase, L5 integrase, γδ recombinase, Tn3 recombinase, gin recombinase, RV integrase, SPBc integrase, TG1 integrase, φC1 integrase, MR11 integrase, φ370 integrase, φK38 integrase, Wβ integrase, and BL3 integrase. Suitable recombinase attachment sites can include recombinantly introduced attB and attP sites.

As described hereinafter, a plurality of genes essential for multiplication of the bacterium are often grouped together as a single operon. In this case, the first attachment site may be preferentially recombinantly introduced upstream of a portion of the operon, and the second attachment site recombinantly introduced downstream of a portion of the operon, such that the site specific recombination event deletes a plurality of such genes in a single event. Preferably, the first attachment site is upstream of the operon, and the second attachment site is downstream of the operon. The first and second attachment sites can flank a nucleic acid sequence about 20 kb in length or less, about 10 kb in length or less, about 6 kb in length, or of any length that is sufficient to inactivate multiplication of the bacterium in the host cell. The term "about" in this context refers to +/−10% of a given length.

The bacterium of the present invention may be utilized as an expression platform for expressing one or more genes which are heterologous to the bacterium, for example for purposes of generating an immune response to the heterologous proteins expressed from those genes. In these embodiments, the bacterium can comprise within the bacterial genome an exogenous nucleic acid sequence encoding a heterologous polypeptide, wherein the exogenous nucleic acid sequence is operably connected to regulatory sequences which preferentially induce expression of the heterologous polypeptide when the bacterium is in a mammalian host.

BRIEF DESCRIPTION OF THE FIGURES

FIG. 3. Deletion 1. (A) Lox recombinase sites flanking gyrase region (yaaA, recF, gyrB, gyrA); (B) Growth curve in broth culture; (C) Intracellular growth curve in DC2.4 cells.

DETAILED DESCRIPTION OF THE INVENTION

Figure 1:
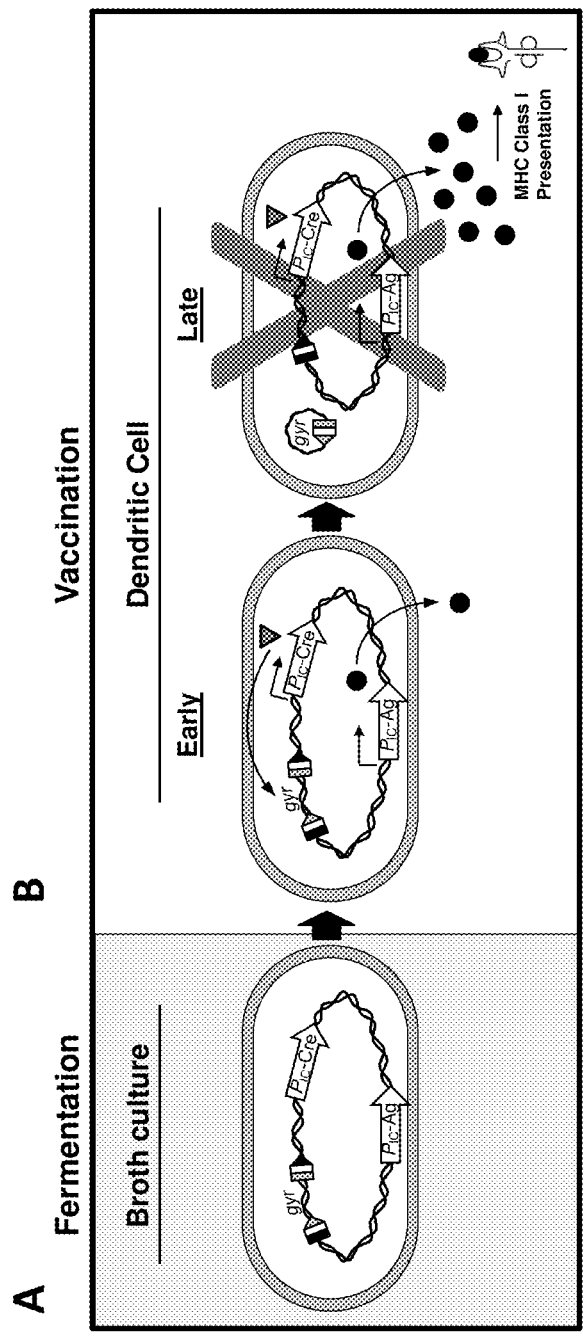
FIG. 1. Schematic representation of Lm-RIID. (A) In broth culture or fermentation, Lm-RIID do not express the recombinase, thus allowing growth and manufacturing of vaccines. (B) After vaccination, Lm-RIID enter dendritic cells where they simultaneously express the recombinase that results in bacterial death and the vaccine antigen which results in specific immunogenicity.

The present invention relates to compositions and methods for preparing and using facultatively attenuated bacterial species. The present invention can provide attenuated bacterial vaccine strains with advantageous safety profiles for use treatment or prevention of diseases having a risk-benefit profile not appropriate for live attenuated vaccines.

While described hereinafter in detail with regard to *Listeria monocytogenes*, the skilled artisan will understand that the methods and compositions described herein are generally applicable to bacterial species, and in particular to facultative intracellular bacterial species.

*Listeria monocytogenes* (Lm) is a facultative intracellular bacterium characterized by its ability to induce a profound innate immune response that leads to robust and highly functional CD4 and CD8 T cell immunity specific for vaccine-encoded Ags. Lm is a food-borne bacterium with increased pathogenicity among immune compromised individuals, including patients with cancer or other viral-induced immune deficiencies, pregnant women, the elderly and infants.

Live-attenuated recombinant Lm vaccine platforms engineered to encode a designated antigen(s) relevant to a selected targeted pathogenic agent or malignancy have formed the basis for several human clinical trials. In particular, genetically defined live-attenuated Lm ΔactAΔinlB, which is deleted of two virulence genes and is attenuated >3 logs in the mouse listeriosis model, retains its immunologic potency and has been shown to induce robust CD4 and CD8 T cell immunity in both mouse models of human disease as well as in humans, and has been shown to be safe and well-tolerated in clinical settings among patients with various solid tumor malignancies.

To prime a desired CD8 T cell response, Lm-based vaccines must retain the ability to escape from the vacuole of infected dendritic cells (DCs) in a process mediated by expression of a pore-forming cytolysin known as listeriolysin O (LLO), and desired antigens are engineered to be expressed and secreted from bacteria in the cytoplasm, where they are subsequently processed and presented on MHC class I molecules. Thus, inactivated Lm vaccines, such as those inactivated by heat (Heat-Killed Lm; HKLM) and are not metabolically active and cannot induce a desired CD8 T cell response that can effectively protect against challenge with a pathogen containing the vaccine immunogen or conferring efficacy in tumor-bearing animals. This dichotomy is well-known in the field and represents a challenge to vaccinologists developing Lm vaccine platforms that retain immunologic potency that is comparable to live-attenuated Lm vaccine platforms, yet have the safety of HKLM.

Facultatively attenuated Lm, referred to herein as Recombinase-Induced Intracellular Death (Lm-RIID), has been developed to address the need for safe and immunologically potent Lm-based vaccine platforms. Lm-RIID vaccines concurrently express the vaccine antigen of interest and induce the deletion of genes essential for bacterial viability after the Lm vaccine strain escapes into the cytosol of the host cell. Lm-RIID vaccines grow in broth culture with the same properties as live-attenuated Lm vaccines such as Lm ΔactAΔinlB based vaccines, but commit suicide once inside host cells. This is achieved by flanking essential target Lm genes with recombinase (e.g., loxP) sites, and driving expression of a sequence-specific recombinase (e.g., Cre recombinase) as well as vaccine antigen expression, from promoters that are specifically induced in the host organism, in this case in the host cytoplasm. This results in a self-limiting infection even when administered intravenously into a host animal. As described hereinafter, Lm-RIID vaccines can be derived from previously described live-attenuated Lm vaccine strains, for example Lm ΔactAΔinlB. Expression of the ActA protein is induced >200-fold with infected host mammalian cells, compared to broth culture. However, the PrfA-dependent actA promoter is NOT substantially induced in broth culture. Lm-RIID vaccines can be manufactured with the same methods used for growth of live-attenuated Lm vaccines, such as the Lm ΔactAΔinlB strain.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

1. Definitions

Abbreviations used to indicate a mutation in a gene, or a mutation in a bacterium comprising the gene, are as follows. By way of example, the abbreviation "*L. monocytogenes* ΔactA" means that part, or all, of the actA gene was deleted. The delta symbol (Δ) means deletion. An abbreviation including a superscripted minus sign (*Listeria* ActA$^-$) means that the actA gene was mutated, e.g., by way of a deletion, point mutation, or frameshift mutation, but not limited to these types of mutations.

"Administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) can encompass GM-CSF, a mutein or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

As used herein, an "analog" or "derivative" with reference to a peptide, polypeptide or protein refers to another peptide, polypeptide or protein that possesses a similar or identical function as the original peptide, polypeptide or protein, but does not necessarily comprise a similar or identical amino acid sequence or structure of the original peptide, polypeptide or protein. An analog preferably satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the original amino acid sequence (b) a proteinaceous agent encoded by a nucleotide sequence that hybridizes under stringent conditions to a nucleotide sequence encoding the original amino acid sequence; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the original amino acid sequence.

"Antigen presenting cells" (APCs) are cells of the immune system used for presenting antigen to T cells. APCs include dendritic cells, monocytes, macrophages, marginal zone Kupffer cells, microglia, Langerhans cells, T cells, and B cells. Dendritic cells occur in at least two lineages. The first lineage encompasses pre-DC1, myeloid DC1, and mature DC1. The second lineage encompasses $CD34^+$ $CD45RA^-$ early progenitor multipotent cells, $CD34^+$ $CD45RA^+$ cells, $CD34^+CD45RA^+CD4^+IL\text{-}3Ra^+pro\text{-}DC2$ cells, $CD4^+CD11c^-$ plasmacytoid pre-DC2 cells, lymphoid human DC2 plasmacytoid-derived DC2s, and mature DC2s.

"Attenuation" and "attenuated" encompasses a bacterium, virus, parasite, infectious organism, prion, tumor cell, gene in the infectious organism, and the like, that is modified to reduce toxicity to a host. The host can be a human or animal host, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicum or indicia of toxicity, the $LD_{50}$, the rate of clearance from an organ, or the competitive index (see, e.g., Auerbuch, et al. (2001) Infect. Immunity 69:5953-5957). Generally, an attenuation results an increase in the $LD_{50}$ and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

"Attenuated gene" encompasses a gene that mediates toxicity, pathology, or virulence, to a host, growth within the host, or survival within the host, where the gene is mutated in a way that mitigates, reduces, or eliminates the toxicity, pathology, or virulence. The reduction or elimination can be assessed by comparing the virulence or toxicity mediated by the mutated gene with that mediated by the non-mutated (or parent) gene. "Mutated gene" encompasses deletions, point mutations, and frameshift mutations in regulatory regions of the gene, coding regions of the gene, non-coding regions of the gene, or any combination thereof.

"Conservatively modified variants" applies to both amino acid and nucleic acid sequences. With respect to particular nucleic acid sequences, a conservatively modified variant refers to nucleic acids encoding identical amino acid sequences, or amino acid sequences that have one or more conservative substitutions. An example of a conservative substitution is the exchange of an amino acid in one of the following groups for another amino acid of the same group (U.S. Pat. No. 5,767,063 issued to Lee, et al.; Kyte and Doolittle (1982) J. Mol. Biol. 157:105-132).

(1) Hydrophobic: Norleucine, Ile, Val, Leu, Phe, Cys, Met;
(2) Neutral hydrophilic: Cys, Ser, Thr;
(3) Acidic: Asp, Glu;
(4) Basic: Asn, Gln, H is, Lys, Arg;
(5) Residues that influence chain orientation: Gly, Pro;
(6) Aromatic: Trp, Tyr, Phe; and
(7) Small amino acids: Gly, Ala, Ser.

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition.

An "extracellular fluid" encompasses, e.g., serum, plasma, blood, interstitial fluid, cerebrospinal fluid, secreted fluids, lymph, bile, sweat, fecal matter, and urine. An "extracelluar fluid" can comprise a colloid or a suspension, e.g., whole blood or coagulated blood.

The term "fragments" in the context of polypeptides include a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a larger polypeptide.

"Gene" refers to a nucleic acid sequence encoding an oligopeptide or polypeptide. The oligopeptide or polypeptide can be biologically active, antigenically active, biologically inactive, or antigenically inactive, and the like. The term gene encompasses, e.g., the sum of the open reading frames (ORFs) encoding a specific oligopeptide or polypeptide; the sum of the ORFs plus the nucleic acids encoding introns; the sum of the ORFs and the operably linked promoter(s); the sum of the ORFS and the operably linked promoter(s) and any introns; the sum of the ORFS and the operably linked promoter(s), intron(s), and promoter(s), and other regulatory elements, such as enhancer(s). In certain embodiments, "gene" encompasses any sequences required in cis for regulating expression of the gene. The term gene can also refer to a nucleic acid that encodes a peptide encompassing an antigen or an antigenically active fragment of a peptide, oligopeptide, polypeptide, or protein. The term gene does not necessarily imply that the encoded peptide or protein has any biological activity, or even that the peptide or protein is antigenically active. A nucleic acid sequence encoding a non-expressable sequence is generally considered a pseudogene. The term gene also encompasses nucleic acid sequences encoding a ribonucleic acid such as rRNA, tRNA, or a ribozyme.

"Growth" of a bacterium such as *Listeria* encompasses, without limitation, functions of bacterial physiology and genes relating to colonization, replication, increase in protein content, and/or increase in lipid content. Unless specified otherwise explicitly or by context, growth of a *Listeria* encompasses growth of the bacterium outside a host cell, and also growth inside a host cell. Growth related genes include, without implying any limitation, those that mediate energy production (e.g., glycolysis, Krebs cycle, cytochromes), anabolism and/or catabolism of amino acids, sugars, lipids, minerals, purines, and pyrimidines, nutrient transport, transcription, translation, and/or replication. In some embodiments, "growth" of a *Listeria* bacterium refers to intracellular growth of the *Listeria* bacterium, that is, growth inside a host cell such as a mammalian cell. While intracellular growth of a *Listeria* bacterium can be measured by light microscopy or colony forming unit (CFU) assays, growth is not to be limited by any technique of measurement. Biochemical parameters such as the quantity of a Listerial antigen, Listerial nucleic acid sequence, or lipid specific to the *Listeria* bacterium, can be used to assess growth. In some embodiments, a gene that mediates growth is one that specifically mediates intracellular growth. In some embodiments, a gene that specifically mediates intracellular growth encompasses, but is not limited to, a gene where inactivation of the gene reduces the rate of intracellular growth but does not detectably, substantially, or appreciably, reduce the rate of extracellular growth (e.g., growth in broth), or a gene where inactivation of the gene reduces the rate of intracellular growth to a greater extent than it reduces the rate of extracellular growth. To provide a non-limiting example, in some embodiments, a gene where inactivation reduces the rate of intracellular growth to a greater extent than extracellular growth encompasses the situation where inactivation reduces intracellular growth to less than 50% the normal or maximal value, but reduces extracellular growth to only 1-5%, 5-10%, or 10-15% the maximal value. The invention, in certain aspects, encompasses a *Listeria* attenuated in intracellular growth but not attenuated in extracellular growth, a *Listeria* not attenuated in intracellular growth and not attenuated in extracellular growth, as well as a *Listeria* not attenuated in intracellular growth but attenuated in extracellular growth.

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

"Ligand" refers to a small molecule, peptide, polypeptide, or membrane associated or membrane-bound molecule, that is an agonist or antagonist of a receptor. "Ligand" also encompasses a binding agent that is not an agonist or antagonist, and has no agonist or antagonist properties. By convention, where a ligand is membrane-bound on a first cell, the receptor usually occurs on a second cell. The second cell may have the same identity (the same name), or it may have a different identity (a different name), as the first cell. A ligand or receptor may be entirely intracellular, that is, it may reside in the cytosol, nucleus, or in some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Nucleic acid" refers to deoxyribonucleotides or ribonucleotides and polymers thereof in either single stranded, double-stranded form, or multi-stranded form. Non-limiting examples of a nucleic acid are a, e.g., cDNA, mRNA, oligonucleotide, and polynucleotide. A particular nucleic acid sequence can also implicitly encompasses "allelic variants" and "splice variants."

"Operably linked" in the context of a promoter and a nucleic acid encoding a mRNA means that the promoter can be used to initiate transcription of that nucleic acid.

The terms "percent sequence identity" and "% sequence identity" refer to the percentage of sequence similarity found by a comparison or alignment of two or more amino acid or nucleic acid sequences. Percent identity can be determined by a direct comparison of the sequence information between two molecules by aligning the sequences, counting the exact number of matches between the two aligned sequences, dividing by the length of the shorter sequence, and multiplying the result by 100. An algorithm for calculating percent identity is the Smith-Waterman homology search algorithm (see, e.g., Kann and Goldstein (2002) Proteins 48:367-376; Arslan, et al. (2001) Bioinformatics 17:327-337).

By "purified" and "isolated" is meant, when referring to a polypeptide, that the polypeptide is present in the substantial absence of the other biological macromolecules with which it is associated in nature. The term "purified" as used herein means that an identified polypeptide often accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the polypeptides present. The weights of water, buffers, salts, detergents, reductants, protease inhibitors, stabilizers (including an added protein such as albumin), and excipients, and molecules having a molecular weight of less than 1000, are generally not used in the determination of polypeptide purity. See, e.g., discussion of purity in U.S. Pat. No. 6,090,611 issued to Covacci, et al.

"Peptide" refers to a short sequence of amino acids, where the amino acids are connected to each other by peptide bonds. A peptide may occur free or bound to another moiety, such as a macromolecule, lipid, oligo- or polysaccharide, and/or a polypeptide. Where a peptide is incorporated into a polypeptide chain, the term "peptide" may still be used to refer specifically to the short sequence of amino acids. A "peptide" may be connected to another moiety by way of a peptide bond or some other type of linkage. A peptide is at least two amino acids in length and generally less than about 25 amino acids in length, where the maximal length is a function of custom or context. The terms "peptide" and "oligopeptide" may be used interchangeably.

"Protein" generally refers to the sequence of amino acids comprising a polypeptide chain. Protein may also refer to a three dimensional structure of the polypeptide. "Denatured protein" refers to a partially denatured polypeptide, having some residual three dimensional structure or, alternatively, to an essentially random three dimensional structure, i.e., totally denatured. The invention encompasses reagents of, and methods using, polypeptide variants, e.g., involving glycosylation, phosphorylation, sulfation, disulfide bond formation, deamidation, isomerization, cleavage points in signal or leader sequence processing, covalent and non-covalently bound cofactors, oxidized variants, and the like. The formation of disulfide linked proteins is described (see, e.g., Woycechowsky and Raines (2000) Curr. Opin. Chem. Biol. 4:533-539; Creighton, et al. (1995) Trends Biotechnol. 13:18-23).

"Recombinant" when used with reference, e.g., to a nucleic acid, cell, animal, virus, plasmid, vector, or the like, indicates modification by the introduction of an exogenous, non-native nucleic acid, alteration of a native nucleic acid, or by derivation in whole or in part from a recombinant nucleic acid, cell, virus, plasmid, or vector. Recombinant protein refers to a protein derived, e.g., from a recombinant nucleic acid, virus, plasmid, vector, or the like. "Recombinant bacterium" encompasses a bacterium where the genome is engineered by recombinant methods, e.g., by way of a mutation, deletion, insertion, and/or a rearrangement. "Recombinant bacterium" also encompasses a bacterium modified to include a recombinant extra-genomic nucleic acid, e.g., a plasmid or a second chromosome, or a bacterium where an existing extra-genomic nucleic acid is altered.

"Sample" refers to a sample from a human, animal, placebo, or research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

A "selectable marker" encompasses a nucleic acid that allows one to select for or against a cell that contains the selectable marker. Examples of selectable markers include, without limitation, e.g.: (1) A nucleic acid encoding a product providing resistance to an otherwise toxic compound (e.g., an antibiotic), or encoding susceptibility to an otherwise harmless compound (e.g., sucrose); (2) A nucleic acid encoding a product that is otherwise lacking in the recipient cell (e.g., tRNA genes, auxotrophic markers); (3) A nucleic acid encoding a product that suppresses an activity of a gene product; (4) A nucleic acid that encodes a product that can be readily identified (e.g., phenotypic markers such as beta-galactosidase, green fluorescent protein (GFP), cell surface proteins, an epitope tag, a FLAG tag); (5) A nucleic acid that can be identified by hybridization techniques, for example, PCR or molecular beacons.

"Specifically" or "selectively" binds, when referring to a ligand/receptor, nucleic acid/complementary nucleic acid, antibody/antigen, or other binding pair (e.g., a cytokine to a cytokine receptor) indicates a binding reaction which is determinative of the presence of the protein in a heterogeneous population of proteins and other biologics. Thus, under designated conditions, a specified ligand binds to a particular receptor and does not bind in a significant amount to other proteins present in the sample. Specific binding can also mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with any other binding compound.

In a typical embodiment an antibody will have an affinity that is greater than about $10^9$ liters/mol, as determined, e.g., by Scatchard analysis (Munsen, et al. (1980) Analyt. Biochem. 107:220-239). It is recognized by the skilled artisan that some binding compounds can specifically bind to more than one target, e.g., an antibody specifically binds to its antigen, to lectins by way of the antibody's oligosaccharide, and/or to an Fc receptor by way of the antibody's Fc region.

"Spread" of a bacterium encompasses "cell to cell spread," that is, transmission of the bacterium from a first host cell to a second host cell, as mediated, for example, by a vesicle. Functions relating to spread include, but are not limited to, e.g., formation of an actin tail, formation of a pseudopod-like extension, and formation of a double-membraned vacuole.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology.

The "target site" of a recombinase is the nucleic acid sequence or region that is recognized, bound, and/or acted upon by the recombinase (see, e.g., U.S. Pat. No. 6,379,943 issued to Graham, et al.; Smith and Thorpe (2002) Mol. Microbiol. 44:299-307; Groth and Calos (2004) J. Mol. Biol. 335:667-678; Nunes-Duby, et al. (1998) Nucleic Acids Res. 26:391-406).

"Therapeutically effective amount" is defined as an amount of a reagent or pharmaceutical composition that is sufficient to induce a desired immune response specific for encoded heterologous antigens, show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual (see, e.g., U.S. Pat. No. 5,888,530 issued to Netti, et al.).

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, and/or prolonging survival.

"Vaccine" encompasses preventative vaccines. Vaccine also encompasses therapeutic vaccines, e.g., a vaccine administered to a mammal that comprises a condition or disorder associated with the antigen or epitope provided by the vaccine. A number of bacterial species have been developed for use as vaccines and can be used in the present invention, including, but not limited to, *Shigella flexneri, Escherichia coli, Listeria monocytogenes, Yersinia enterocolitica, Salmonella typhimurium, Salmonella typhi* or *mycobacterium* species. This list is not meant to be limiting.

See, e.g., WO04/006837; WO07/103,225; and WO07/117,371, each of which is hereby incorporated by reference in its entirety, including all tables, figures, and claims. The bacterial vector used in the vaccine composition may be a facultative, intracellular bacterial vector. The bacterium may be used to deliver a polypeptide described herein to antigen-presenting cells in the host organism. As described herein, L. monocytogenes provides a preferred vaccine platform for expression of the antigens of the present invention.

2. Targeting Essential Genes for Facultative Deletion

Bacteria engineered for Recombinase-Induced Intracellular Death (RIID) are programmed to "commit suicide" by linking expression of a recombinantly introduced recombinase gene to a promoter that is facultatively expressed when the bacterium is in a host organism. By way of example below, expression of the recombinase can be made facultative in Listeria using a PrfA-dependent promoter which may be selected from the inlA promoter, the inlB promoter, the inlC promoter, the hpt promoter, the hly promoter, the plcA promoter, the mpl promoter, and the actA promoter. PrfA is a transcription factor activated intracellularly which induces expression of linked genes in appropriately engineered vaccine strains.

The sequence of L. monocytogenes PrfA is as follows (SEQ ID NO: 1):
MNAQAEEFKK YLETNGIKPK QFHKKELIFN QWD-PQEYCIF LYDGITKLTS 50
ISENGTIMNL QYYKGAFVIM SGFIDTETSV GYYNLE-VISE QATAYVIKIN 100
ELKELLSKNL THFFYVFQTL QKQVSYSLAK FNDF-SINGKL GSICGQLLIL 150
TYVYGKETPD GIKITLDNLT MQELGYSSGI AHSSAVSRII SKLKQEKVIV 200
YKNSCFYVQN LDYLKRYAPK LDEWFYLACP ATWG-KLN 237

As noted above, in the following examples expression of the actA gene is responsive to PrfA, and the actA promoter is a PrfA responsive regulatory element. The actA promoter is a suitable promoter for facultative high-level expression of recombinase genes, as ActA is the most abundantly expressed Listeria protein and its expression is induced >200-fold within infected cells as compared to in vitro culture conditions.

Other regulatory systems which may be used in a manner similar to that of Listeria PrfA include the following:

| genus | species | regulator |
| --- | --- | --- |
| Mycobacterium | tuberculosis | PhoP, ArsR |
| Francisella | tularensis | MigR |
| Salmonella | enterica | SlyA, SsrB |
| Shigella | flexneri | VirB |
| Burkholderia | cenocepacia | ShvR |
| Brucella | melitensis | BlxR |
| Legionella | pneumophila | PmrA |
| Yersinia | pestis, enterocolitica | RovA |
| Bacillus | anthracis | AtxA |
| Staphylococcus | aureus | SarA |

In the following examples, expression of Cre recombinase is linked to the actA promoter for expression in Listeria. In alternatives, recombinases such as φC31 integrase, R4 integrase, TP901 integrase, φBT1 integrase, BxB1 integrase, PSA integrase, Cre recombinase, Flp recombinase, XerC recombinase, λ integrase, HK022 integrase, P22 integrase, HP1 integrase, L5 integrase, γδ recombinase, Tn3 recombinase, gin recombinase, RV integrase, SPBc integrase, TG1 integrase, φC1 integrase, MR11 integrase, φ370 integrase, φK38 integrase, Wβ integrase, and BL3 integrase may find use in the present invention in a manner similar to that shown below for Cre recombinase.

Upon expression, Cre excises a bacterial gene required for viability that has been targeted for deletion by the recombinant introduction of flanking recombinase binding sites (e.g., loxP). Advantageously, mutant recombinase sites such as lox66 and lox71 mutant lox P sites may be utilized. Unlike native loxP, lox66 and lox71 sites which are joined following excision of the targeted gene(s) cannot be used subsequently as a template for Cre-mediated recombination, thus driving the equilibrium of excision to completion.

Targeting deletion genes essential for DNA replication (e.g., gyrA, gyrB) results in bacterial cell death in infected cells, as compared to its isogenic parent Listeria strain. However, because the actA promoter is not induced during fermentation, growth of RIID Lm in bacterial growth media is indistinguishable from the parent strain. Expression of Lm-encoded antigens can also be induced in the infected APC using a PrfA-dependent promoter such as ActA, where synthesized antigens are secreted from the listerial bacterium into the cytosol through linkage with a bacterial signal peptide/chaperone and then processed and presented via the MHC class I pathway. Although RIID Lm strain is programmed for death post-infection of APCs, the vaccine still elicits potent CD8 T cell responses that are comparable to vaccination with an isogenic live-attenuated Lm vaccine strain.

The following is a non-limiting list of exemplary genes involved in DNA replication which may be targeted for excision in the RIID approach.
ori (origin of replication)
dnaA (replication initiation)
dnaN (DNA polymerase III, beta subunit)
gyrA (DNA gyrase, subunit A)
gyrB (DNA gyrase, subunit B)
polC (DNA polymerase III, alpha subunit)
dnaE (DNA polymerase III, alpha subunit)
ftsK (DNA translocase, chromosome separation)
ftsZ (tubulin-like, septation)
ligA (DNA ligase)
dnaG (DNA primase)
parC (topo IV subunit)
parE (topo IV subunit)
holB (DNA polymerase III, delta subunit)
dnaX (DNA polymerase III, gamma and tau subunits)
SMC (chromosome segregation)

Preferred but non-limiting examples of genes to target for deletion include those that are involved in replication and bacterial cell division such as polC, dnaE, ftsK, ftsZ, ligA, dnaG, parC, parE, holB, dnaX, SMC, and ftsY. There are additional gene targets that are essential for the multiplication of Listeria that may be targeted for intracellular excision as an alternative, or in addition to, genes involved in DNA replication. Since Lm RIID strains have utility as a vaccine platform, in which Ag expression de novo is required for vaccine potency (Brockstedt et. al., 2005), one must consider the impact of the excised gene(s) on antigen expression/secretion to select gene targets. In a preferred embodiment, genes encoding proteins involved in RNA transcription and protein synthesis should be avoided because of a potential decrease of immunologic potency, which may not be desired for particular uses. Other preferred non-limiting examples include targeting bacterial genes affecting virulence, such as hly and dacA. It will be clear to the skilled artisan that any gene targeted for deletion in the cytosol of the infected host cell can be accomplished by the methods described herein, accordingly: First, the inter-genic regions upstream and downstream of the essential gene(s) to be deleted is identified; second PCR primers that include the desired loxP variants are designed; third, the corresponding allelic exchange vectors to insert the lox sites in the non-essential/inter-genic space are constructed; and, fourth, the lox sites are sequentially inserted into the *Listeria* vaccine strain by allelic exchange. Alternatively, it will be apparent to the skilled artisan that if the gene to be targeted for deletion is small, than both lox sites can be added with a single allelic exchange step. In still a further embodiment, the PactA-Cre cassette for induction of Cre recombinase expression in the cytosol of the infected cell can be introduced at alternate locations that are either amenable to site-specific integration (e.g. comK using pPL1) or any chromosomal location that is amenable to insertion using allelic exchange methodology. In yet another embodiment, PrfA-dependent promoters other than actA can be used for the cytosolic induced expression of Cre recombinase; inlC is a non-limiting example of an alternative promoter.

As an alternative to the Cre/lox strategy discussed above, genes essential for the multiplication of *Listeria* that can also be targeted for intracellular excision with FLP recombinase and frt sites. First, the inter-genic regions upstream and downstream of the essential gene(s) to be deleted is identified; second PCR primers that include the desired frt sites are designed; third, the corresponding allelic exchange vectors to insert the frt sites in the non-essential/inter-genic space are constructed; and, fourth, the frt sites are sequentially inserted into the *Listeria* vaccine strain by allelic exchange. Alternatively, it will be apparent to the skilled artisan that if the gene to be targeted for deletion is small, than both frt sites can be added with a single allelic exchange step. In still a further embodiment, the PactA-FLP cassette for induction of FLP recombinase expression in the cytosol of the infected cell can be introduced at alternate locations that are either amenable to site-specific integration (e.g. comK using pPL1) or any chromosomal location that is amenable to insertion using allelic exchange methodology.

4. Antigenic Constructs

Target Antigens

A preferred feature of the RIID bacteria described herein when used as a vaccine platform is the ability to initiate both the innate immune response as well as an antigen-specific T cell response against the recombinantly expressed antigen(s). For example, *L. monocytogenes* expressing the antigen(s) described herein can induce Type 1 interferon (IFN-α/β) and a cascade of co-regulated chemokine and cytokine protein which shape the nature of the vaccine-induce immune response. In response to this immune stimulation, NK cells and antigen presenting cells (APCs) are recruited to the liver following intravenous vaccination routes, or, alternatively to the vaccination site following other routes of vaccination, for example, by intramuscular, subcutaneous, or intradermal immunization routes. In certain embodiments, the vaccine platform of the present invention induces an increase at 24 hours following delivery of the vaccine platform to the subject in the serum concentration of one or more, and preferably all, cytokines and chemokines selected from the group consisting of IL-12p70, IFN-γ, IL-6, TNF α, and MCP-1; and induces a CD4+ and/or CD8+ antigen-specific T cell response against one or more antigens expressed by the vaccine platform. In other embodiments, the vaccine platform of the present invention also induces the maturation of resident immature liver NK cells as demonstrated by the upregulation of activation markers such as DX5, CD11b, and CD43 in a mouse model system, or by NK cell-mediated cytolytic activity measured using $^{51}$Cr-labeled YAC-1 cells that were used as target cells.

The ability of *L. monocytogenes* to serve as a vaccine vector has been reviewed in Wesikirch, et al., *Immunol. Rev.* 158:159-169 (1997). A number of desirable features of the natural biology of *L. monocytogenes* make it an attractive platform for application to a therapeutic vaccine. The central rationale is that the intracellular lifecycle of *L. monocytogenes* enables effective stimulation of CD4+ and CD8+ T cell immunity. Multiple pathogen associated molecular pattern (PAMP) receptors including TLRs (TLR2, TLR5, TLR9) nucleotide-binding oligomerization domains (NOD), and Stimulator of Interferon Genes (STING) are triggered in response to interaction with *L. monocytogenes* macromolecules upon infection, resulting in the pan-activation of innate immune effectors and release of Th-1 polarizing cytokines, exerting a profound impact on the development of a CD4+ and CD8+ T cell response against the expressed antigens.

Strains of *L. monocytogenes* have recently been developed as effective intracellular delivery vehicles of heterologous proteins providing delivery of antigens to the immune system to induce an immune response to clinical conditions that do not permit injection of the disease-causing agent, such as cancer and HIV. See, e.g., U.S. Pat. No. 6,051,237; Gunn et al., *J. Immunol.,* 167:6471-6479 (2001); Liau, et al., *Cancer Research,* 62: 2287-2293 (2002); U.S. Pat. No. 6,099,848; WO 99/25376; WO 96/14087; and U.S. Pat. No. 5,830,702), each of which is hereby incorporated by reference in its entirety, including all tables, figures, and claims. A recombinant *L. monocytogenes* vaccine expressing an lymphocytic choriomeningitis virus (LCMV) antigen has also been shown to induce protective cell-mediated immunity to the antigen (Shen et al., Proc. Natl. Acad. Sci. USA, 92: 3987-3991 (1995).

In certain embodiments, the *L. monocytogenes* used in the vaccine compositions of the present invention is RIID strain which further comprises an attenuating mutation in actA and/or inlB, and preferably a deletion of all or a portion of actA and inlB (referred to herein as "Lm ΔactA/ΔinlB"), and contains recombinant DNA encoding for the expression of the one or more antigen(s) of interest. The antigen(s) are preferably under the control of bacterial expression sequences and are stably integrated into the *L. monocytogenes* genome.

The invention also contemplates a *Listeria* attenuated in at least one regulatory factor, e.g., a promoter or a transcription factor. The following concerns promoters. ActA expression is regulated by two different promoters (Vazwuez-Boland, et al. (1992) Infect. Immun. 60:219-230). Together, InlA and InlB expression is regulated by five promoters (Lingnau, et al. (1995) Infect. Immun. 63:3896-3903). The transcription factor prfA is required for transcription of a number of *L. monocytogenes* genes, e.g., hly, plcA, ActA, mpl, prfA, and iap. PrfA's regulatory properties are mediated by, e.g., the PrfA-dependent promoter (PinlC) and the PrfA-box. The present invention, in certain embodiments, provides a nucleic acid encoding inactivated, mutated, or deleted in at least one of ActA promoter, inlB promoter, PrfA, PinlC, PrfA box, and the like (see, e.g., Lalic Mullthaler, et al. (2001) Mol. Microbiol. 42:111-120; Shetron-Rama, et al. (2003) Mol. Microbiol. 48:1537-1551; Luo, et al. (2004) Mol. Microbiol. 52:39-52). PrfA can be made constitutively active by a Gly145Ser mutation, Gly155Ser mutation, or Glu77Lys mutation (see, e.g., Mueller and Freitag (2005) Infect. Immun. 73:1917-1926; Wong and Freitag (2004) J. Bacteriol. 186:6265-6276; Ripio, et al. (1997) J. Bacteriol. 179:1533-1540).

Examples of target antigens that may find use in the invention are listed in the following table. The target antigen may also be a fragment or fusion polypeptide comprising an immunologically active portion of the antigens listed in the table. This list is not meant to be limiting.

TABLE 1

Antigens.

| Antigen | Reference |
|---|---|
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein A (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. |
| MAGE-A1, MAGE-A2; MAGE-A3; | Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |

TABLE 1-continued

Antigens.

| Antigen | Reference |
|---|---|
| MAGE-A4; MAGE-A6; MAGE-A9; MAGE-A10; MAGE-A12; GAGE-3/6; NT-SAR-35; BAGE; CA125. | |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |

TABLE 1-continued

Antigens.

| Antigen | Reference |
|---|---|
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, e g., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; |

TABLE 1-continued

| Antigens. | |
|---|---|
| Antigen | Reference |
| | Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published Pat. Appl. No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See, e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |
| *Francisella tularensis* antigens | |
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of *F. tularensis* include, e.g., 80 antigens, including 10 kDa and 60 kDa chaperonins (Havlasova, et al. (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |
| Malarial antigens | |
| Circumsporozoite protein (CSP); SSP2; HEP17; Exp-1 orthologs found in P. falciparum; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A`13; AJ494905; AJ490565). |
| Viruses and viral antigens | |

TABLE 1-continued

Antigens.

| Antigen | Reference |
| --- | --- |
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g. NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and Toroviruses. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |
| Rubella virus. | GenBank Acc. Nos. NC_001545; AF435866. |
| Mumps virus, including the genotypes A, C, D, G, H, and I. | See, e.g., Orvell, etal. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926: X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC_003899; AY722102); Western equine encephalitis (NC_003908). |

TABLE 1-continued

Antigens.

| Antigen | Reference |
|---|---|
| encephalitis (WEE), St. Louis encephalitis, Murray Valley (Australian) encephalitis, Japanese encephalitis, and tick-born encephalitis. | |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virol. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43: 425-430; Roner, et al. (1995) Proc. Natl. Acad. Sci. USA 92: 12362-12366; Kedl, et al. (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC_001608). Ebola virus (see, e.g., GenBank Acc. Nos. NC_006432; AY769362; NC_002549; AF272001; AF086833). |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviridae, Flaviviridae, Bunyaviridae, Reoviridae, | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |

TABLE 1-continued

Antigens.

| Antigen | Reference |
|---|---|
| Rhabdoviridae, Orthomyxoviridae, and the like. | |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(. Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV): H1N1 influenza A and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wentworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957; human rotavirus A strain major inner capsid protein (see, e.g., GenBank Acc. No. AY601554). |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |

TABLE 1-continued

Antigens.

| Antigen | Reference |
|---|---|
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis, Streptococcus pyogenes* (Group A Strep), *Streptococcus agalactia* (Group B Strep), *Streptococcus pneumonia, Staphylococcus aureus, Escherichia coli, Haemophilus influenzae, Neisseria meningitidis, Neisseria gonorrheae, Vibrio cholerae, Salmonella* species (including *typhi, typhimurium*), enterica (including *Helicobactor pylori Shigella flexneri* and other Group D *shigella* species), *Burkholderia mallei, Burkholderia pseudomallei, Klebsiella pneumonia, Clostridium* species (including *C. difficile*), *Vibrio parahaemolyticus* and *V. vulnificus*. This list is not meant to be limiting.

In certain embodiments, antigen sequence(s) may be expressed as a single polypeptide fused to an amino-terminal portion of the *L. monocytogenes* ActA protein which permits expression and secretion of a fusion protein from the bacterium within the vaccinated host. In these embodiments, the antigenic construct may be a polynucleotide comprising a promoter operably linked to a nucleic acid sequence encoding a fusion protein, wherein the fusion protein comprises (a) modified ActA and (b) one or more antigenic epitopes to be expressed as a fusion protein following the modified ActA sequence.

By "modified ActA" is meant a contiguous portion of the *L. monocytogenes* ActA protein which comprises at least the ActA signal sequence, but does not comprise the entirety of the ActA sequence, or that has at least about 80% sequence identity, at least about 85% sequence identity, at least about 90% sequence identity, at least about 95% sequence identity, or at least about 98% sequence identity to such an ActA sequence. The ActA signal sequence is MGLNRFMRAM-MVVFITANCITINPDIIFA (SEQ ID NO: 2). In some embodiments, the promoter is ActA promoter from WO07/103,225; and WO07/117,371, each of which is incorporated by reference in its entirety herein.

By way of example, the modified ActA may comprise at least the first 59 amino acids of ActA, or a sequence having at least about 80% sequence identity, at least about 85% sequence identity, at least about 90% sequence identity, at least about 95% sequence identity, or at least about 98% sequence identity to at least the first 59 amino acids of ActA. In some embodiments, the modified ActA comprises at least the first 100 amino acids of ActA, or a sequence having at least about 80% sequence identity, at least about 85% sequence identity, at least about 90% sequence identity, at least about 95% sequence identity, or at least about 98% sequence identity to the first 100 amino acids of ActA. In other words, in some embodiments, the modified ActA sequence corresponds to an N-terminal fragment of ActA (including the ActA signal sequence) that is truncated at residue 100 or thereafter.

ActA-N100 has the following sequence (SEQ ID NO: 3):
VGLNRFMRAM MVVFITANCI TINPDIIFAA
TDSEDSSLNT DEWEEEKTEE50
QPSEVNTGPR YETAREVSSR DIEELEKSNK
VKNTNKADLI AMLKAKAEKG 100

In this sequence, the first residue is depicted as a valine; the polypeptide is synthesized by *Listeria* with a methionine in this position. Thus, ActA-N100 may also have the following sequence (SEQ ID NO:4):
MGLNRFMRAM MVVFITANCI TINPDIIFAA
TDSEDSSLNT DEWEEEKTEE 50
QPSEVNTGPR YETAREVSSR DIEELEKSNK
VKNTNKADLI AMLKAKAEKG 100

ActA-N100 may also comprise one or more additional residues lying between the C-terminal residue of the modified ActA and the antigen sequence. In the following sequences, ActA-N100 is extended by two residues added by inclusion of a BamH1 site (SEQ ID NO: 5):
VGLNRFMRAM MVVFITANCI TINPDIIFAA
TDSEDSSLNT DEWEEEKTEE50
QPSEVNTGPR YETAREVSSR DIEELEKSNK
VKNTNKADLI AMLKAKAEKG 100
GS
which when synthesized with a first residue methionine has the sequence (SEQ ID NO: 6):
MGLNRFMRAM MVVFITANCI TINPDIIFAA
TDSEDSSLNT DEWEEEKTEE 50
QPSEVNTGPR YETAREVSSR DIEELEKSNK
VKNTNKADLI AMLKAKAEKG 100
GS.

As sequences encoded by one organism are not necessarily codon optimized for optimal expression in a chosen vaccine platform bacterial strain, the present invention also provides nucleic acids that are altered by codon optimized for expressing by a bacterium such as *L. monocytogenes*.

In various embodiments, at least one percent of any non-optimal codons are changed to provide optimal codons, more normally at least five percent are changed, most normally at least ten percent are changed, often at least 20% are changed, more often at least 30% are changed, most often at least 40%, usually at least 50% are changed, more usually at least 60% are changed, most usually at least 70% are changed, optimally at least 80% are changed, more optimally at least 90% are changed, most optimally at least 95% are changed, and conventionally 100% of any non-optimal codons are codon-optimized for *Listeria* expression (Table 2).

TABLE 2

| Optimal codons for expression in *Listeria*. | | | | | | | | | | |
|---|---|---|---|---|---|---|---|---|---|---|
| Amino Acid | A | R | N | D | C | Q | E | G | H | I |
| Optimal *Listeria* codon | GCA | CGU | AAU | GAU | UGU | CAA | GAA | GGU | CAU | AUU |
| Amino Acid | L | K | M | F | P | S | T | W | Y | V |
| Optimal *Listeria* codon | UUA | AAA | AUG | UUU | CCA | AGU | ACA | UGG | UAU | GUU |

The invention supplies a number of *Listeria* species and strains for making or engineering an attenuated bacterium of the present invention. The *Listeria* of the present invention is not to be limited by the species and strains disclosed in Table 3.

TABLE 3

Strains of *Listeria* suitable for use in the present invention, e.g., as a vaccine or as a source of nucleic acids.

| Strain | Reference |
|---|---|
| *L. monocytogenes* 10403S wild type. | Bishop and Hinrichs (1987) J. Immunol. 139: 2005-2009; Lauer, et al. (2002) J. Bact. 184: 4177-4186. |
| *L. monocytogenes* DP-L4056 (phage cured). The prophage-cured 10403S strain is designated DP-L4056. | Lauer, et al. (2002) J. Bact. 184: 4177-4186. |
| *L. monocytogenes* DP-L4027, which is DP-L2161, phage cured, deleted in hly gene. | Lauer, et al. (2002) J. Bact. 184: 4177-4186; Jones and Portnoy (1994) Infect. Immunity 65: 5608-5613. |
| *L. monocytogenes* DP-L4029, which is DP-L3078, phage cured, deleted in ActA. | Lauer, et al. (2002) J. Bact. 184: 4177-4186; Skoble, et al. (2000) J. Cell Biol. 150: 527-538. |
| *L. monocytogenes* DP-L4042 (delta PEST) | Brockstedt, et al. (2004) Proc. Natl. Acad. Sci. USA 101: 13832-13837; supporting information. |
| *L. monocytogenes* DP-L4097 (LLO-S44A). | Brockstedt, et al. (2004) Proc. Natl. Acad. Sci. USA 101: 13832-13837; supporting information. |
| *L. monocytogenes* DP-L4364 (delta lplA; lipoate protein ligase). | Brockstedt, et al. (2004) Proc. Natl. Acad. Sci. USA 101: 13832-13837; supporting information. |
| *L. monocytogenes* DP-L4405 (delta inlA). | Brockstedt, et al. (2004) Proc. Natl. Acad. Sci. USA 101: 13832-13837; supporting information. |
| *L. monocytogenes* DP-L4406 (delta inlB). | Brockstedt, et al. (2004) Proc. Natl. Acad. Sci. USA 101: 13832-13837; supporting information. |
| L. monocytogenes CS-L0001 (delta ActA-delta inlB). | Brockstedt, et al. (2004) Proc. Natl. Acad. Sci. USA 101: 13832-13837; supporting information. |
| L. monocytogenes CS-L0002 (delta ActA-delta lplA). | Brockstedt, et al. (2004) Proc. Natl. Acad. Sci. USA 101: 13832-13837; supporting information. |
| L. monocytogenes CS-L0003 (L461T-delta lplA). | Brockstedt, et al. (2004) Proc. Natl. Acad. Sci. USA 101: 13832-13837; supporting information. |
| *L. monocytogenes* DP-L4038 (delta ActA-LLO L461T). | Brockstedt, et al. (2004) Proc. Natl. Acad. Sci. USA 101: 13832-13837; supporting information. |
| *L. monocytogenes* DP-L4384 (S44A-LLO L461T). | Brockstedt, et al. (2004) Proc. Natl. Acad. Sci. USA 101: 13832-13837; supporting information. |
| *L. monocytogenes*. Mutation in lipoate protein ligase (LplA1). | O'Riordan, et al. (2003) Science 302: 462-464. |
| *L. monocytogenes* DP-L4017 (10403S hly (L461T) point mutation in hemolysin gene. | U.S. Provisional Pat. Appl. Ser. No. 60/490,089 filed Jul. 24, 2003. |
| *L. monocytogenes* EGD. | GenBank Acc. No. AL591824. |
| *L. monocytogenes* EGD-e. | GenBank Acc. No. NC_003210. ATCC Acc. No. BAA-679. |
| *L. monocytogenes* strain EGD, complete genome, segment 3/12 | GenBank Acc. No. AL591975 |
| *L. monocytogenes*. | ATCC Nos. 13932; 15313; 19111-19120; 43248-43251; 51772-51782. |
| *L. monocytogenes* DP-L4029 deleted in uvrAB. | U.S. Provisional Pat. Appl. Ser. No. 60/541,515 filed Feb. 2, 2004; U.S. Provisional Pat. Appl. Ser. No. 60/490,080 filed Jul. 24, 2003. |
| *L. monocytogenes* DP-L4029 deleted in uvrAB treated with a psoralen. | U.S. Provisional Pat. Appl. Ser. No. 60/541,515 filed Feb. 2, 2004. |
| *L. monocytogenes* Delta actA delta inlB delta uvrAB | Brockstedt (2005) Nature Medicine and KBMA patent |
| *L. monocytogenes* Delta actA delta inlB delta uvrAB treated with psoralen | Brockstedt (2005) Nature Medicine and KBMA patent |
| *L. monocytogenes* Delta actA delta inlB delta uvrAB prfA(G155S) | Lauer et al, (2008) Infect. Immun. And WO 2009/143085 |
| *L. monocytogenes* Delta actA delta inlB delta uvrAB prfA(G155S) treated with psoralen | Lauer et al, (2008) Infect. Immun. And WO 2009/143085 |
| *L. monocytogenes* ActA-/inlB- double mutant. | Deposited with ATCC on Oct. 3, 2003. Acc. No. PTA-5562. |
| *L. monocytogenes* lplA mutant or hly mutant. | U.S. Pat. Applic. No. 20040013690 of Portnoy, et al. |
| *L. monocytogenes* DAL/DAT double mutant. | U.S. Pat. Applic. No. 20050048081 of Frankel and Portnoy. |
| *L. monocytogenes* str. 4b F2365. | GenBank Acc. No. NC_002973. |
| Listeria ivanovii | ATCC No. 49954 |
| Listeria innocua Clip11262. | GenBank Acc. No. NC_003212; AL592022. |
| Listeria innocua, a naturally occurring hemolytic strain containing the PrfA-regulated | Johnson, et al. (2004) Appl. Environ. Microbiol. 70: 4256-4266. |

TABLE 3-continued

Strains of *Listeria* suitable for use in the present invention, e.g., as a vaccine or as a source of nucleic acids.

| | |
|---|---|
| virulence gene cluster. | |
| *Listeria seeligeri*. | Howard, et al. (1992) Appl. Eviron. Microbiol. 58: 709-712. |
| *Listeria innocua* with *L. monocytogenes* pathogenicity island genes. | Johnson, et al. (2004) Appl. Environ. Microbiol. 70: 4256-4266. |
| *Listeria innocua* with *L. monocytogenes* internalin A gene, e.g., as a plasmid or as a genomic nucleic acid. | See, e.g., Lingnau, et al. (1995) Infection Immunity 63: 3896-3903; Gaillard, et al. (1991) Cell 65: 1127-1141). |

The present invention encompasses reagents and methods that comprise the above *Listerial* strains, as well as these strains that are modified, e.g., by a plasmid and/or by genomic integration, to contain a nucleic acid encoding one of, or any combination of, the following genes: hly (LLO; listeriolysin); iap (p60); inlA; inlB; inlC; dal (alanine racemase); daaA (dat; D-amino acid aminotransferase); plcA; plcB; ActA; or any nucleic acid that mediates growth, spread, breakdown of a single walled vesicle, breakdown of a double walled vesicle, binding to a host cell, uptake by a host cell. The present invention is not to be limited by the particular strains disclosed above.

4. Therapeutic Compositions

The vaccine compositions described herein can be administered to a host, either alone or in combination with a pharmaceutically acceptable excipient, in an amount sufficient to induce an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. The vaccines of the present invention can be stored, e.g., frozen, lyophilized, as a suspension, as a cell paste, or complexed with a solid matrix or gel matrix.

In certain embodiments, after the subject has been administered an effective dose of a first vaccine to prime the immune response, a second vaccine is administered. This is referred to in the art as a "prime-boost" regimen. In such a regimen, the compositions and methods of the present invention may be used as the "prime" delivery, as the "boost" delivery, or as both a "prime" and a "boost." Any number of "boost" immunizations can be delivered in order to maintain the magnitude or effectiveness of a vaccine-induced immune response.

As an example, a first vaccine comprised of killed but metabolically active *Listeria* that encodes and expresses the antigen polypeptide(s) may be delivered as the "prime," and a second vaccine comprised of attenuated (live or killed but metabolically active) *Listeria* that encodes the antigen polypeptide(s) may be delivered as the "boost." It should be understood, however, that each of the prime and boost need not utilize the methods and compositions of the present invention. Rather, the present invention contemplates the use of other vaccine modalities together with the bacterial vaccine methods and compositions of the present invention. The following are examples of suitable mixed prime-boost regimens: a DNA (e.g., plasmid) vaccine prime/bacterial vaccine boost; a viral vaccine prime/bacterial vaccine boost; a protein vaccine prime/bacterial vaccine boost; a DNA prime/bacterial vaccine boost plus protein vaccine boost; a bacterial vaccine prime/DNA vaccine boost; a bacterial vaccine prime/viral vaccine boost; a bacterial vaccine prime/protein vaccine boost; a bacterial vaccine prime/bacterial vaccine boost plus protein vaccine boost; etc. This list is not meant to be limiting.

The prime vaccine and boost vaccine may be administered by the same route or by different routes. The term "different routes" encompasses, but is not limited to, different sites on the body, for example, a site that is oral, non-oral, enteral, parenteral, rectal, intranode (lymph node), intravenous, arterial, subcutaneous, intradermal, intramuscular, intratumor, peritumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine or vaccines in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

In certain embodiments, administration of the boost vaccination can be initiated at about 5 days after the prime vaccination is initiated; about 10 days after the prime vaccination is initiated; about 15 days; about 20 days; about 25 days; about 30 days; about 35 days; about 40 days; about 45 days; about 50 days; about 55 days; about 60 days; about 65 days; about 70 days; about 75 days; about 80 days; about 6 months, and about 1 year after administration of the prime vaccination is initiated. Preferably one or both of the prime and boost vaccination comprises delivery of a composition of the present invention.

A "pharmaceutically acceptable excipient" or "diagnostically acceptable excipient" includes but is not limited to, sterile distilled water, saline, phosphate buffered solutions, amino acid based buffers, or bicarbonate buffered solutions. An excipient selected and the amount of excipient used will depend upon the mode of administration. Administration may be oral, intravenous, subcutaneous, dermal, intradermal, intramuscular, mucosal, parenteral, intraorgan, intralesional, intranasal, inhalation, intraocular, intramuscular, intravascular, intranodal, by scarification, rectal, intraperitoneal, or any one or combination of a variety of well-known routes of administration. The administration can comprise an injection, infusion, or a combination thereof.

Administration of the vaccine of the present invention by a non-oral route can avoid tolerance. Methods are known in the art for administration intravenously, subcutaneously, intradermally, intramuscularly, intraperitoneally, orally, mucosally, by way of the urinary tract, by way of a genital tract, by way of the gastrointestinal tract, or by inhalation.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The vaccines of the present invention can be administered in a dose, or dosages, where each dose comprises at least 100 bacterial cells/kg body weight or more; in certain embodiments 1000 bacterial cells/kg body weight or more; normally at least 10,000 cells; more normally at least 100,000 cells; most normally at least 1 million cells; often at least 10 million cells; more often at least 100 million cells; typically at least 1 billion cells; usually at least 10 billion cells; conventionally at least 100 billion cells; and sometimes at least 1 trillion cells/kg body weight. The present invention provides the above doses where the units of bacterial administration is colony forming units (CFU), the equivalent of CFU prior to psoralen treatment, or where the units are number of bacterial cells.

The vaccines of the present invention can be administered in a dose, or dosages, where each dose comprises between $10^7$ and $10^8$ bacteria per 70 kg body weight (or per 1.7 square meters surface area; or per 1.5 kg liver weight); $2\times10^7$ and $2\times10^8$ bacteria per 70 kg body weight (or per 1.7 square meters surface area; or per 1.5 kg liver weight); $5\times10^7$ and $5\times10^8$ bacteria per 70 kg body weight (or per 1.7 square meters surface area; or per 1.5 kg liver weight); $10^8$ and $10^9$ bacteria per 70 kg body weight (or per 1.7 square meters surface area; or per 1.5 kg liver weight); between $2.0\times10^8$ and $2.0\times10^9$ bacteria per 70 kg (or per 1.7 square meters surface area, or per 1.5 kg liver weight); between $5.0\times10^8$ to $5.0\times10^9$ bacteria per 70 kg (or per 1.7 square meters surface area, or per 1.5 kg liver weight); between $10^9$ and $10^{10}$ bacteria per 70 kg (or per 1.7 square meters surface area, or per 1.5 kg liver weight); between $2\times10^9$ and $2\times10^{10}$ bacteria per 70 kg (or per 1.7 square meters surface area, or per 1.5 kg liver weight); between $5\times10^9$ and $5\times10^{10}$ bacteria per 70 kg (or per 1.7 square meters surface area, or per 1.5 kg liver weight); between $10^{11}$ and $10^{12}$ bacteria per 70 kg (or per 1.7 square meters surface area, or per 1.5 kg liver weight); between $2\times10^{11}$ and $2\times10^{12}$ bacteria per 70 kg (or per 1.7 square meters surface area, or per 1.5 kg liver weight); between $5\times10^{11}$ and $5\times10^{12}$ bacteria per 70 kg (or per 1.7 square meters surface area, or per 1.5 kg liver weight); between $10^{12}$ and $10^{13}$ bacteria per 70 kg (or per 1.7 square meters surface area); between $2\times10^{12}$ and $2\times10^{13}$ bacteria per 70 kg (or per 1.7 square meters surface area, or per 1.5 kg liver weight); between $5\times10^{12}$ and $5\times10^{13}$ bacteria per 70 kg (or per 1.7 square meters surface area, or per 1.5 kg liver weight); between $10^{13}$ and $10^{14}$ bacteria per 70 kg (or per 1.7 square meters surface area, or per 1.5 kg liver weight); between $2\times10^{13}$ and $2\times10^{14}$ bacteria per 70 kg (or per 1.7 square meters surface area, or per 1.5 kg liver weight); $5\times10^{13}$ and $5\times10^{14}$ bacteria per 70 kg (or per 1.7 square meters surface area, or per 1.5 kg liver weight); between $10^{14}$ and $10^{15}$ bacteria per 70 kg (or per 1.7 square meters surface area, or per 1.5 kg liver weight); between $2\times10^{14}$ and $2\times10^{15}$ bacteria per 70 kg (or per 1.7 square meters surface area, or per 1.5 kg liver weight); and so on, wet weight.

Also provided is one or more of the above doses, where the dose is administered by way of one injection every day, one injection every two days, one injection every three days, one injection every four days, one injection every five days, one injection every six days, or one injection every seven days, where the injection schedule is maintained for, e.g., one day only, two days, three days, four days, five days, six days, seven days, two weeks, three weeks, four weeks, five weeks, or longer. The invention also embraces combinations of the above doses and schedules, e.g., a relatively large initial bacterial dose, followed by relatively small subsequent doses, or a relatively small initial dose followed by a large dose.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The present invention encompasses a method of administering *Listeria* that is oral. Also provided is a method of administering *Listeria* that is intravenous. Moreover, what is provided is a method of administering *Listeria* that is oral, intramuscular, intravenous, intradermal and/or subcutaneous. The invention supplies a *Listeria* bacterium, or culture or suspension of *Listeria* bacteria, prepared by growing in a medium that is meat based, or that contains polypeptides derived from a meat or animal product. Also supplied by the present invention is a *Listeria* bacterium, or culture or suspension of *Listeria* bacteria, prepared by growing in a medium that does not contain meat or animal products, prepared by growing on a medium that contains vegetable polypeptides, prepared by growing on a medium that is not based on yeast products, or prepared by growing on a medium that contains yeast polypeptides.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., PA; Chabner and Longo (eds.) (2001) Cancer Chemotherapy and Biotherapy, Lippincott, Williams & Wilkins, Phila., Pa.).

Additional agents which are beneficial to raising a cytolytic T cell response may be used as well. Such agents are termed herein carriers. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleoteide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and other like immune modulators such as cyclic dinucleotide STING agonists including c-di-GMP, c-di-AMP, c-di-IMP, and c-AMP-GMP, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

The reagents and methods of the present invention provide a vaccine comprising only one vaccination; or comprising a first vaccination; or comprising at least one booster vaccination; at least two booster vaccinations; or at least three booster vaccinations. Guidance in parameters for booster vaccinations is available. See, e.g., Marth (1997) Biologicals 25:199-203; Ramsay, et al. (1997) Immunol. Cell Biol. 75:382-388; Gherardi, et al. (2001) Histol. Histopathol. 16:655-667; Leroux-Roels, et al. (2001) Act A Clin. Belg. 56:209-219; Greiner, et al. (2002) Cancer Res. 62:6944-6951; Smith, et al. (2003) J. Med. Virol. 70:Suppl. 1:S38-541; Sepulveda-Amor, et al. (2002) Vaccine 20:2790-2795).

Formulations of therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

EXAMPLES

The following examples serve to illustrate the present invention. These examples are in no way intended to limit the scope of the invention.

Example 1

Construction of Lm RIID (*Listeria monocytogenes* Recombinase Induced Intracellular Death) Strains DNA Manipulations, Purification and Vector Assembly.

Recombinase recognition sites (loxP, lox66 and lox71 variants, or frt) were inserted in the intergenic regions 5' and 3' of essential *Listeria monocytogenes* (Lm) gene sets using allelic exchange (Camilli, 1993). Recombinase sites were added to allelic exchange vectors by PCR using 10403S (Bishop, 1987) DNA as template. PCR was performed using the high-fidelity enzyme Phusion DNA polymerase (NEB, Ipswich, Mass.) in a Mycycler thermocycler (BioRad, Hercules Calif.). The oligonucleotides (oligos) (Integrated DNA Technologies, Coralville, Iowa) used for cloning are listed in the following table.

TABLE 4

| Oligonucleotides | | |
|---|---|---|
| Oligo name | Sequence (SOE overlap underlined) | RE site |
| PL1536 | tttCGGCCGatgagtaacctattaactgttcat (SEQ ID NO: 7) | EagI |
| PL1537 | tttGGATCCttagtctccatcttctaataat (SEQ ID NO: 8) | BamHI |
| PL2861 | tttGGTACCggtcatgatgacattaatacaaca (SEQ ID NO: 9) | KpnI |
| PL2862 | tttGAGCTCtatcctaaatggctttatatcagt (SEQ ID NO: 10) | SacI |

TABLE 4-continued

Oligonucleotides

| Oligo name | Sequence (SOE overlap underlined) | RE site |
|---|---|---|
| PL2863 | tttAAGCTTttggaaattcgattacccact (SEQ ID NO: 11) | HindIII |
| PL2864 | tttGGTACCtggttattttcgtcgaataactgcc (SEQ ID NO: 12) | KpnI |
| PL2865 | tttGGTACCtttGAGCTCttttagtaaaaaaacgccagagaagc (SEQ ID NO: 13) | KpnI/SacI |
| PL2866 | tttGAATTCtccgttgttgcaatattcgct (SEQ ID NO: 14) | EcoRI |
| PL2876 | tttAAGCTTtccctgaagaagaagtagcaatta (SEQ ID NO: 15) | HindIII |
| PL2868 | tttGGTACCagcttgattttattcttctatgtcgc (SEQ ID NO: 16) | KpnI |
| PL2869 | tttGGTACCtttGAGCTCggaaatgactctaatttgcaat (SEQ ID NO: 17) | KpnI/SacI |
| PL2870 | tttGAATTCtccatgtatacccaatcgtttagga (SEQ ID NO: 18) | EcoRI |
| PL3139 | <u>ataacttcgtatagcatacattatacgaacggta</u>ggaaatgactctaatttgcgaat (SEQ ID NO: 19) | |
| PL3140 | tttGAATTCtccatgtatacccaatcgtttagga (SEQ ID NO: 20) | EcoRI |
| PL3141 | tttAAGCTTtccctgaagaagaagtagcaatta (SEQ ID NO: 21) | HindIII |
| PL3142 | <u>taccgttcgtataatgtatgctatacgaagttat</u>agcttgattttattcttctatgtcgc (SEQ ID NO: 22) | |
| PL3246 | tttGAATTCacagaaggagattgtgaaatg (SEQ ID NO: 23) | EcoRI |
| PL3247 | gggTCTAGAtttGGTACCaatagaagcgtactgcgact (SEQ ID NO: 24) | KpnI/XbaI |
| PL3248 | gggTCTAGAgtttcacgtgaaacattcta (SEQ ID NO: 25) | XbaI |
| PL3249 | tttAAGCTTcggaattggttcaagactgg (SEQ ID NO: 26) | HindIII |
| PL3339 | attGGTACCttcgaggagtaaacttcccaa (SEQ ID NO: 27) | KpnI |
| PL3340 | aacTCTAGAcaccgcggtggcggccgataa (SEQ ID NO: 28) | XbaI |
| PL3378 | <u>tatGCGGCCGCgggaagcagttggggttaact</u> (SEQ ID NO: 29) | NotI |
| PL3379 | <u>aacTCTAGActtagtctccatcttctaata</u> (SEQ ID NO: 30) | XbaI |
| PL3469 | <u>aaaggaagttcctattctctagaaagtataggaacttctgc</u>ggaaatgactctaatttgc (SEQ ID NO: 31) | |
| PL3470 | <u>gcagaagttcctatactttctagagaataggaacttccttt</u>agcttgattttattcttct (SEQ ID NO: 32) | |
| PL3471 | <u>aaaggaagttcctattctctagaaagtataggaacttctgc</u>ttttagtaaaaaaacgcca (SEQ ID NO: 33) | |
| PL3472 | <u>gcagaagttcctatactttctagagaataggaacttccttttt</u>ggttattttcgtcgaata (SEQ ID NO: 34) | |
| PL3546 | tttCTGCAGgtggatagaactcataaaggac (SEQ ID NO: 35) | PstI |
| PL3547 | tttGGTACCtcagttaaccccaactgcttc (SEQ ID NO: 36) | KpnI |
| PL3548 | tttGGTACCtttAGATCTaaacacagaacgaaagaaaaag (SEQ ID NO: 37) | KpnI/BglII |
| PL3549 | tttGAATTCccagtaggttccactgtatc (SEQ ID NO: 38) | EcoRI |
| PL3552 | tttCTGCAGtccatgtatacccaatcgtttagga (SEQ ID NO: 39) | PstI |
| PL3553 | tttAAGCTTtccctgaagaagaagtagcaatta (SEQ ID NO: 40) | HindIII |
| PL4017 | tttAGATCTaaatggttttttctctctataa (SEQ ID NO: 41) | BglII |
| PL4018 | tAGATCTataacttcgtatagcatacattatacgaacggtattcgaaaattattgcgtta (SEQ ID NO: 42) | BglII |
| PL4075 | tttCTGCAGatgattcaatccttcttgctt (SEQ ID NO: 43) | PstI |
| PL4076 | gggTCTAGAgagttatacaaaacgggaata (SEQ ID NO: 44) | XbaI |

The following table provides a list of sequences used in the following examples.

vectors were confirmed by diagnostic colony PCR, restriction digest, and sequencing (SeqXcel, San Diego Calif.).

TABLE 5

Sequences

| Name | Sequence |
|---|---|
| lox66 | Ataacttcgtatagcatacattatacgaacggta (SEQ ID NO: 45) |
| lox71 | Taccgttcgtatagcatacattatacgaagttat (SEQ ID NO: 46) |
| loxP | Ataacttcgtataatgtatgctatacgaagttat (SEQ ID NO: 47) |
| actA promoter | gggaagcagttggggttaactgattaacaaatgttagagaaaaattaattctccaagtgatattcttaaaata attcatgaatatttttctttatattagctaattaagaagataattaactgctaatccaattttaacggaataaa ttagtgaaaatgaaggccgaattttccttgttctaaaaaggttgtattagcgtatcacgaggagggagtataa (SEQ ID NO: 48) |
| Cre (codon optimized) | atgagtaacctattaactgttcatcaaaatttaccagcattaccagtggatgcaacatcagatgaagtaagaa aaaatttaatggatatgtttagagaccgacaagcctttcggagcatacatggaaaatgttattatctgtttgt agatcatgggcagcatggtgcaaacttaacaatagaaaatggtttccagcagaaccagaagatgtacgaga ttatttattataccttcaagcaagaggattagcagtaaaaaccattcaacaacatttaggacaattaaatatg ttacatagacgatcaggattaccaagacctagcgattctaacgcagttagtttagttatgagaagaattagaa aagaaaatgtcgatgcaggcgaacgagcaaaacaagcactagcatttgaacgtacagatttcgaccaagta agatcattaatggaaaatagcgaccgttgtcaagacatccgaaacttagcttttttaggaatagcatacaaca cattattaagaatagcagaaatagccagaattagagtagaagaagcattagtagaacagtggaggaagaat gttaattcatattggaagaacaaaaacattagtatcaacagccgggtagaaaaagcgttatcattaggagt tacaaaattagtagaacgatggatttcagtttcaggagtggcagatgacccaaataattatttattttgtagag tacgaaaaaacggagtagcagcaccttcagcaacaagtcaattaagtacaagagcattagaaggaatattc gaagcaacacatcgactaattttacggagcaaaagatgatagtggacaacgatatttagcttggagtggaca cagtgcgcgagtaggagcagcaagagatatggcaagagcgggagttagtataccagaaataatgcaagca ggaggatggacaaatgtaaatattgtaatgaattatattagaaatttagatagtgaaaccggtgcaatggta cgattattagaagatggagactaa (SEQ ID NO: 49) |
| frt | Gaagttcctattctctagaaagtataggaacttc (SEQ ID NO: 50) |
| FLP (codon optimized) | atgtcgcaatttgatatactatgtaaaactccacctaaagtattagtgcgtcaatttgttgaacgttttgaacga ccaagtggcgaaaagatagcttcctgtgccgcggaacttacttacttgtgttggatgattacacataatggca ctgcaatcaaaagagcaacattcatgtcatacaacaccatcatttctaattctttatcatttgatattgttaaca aaagtttacaattcaaatacaaaactcaaaaagcgacgattcttgaagctagtttgaaaaagttaatcccag catgggagtttaccatcattccttacaatggacagaaacaccaatccgacattacagacattgtttctagttta caactacaatttgaaagcagtgaagaagcggataaagggaactcacattcgaagaaaatgttaaaggcttt gttatctgaaggagaatctatctgggagattacagaaaagattctaaactcttttgagtatacttcacgcttta ctaaaaccaaaacgttataccagtttcttttttctagctacattcattaactgcggtcgatttagtgacattaaga atgtagatcctaaatcgttcaagttagtccaaaacaagtatctaggtgtcatcattcaatgcttagttacggaa acaaaaacgagtgtaagtagacatatctatttcttttctgctagaggtagaattgatccgcttgtatacttaga tgaatttctacgtaattcagagccggtgcttaaacgcgttaatcgtacaggaaatagctcaagcaataagca agaatatcaacttttgaaagacaatttggtgcgtagctataacaaagcgttaaagaagaatgcaccatatcc gatattcgccatcaaaaacgggccaaaatcccacattggtcgccatcttatgactagcttcctttcgatgaaa ggattaacggagttaacaaatgtggtaggtaattggtccgacaaaagagcgagtgctgtagcacgaacgac atatacacatcagattacagctattccagatcactactttgcattagttagtagatactatgcatgatccaat ttccaaagaaatgattgctcttaaagatgaaacaaatccaatagaagaatggcaacatatcgaacaactta aaggatcggcagaaggctctatacgttatcctgcatggaatggtatcatttctcaagaagttttagactatttg tcaagctatatcaatcgtcgcatttaa (SEQ ID NO: 51) |

PCR products were purified with QIAquick purification columns (Qiagen, Valencia, Calif.), digested with appropriate restriction enzymes (NEB) and ligated to pKSVoriT, a derivative of the temperature sensitive allelic exchange vector pKSV7 (Smith, 1992), using T4 DNA ligase (NEB, Ipswich, Mass.). All vectors used for cloning were treated with calf intestinal alkaline phosphatase, (CIP), NEB, Ipswich Mass.)). Bacterial strains used for cloning, conjugation and the Lm parental strains are listed in Table 6 hereinafter. *Escherichia coli* SM10 was made chemically competent with the Z-Competent Kit (Zymo Research, Irvine Calif.). Transformations of both XL1-blue and SM10 were cultured in Luria-Bertani broth (LB) at 37° C. with appropriate antibiotic selection (pKSVoriT: 75 µg/ml carbenicillin; pPL2-based vectors: 20 µg/ml chloramphenicol. Lm strains were grown in vegetable peptone phosphate broth (VPP) (Basingstoke, UK). Lm was selected on VPP plates supplemented with 7.5 µg/ml chloramphenicol and 200 µg/ml streptomycin (Teknova, Hollister Calif.). Allelic exchange Confirmed plasmids were transformed into SM10 cells and conjugated into Lm as described. Recombinase genes were cloned downstream of the actA in the site-specific integration vector pPL2 or derivatives thereof (Lauer, 2002).

Example 2

Engineering of Cre/lox-Mediated Lm RIID Strains

Figure 2:
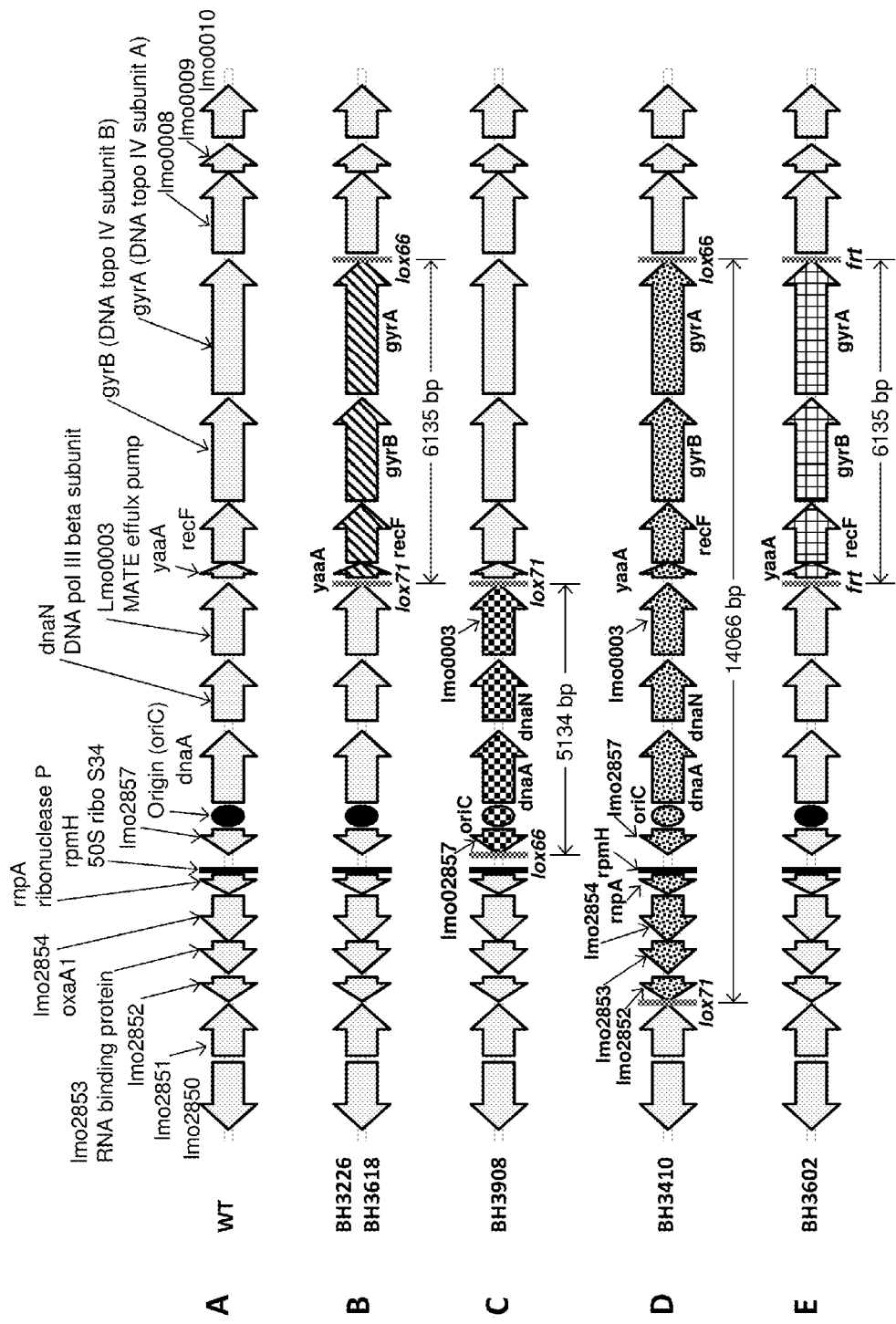
FIG. 2. Overview of regions deleted in Lm-RIID strains
Figure 4:
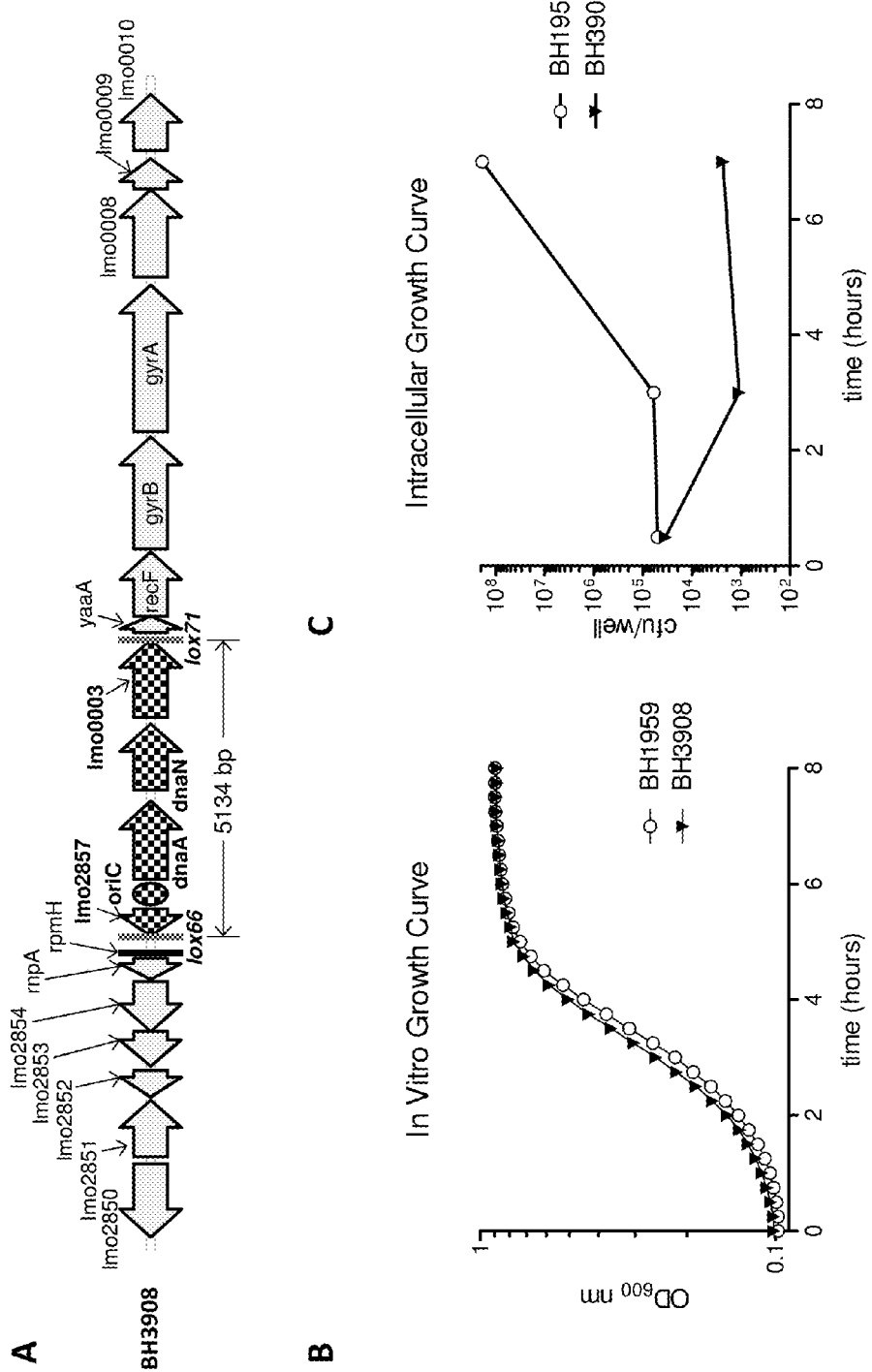
FIG. 4. Deletion 2. (A) Lox recombinase sites flanking lmo2587, origin, dnaA, dnaN, and lmo0003; (B) Growth curve in BHI Broth; (C) Intracellular growth curve in DC2.4 cells.

A non-limiting example that is illustrative of Lm RIID strains was based on targeting bacterial genes involved in the winding/unwinding of the bacterial genome during DNA replication, gyrB (lmo0006) and gyrA (lmo0007), encoding the two subunits of the Lm gyrase. The first step in the construction involved the placement of lox71 (Albert et al., 1995) between coding sequences of MATE efflux (lmo0003) and yaaA (lmo0004), upstream of recF (lmo0005), and was accomplished by allelic exchange, as described previously (Camilli et al., 1993). To engineer the allelic exchange vector used to generate the Lm RIID strain, the upstream flanking region of the target genes was amplified by PCR using primers PL2863/PL2864, and the downstream flanking region with primers PL2865/PL2866. The PCR products were then cloned into a derivative of the shuttle vector plasmid pKSV7 (Smith et al., 1992) that was modified to contain an oriT (pKSVoriT), resulting in plasmid pBHE1937. The lox71 sequence was inserted between the lmo0003/lmo0004 flanking regions, by amplifying a 400 bp region containing lox71 from an existing vector by PCR and subsequent cloning into pBHE1937, resulting in plasmid pBHE2099. The plasmid was sequence verified and transformed into *E. coli* SM10 for conjugation into Lm. The SM10 strain was mated with Lm strain BH1959, a live-attenuated derivative of DP-L4056 in which the actA, inlB, uvrAB coding sequences were deleted. In addition, this strain contains an antigen expression cassette at the inlB locus (as described in Lauer et al., 2008) for monitoring immunogenicity of the suicidal strain and its non-suicidal control. Allelic exchange was performed on transconjugants ultimately resulting in Lm strain BH3141.

The second mutant loxP site (lox66) was introduced downstream of lox71 (Table 5) between gyrA (lmo0007) and cardiolipin synthase (lmo0008) using splicing by overlap extension (SOE) PCR as described previously (Horton, 1993). The region adjacent to gyrA was amplified with primers PL3141/PL3142 and the downstream region (adjacent to lmo0008) was amplified with PL3139/PL3140. The lox66 sequence was included in primers PL3139 and PL3142. The primary SOE PCR products were then combined by a second PCR step, and this SOE product was then cloned into pKSV7oriT, resulting in the plasmid pBHE2193. Allelic exchange with pBHE2193 into the lox7'-containing strain BH3141 was performed, resulting in Lm strain BH3210. This strain contained the genomic region composed of yaaA-recF-gyrB-gyrA flanked by lox71 and lox66 (FIG. 2B).

The final step in generating the Lm-RIID strain involved the cloning and integration of a plasmid encoding Cre recombinase that was functionally linked to the actA promoter, restricting recombinase gene expression to the cytosol of infected cells in the vaccinated recipient. The nucleotide sequence of Cre was codon optimized for expression in Lm (Blue Heron, Bothell, Wash.). The Cre sequence was amplified with primers PL1536/PL1537 and cloned as an EagI/BamHI fragment into a pPL2-based plasmid (allowing site-specific integration at the $tRNA^{Arg}$ locus) containing the actA promoter (221 bp, Table 5), resulting in plasmid pBHE2130. This plasmid was conjugated into both the parental strain (BH1959) and the lox71/lox66-containing variant (BH3210), resulting in BH3099 (non-suicidal control) and BH3226 (Lm RIID), respectively.

As a second non-limiting illustrative example of Lm-RIID vaccines, a second set of essential genes for excision was targeted by placing a lox66 site on the other side of the bacterial origin in the strain BH3141, which contains a lox71 between BH3141 lmo0003 and lmo0004. The region deleted in this second strain includes lmo2587, the origin of replication (oriC), the essential replication initiator genes dnaA and dnaN (encoding a subunit of DNA polymerase III), and lmo0003 (FIG. 2C). The allelic exchange vector, pBHE2724, was engineered by first amplifying a region extending from the 3' end of rnpA through 150 bp downstream of rpmH by PCR, using oligo set PL4075/PL4017 (flanking region 1). The second flanking region, composed of the majority of lmo2857, was amplified using oligo set PL4018/PL4076 (flanking region 2). The lox66 sequence was included in the forward primer PL4018. The two flanking regions were assembled into the vector pKSVoriT using restriction enzyme mediated three-way ligation. The same allelic exchange process was repeated to embed lox66 in the intergenic region between rpmH and lmo2857. After confirming insertion of the lox66-containing sequence in strain BH3141, the new strain was designated BH3901. pBHE2130 (containing the PactA-Cre cassette) was introduced by conjugation resulting in the Lm RIID strain BH3908. Using similar methods, a third non-limiting illustrative example of Lm-RIID vaccines was generated through targeting a deletion spanning the 14 kilobase region from lmo2582 through gyrA (FIG. 2D). The first flanking region spanning 1031 bp including lmo2851 was amplified by PCR using the primers PL3246/PL3247. The second flanking region spanning 1029 bp including lmo2852 and most of lmo2853, was amplified by PCR using oligos PL3248/PL3249. Both fragments were cloned into pKSVoriT in the vector pBHE2292. Lox71 from pBHE2099 (described above) was amplified by PCR using the primers PL3339/PL3340 and cloned into the KpnI/XbaI sites of pBHE2292, resulting in pBHE2358. To allow the simultaneous incorporation of both the lox71 site and the PactA-Cre cassette in the same allelic exchange, the Cre cassette of pBHE2130 was amplified with PL3378/PL3379 and cloned into pBHE2358 between lox71 and the lmo2852 flanking region, resulting in allelic exchange vector pBHE2382. The lox66 site was introduced into the live attenuated Lm11 strain (live-attenuated Lm ΔactA ΔinlB vaccine strain) using pBHE2193 (described above), resulting in intermediate strain BH3291. A second allelic exchange was performed to insert lox71 and PactA-Cre between lmo2851 and lmo2852 with that contained in pBHE2382 in BH3291 resulting in the Lm-RIID strain BH3410.

A fourth Lm-RIID strain was constructed in the Lm ΔactA ΔinlB strain background, which allowed various vaccine antigen compositions to be subsequently introduced at the $tRNA^{Arg}$ locus and tested and tested in immunogenicity studies. The same sequential allelic exchange process that gave rise to BH3210 was repeated in the Lm11 strain background. First, pBHE2193 was used to insert the lox66 site downstream of gyrA, then pBHE2099 was used to insert the lox71 site upstream of yaaA. The strain containing the lox71-yaaA-recF-gyrB-gyrA-lox66 composition (FIG. 2B) was designated BH3339. The PactA-Cre cassette was introduced by allelic exchange at the deleted actA locus of the Lm ΔactA ΔinlB strain, allowing vaccine antigen expression cassettes to be subsequently introduced at the $tRNA^{Arg}$ locus to generate vaccine strains for evaluation in animal studies. The actA-upstream flanking region including 825 bp of the mpl gene was amplified by PCR using primers PL3546/PL3547. The actA-downstream flanking region that includes 797 bp of the plcB gene was amplified by PCR with primers PL3548/PL3549. The PCR products were cloned into pKS-VoriT by three-way ligation resulting in the vector pBHE2519. The pBHE2519 plasmid vector contained unique KpnI and BglII sites between the two flanking regions. The PactA-Cre cassette was subcloned from pBHE2130 into pBHE2519 resulting in pBHE2525. Allelic exchange was used to introduce the PactA-Cre cassette at the ΔactA locus, resulting in Lm-RIID strain BH3618.

Example 3

Of FLP/frt-Based RIID Strains

It will be apparent to the skilled artisan that additional recombinase methods can be used to selectively delete Lm genes required for multiplication in the cytosol of the infected host cell. A non-limiting example is to utilize the yeast recombinase FLP with the frt recombination sites instead of the Cre/loxP system to generate Lm-RIID vaccines. A strain that was analogous in composition to BH3226 (FIG. 2B) was generated by replacing the lox66 and lox71 sites with frt recombination sites (FIG. 2E) and utilizing FLP recombinase instead of Cre recombinase. An allelic exchange vector analogous to pBHE1937 (described in example 1) was constructed by inserting a frt site between lmo0003 and lmo0004 as follows: PCR was performed on 10403S DNA with primer pairs PL2863/PL3472 (MATE efflux, lmo0003) and PL3471/PL2866 (yaaA, lmo0004). Primers PL3471 and PL3472 added frt sequences to the native Listeria sequences. Secondary SOE PCR was used to combine PCR products into a single DNA fragment that contained the two flanking regions with an intervening frt site. This construct was cloned into pKSV7oriT as a PstI/EcoRI fragment, giving rise to pBHE2503. pBHE2503 was introduced into Lm11 by conjugation and allelic exchange was performed, resulting in BH3558. A second set of SOE PCR reactions were used to assemble the allelic exchange vector, pBHE2522 which introduced a frt recombination site between gyrA and lmo0008. Similar flanking regions found in pBHE2193 (described in example 1), were amplified with primer sets PL3553/PL3470 (gyrA) and PL3469/PL3552 (lmo0008). Primers PL3469 and PL3470 added a frt sequence to the native Listeria sequence. SOE PCR was used to assemble a DNA fragment with the two flanking regions with an intervening frt site, and the PCR product was cloned into pKVS7oriT as a HindIII/PstI fragment, resulting in pBHE2522. pBHE2522 was introduced into BH3558 by conjugation and, after allelic exchange, resulted in the strain where the gyrase region is flanked with frt sites, BH3578 (FIG. 4E). Finally, a vector was constructed to express FLP recombinase from the actA promoter. The FLP recombinase coding sequence was codon optimized for expression in Listeria (DNA2.0, Menlo Park Calif.) and synthesized de novo and cloned, resulting in the vector pJ201:64349 as a ClaI/EagI fragment. The actA promoter was cloned into an erythromycin resistant derivative of pPL2 (Lauer, 2008), and the FLP coding sequence was subcloned from pJ201:64349 downstream of the actA promoter, resulting vector pBHE2516. pBHE2516 was sequence verified, introduced into strain BH3578 by conjugation, and integrated at the tRNA$^{Arg}$ locus, resulting in the FLP/frt-based Lm RIID strain BH3602.

Example 4

Laboratory Analysis Methods

In Vitro Growth Curves

Cultures grown overnight in BHI (BD Difco, Franklin Lakes, N.J.) were diluted 1:100 into fresh BHI and grown at 37° C. shaking at 250 rpm. Optical density (OD$_{600}$ nm) was measured in a BioRad SmartSpec 3000 (BioRad, Hercules, Calif.). Alternatively, overnight BHI cultures were diluted 1:100 and 150 μL/well was aliquoted into a 96-well, flat bottomed plate and monitored for growth using a Versa max microplate reader (Molecular Devices, Sunnyvale Calif.).

Intracellular Growth Curves

Growth curves in the dendritic cell line DC2.4 (Shen, 1997) were performed in 24-well tissue-culture plates (Costar 3524, Corning, N.Y.). 2×10$^5$ DC2.4 cells were seeded per well in RPMI 1640 (Thermo Scientific, Waltham, Mass.) supplemented with 10% heat-inactivated fetal bovine serum (Hyclone), 23.8 mM sodium bicarbonate (Sigma), 1× non-essential amino acids (Cellgro), 2 mM L-glutamine (Cellgro), 1×10$^{-2}$M HEPES buffer (Gibco), 1 mM sodium pyruvate (Sigma), and 50 μM β-mercaptoethanol (Sigma, St. Louis, Mo.). For infection, Lm strains were grown overnight in BHI at 30° C. without agitation, then diluted into RPMI to a final concentration 4×10$^6$ cfu/mL, 0.5 mL was used to infect each well for a final multiplicity of infection (moi) of 20. Cells were infected for 45 min, washed with 1 ml DPBS (HyClone, South Logan Utah), and RPMI complete medium containing 50 μg/mL gentamycin was added to prevent growth of extracellular bacteria. Intracellular bacterial growth was monitored at several time-points by aspiration of the media, washing cell monolayers with DPBS and lysing the cell monolayer hypotonically with 1 mL of sterile water. Serial 10 fold dilutions were plated on BHI agar plates supplemented with 200 μg/ml streptomycin (Teknova, Hollister Calif.). Plates were incubated overnight at 37° C. and enumerated for calculation of cfu/well.

Western Blots

Semi-quantitative intracellular Western blots were performed in DC2.4 cells. 3×10$^5$ DC2.4 cells were seeded in each well of a 12-well tissue culture plate and incubated overnight. Cells were infected with 6×10$^6$ of test Lm strains per well (MOI 20). Cells were incubated for 1 hour, rinsed with DPBS, and RPMI complete medium containing 50 μg/mL gentamycin was added. Cells were cultured seven additional hours at 37° C./5% $CO_2$ before washing each well with 1 mL DPBS and lysing cells in 150 μL 1×LDS (250 μL 4×LDS buffer (Life Technologies, Grand Island N.Y.), 650 μL TE buffer (Fisher Scientific, Waltham Mass.) 100 μL sample reducing agent (Life Technologies, Grand Island N.Y.)). Cell lysates were heated in a block at 95° C. for 10 min and 20 μL aliquots were run on 4-12% Bis-Tris PAGE gels in 1×MES buffer (Invitrogen) and transferred to nitrocellulose membranes for detection. Membranes were incubated in Odyssey blocking buffer (Li-Cor, Lincoln Nebr.). Heterologous antigens were detected using the A18K polyclonal rabbit antibody which recognizes the mature 18 amino acid amino terminus of the ActA protein, used as a fusion for antigen expression at 1:4000 dilution. Expression levels were normalized to the Listeria P60 protein using a monocloncal antibody MAB8001 at 1:4000 dilution (Fisher Scientific). P60 expression level correlates with cfu. Secondary antibodies, α-MS 800 Cw and α-Rb 680 (Li-Cor) were used at 1:1000 dilutions. Westerns were scanned and quantitated on a Li-Cor Odyssey system.

Animals

C57BL/6, BALB/c, CD1, CD1$^{nu/nu}$ and SCID beige mice were obtained from Charles River Laboratories (Wilmington, Mass.). Mice were treated according to National Institutes of Health guidelines. All animal protocols were approved by the Aduro BioTech IACUC. All vaccinations of Listeria were given intravenously at 5×10$^6$ cfu unless otherwise stated.

ELISpot Assay

Immunogenicity was monitored during the experiments by ELISpot assays performed with lymphocytes isolated from whole mouse blood using Lympholyte-Mammal (Cedarlane Labs, Burlington, N.C.) and a murine IFN-γ ELISpot pair (BD Biosciences, San Jose, Calif.). At the termination of the experiments, ELISpot assays were performed on splenocytes. 2×10$^5$ cells/well were incubated with the appropriate peptide overnight at 37° C. in anti-murine IFN-γ coated ELISpot plate (Millipore, Billerica, Mass.). Cells were incubated with no peptide as a negative control. Murine ELISpots were developed using alkaline phosphatase detection reagents (Invitrogen, Carlsbad, Calif.) and scanned and quantified using Immunospot plate reader and software (CTL Ltd, Cleveland, Ohio).

WT *Listeria* Challenge

C57BL/6 mice were vaccinated once with 5×10⁶ cfu of each Lm strain. 34 days later, mice were challenged with 2×LD$_{50}$ of the WT Lm strain DP-L4056 (Lauer, 2002). Three days later, spleens and livers were harvested and homogenized. Dilutions were plated on BHI plates containing 200 µg/mL streptomycin to determine cfu/organ.

Vaccinia Challenge

C57BL/6 mice were vaccinated on day 0 and day 29 with 5×10⁶ cfu of various Lm strains. Mice were challenged 49 days post second vaccination with WT vaccinia intraperitoneally with 1×10⁶ pfu. Ovaries were harvested 5 days later and plaque assays were performed to determine the level of protection (Brockstedt, 2005).

Tumor Studies

BALB/c mice were challenged intravenously on day 0 with 2×10⁵ the CT26 tumor cell line engineered to express human mesothelin. Mice were vaccinated 4 days later with 5×10⁶ cfu Lm RIID, along with appropriate controls, and boosted with the same vaccination dose 14 days later. Mice were weighed and monitored daily. At the time of death, lungs were harvested and metastases enumerated.

Example. 5

Results

To be effective, vaccines require a balance between immunogenicity, potency and safety. For practical reasons, it is further desirable that vaccines can be easily manufactured at large scale using establish fermentation methods. Lm constitutes an immunologically potent vaccine platform due to its properties of cytosolic access, where it multiplies, and can be engineered further to express and secrete encoded antigens which are subsequently processed and presented on MHC class I molecules, and priming of antigen-specific CD8+ T cell responses (Brockstedt and Dubensky, 2008). Wild-type or live-attenuated Lm strains such as Lm ΔactA/ΔinlB grow and multiply in broth culture and also grow and multiply in cells where they can also deliver antigenic target proteins to the host cytosol inducing an immune response. Lm-RIID vaccines have been developed to readily grow in broth culture and to deliver vaccine antigens to the host cell, but have been further engineered to initiate a program within the cytosol of the infected cell to "commit suicide," preventing bacterial multiplication and increasing the safety of the vaccine platform (FIG. 1).

To evaluate the growth characteristics of the Lm-RIID vaccine platform, the Lm-RIID strains BH3226 and BH3618 that delete the gyrase region, termed Deletion 1 (FIG. 3A) to the parent strain BH3210 (which contains both lox66 and lox71 sites but lacks the Cre recombinase expression cassette; genotypes and strain characteristics for all strains are listed in Table 6), were compared for growth characteristics in vitro (fermentation in broth culture) and in host cells. Growth in vitro was measured following optical density over time in BHI broth culture over the course of 8 hours (as described in Example 1). In vitro growth curves were very similar for all strains (FIG. 3A), demonstrating that both the parent strain and Lm-RIID strain can be propagated by conventional fermentation methods. Next, the intracellular growth kinetics for the BH3210 parental Lm strain and the Lm-RIID strains BH3226 and BH3618 were in the DC2.4 mouse dendritic cell line were compared. BH3210 grew like a typical wild-type Lm strain, multiplying approximately 2 logs over the course of 7 hours (Portnoy et al., 1988). In contrast, both BH3226 and BH3618 Lm-RIID strains lost the ability to generate colony forming units over the same time frame by 2 to 4 logs (FIG. 3C). These results demonstrate that while Lm-RIID strains can be propagated by conventional methods in fermentation culture, following infection of host mammalian cells, the expression of Cre recombinase is induced, resulting in the subsequent excision of the region containing the essential gyrase genes gyrB and gyrA, and loss of viability.

As an additional non-limiting illustration of the approach, the kinetics of growth in broth culture and intracellular growth of Lm-RIID strains that targeted a second set of essential genes were determined. The Lm-RIID Deletion 2 strain that was engineered to delete the chromosomal origin of replication (oriC), as well as the essential replication initiation genes dnaA and dnaN (FIG. 4A). Lm-RIID BH3908 strain contains lox66 and lox71 sites flanking oriC, dnaA, and dnaN, and grew in broth culture with the same kinetics as did the parental BH1959 strain (FIG. 4B). In contrast, following infection of DC2.4 mouse dendritic cells, the Lm-RIID BH3908 strain rapidly lost viability (>2 logs in cfu) over the 7 hour time course, while the parental Lm BH1959 strain multiplied by >2 logs in cfu, a 4 to 5-log difference compared to the Lm-RIID strain. These results provide a second non-limiting example that while Lm-RIID strains can be propagated by conventional methods in fermentation culture, following infection of host mammalian cells, the expression of Cre recombinase is induced, resulting in the subsequent excision of the region containing the essential oriC, dnaA, and dnaN genes and loss of viability.

Figure 5:
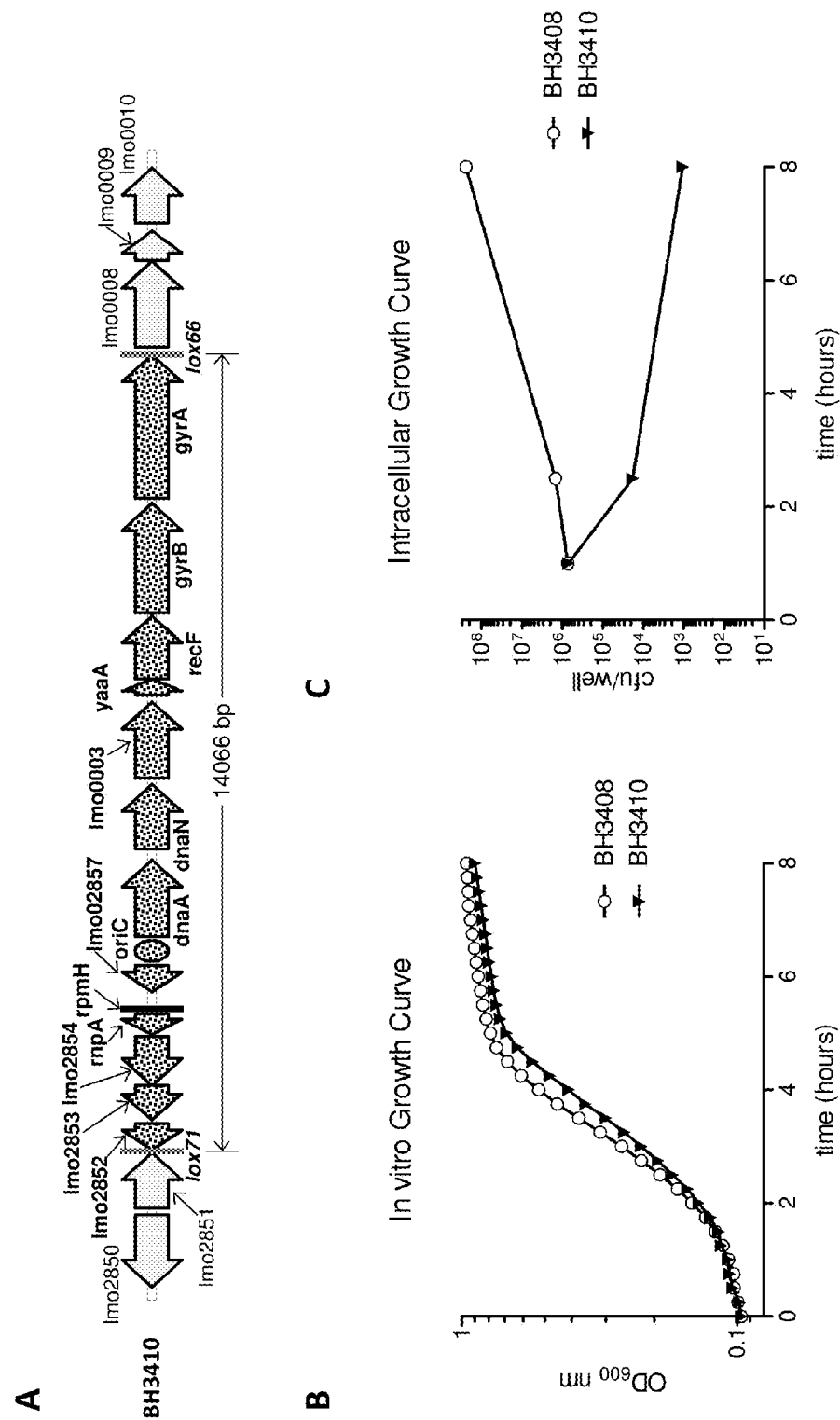
FIG. 5. Deletion 3. (A) Lox recombinase sites flanking lmo2582-origin-gyrA region; (B) In vitro growth curve in BHI; (C) Intracellular growth curve in DC2.4 cells.

As yet a further non-limiting illustration of the approach, the kinetics of growth in broth culture and intracellular growth of Lm-RIID strains that targeted a third set of essential genes were determined. Lm-RIID strains were constructed that contained a Deletion 3 composition, which spanned both Deletion 1 and Deletion 2 described herein, and also included 5 additional identified open reading frames in the *Listeria* genome (lmo2852 through rpmH) (FIG. 5A). The growth characteristics of Lm-RIID strain BH3410 in broth culture was compared to the parental strain BH3408, which contained a single lox71 site between lmo2851 and lmo2852 and the PactA-Cre cassette inserted in the same intergenic region. The growth characteristics between the Lm-RIID strain and the parental strain were indistinguishable, demonstrating once again that Lm-RIID strains can be propagated by conventional broth culture fermentation (FIG. 5B). Additionally, intracellular growth curves closely approximated the data from strains Deletion 1 and Deletion 2. In contrast, following infection of DC2.4 mouse dendritic cells, the Lm-RIID BH3410 strain rapidly lost viability (approximately 3 logs in cfu) over the 7 hour time course, while the Lm BH3408 parental strain multiplied by >2 logs in cfu, a 5-log difference compared to the Lm-RIID strain (FIG. 5C).

Figure 6:
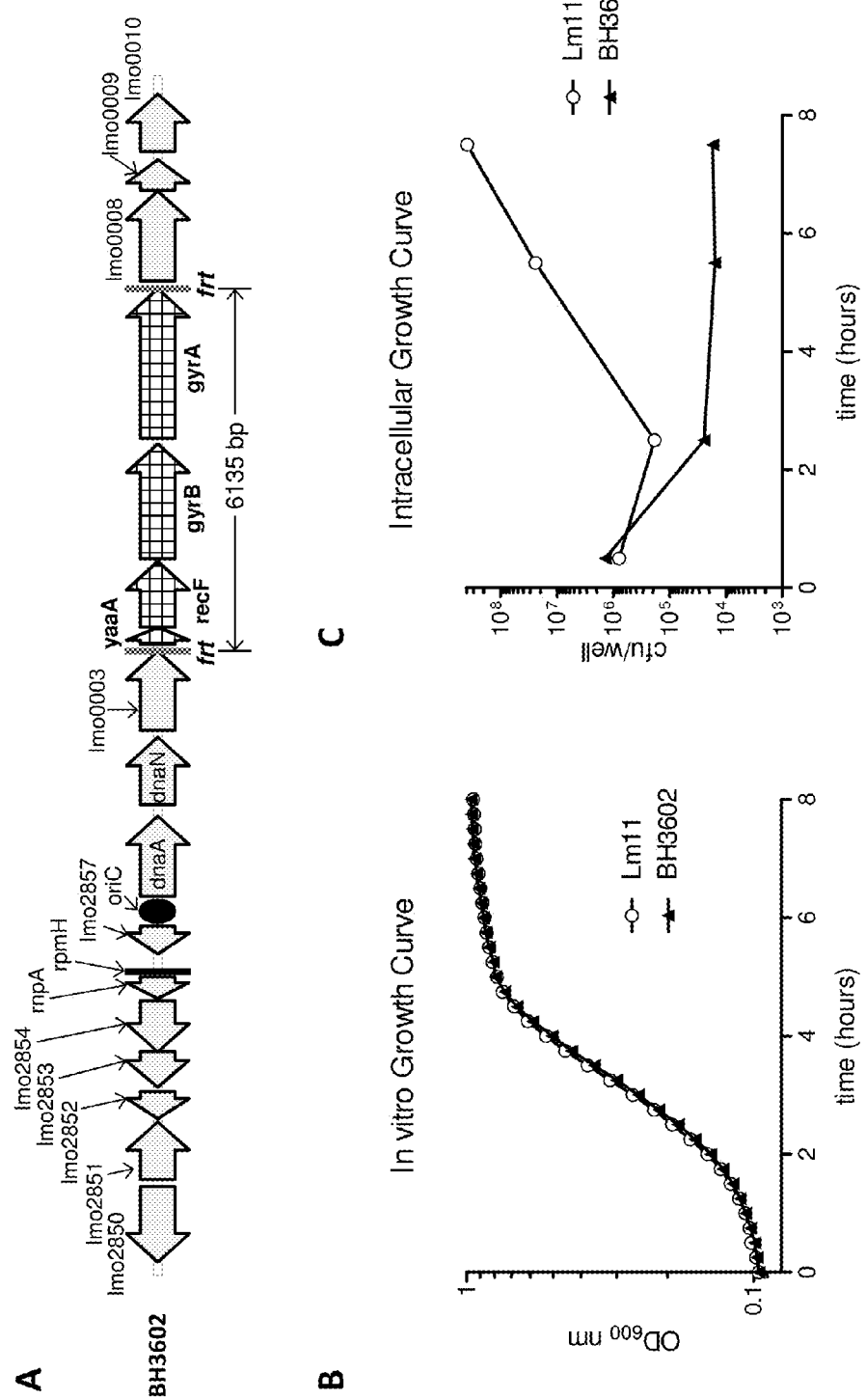
FIG. 6. Deletion 4. (A) Frt recombinase sites flanking the gyrase region (yaaA, recF, gyrB, gyrA); (B) In vitro growth curve in BHI; (C) Intracellular growth curve in DC2.4 cells.
Figure 7:
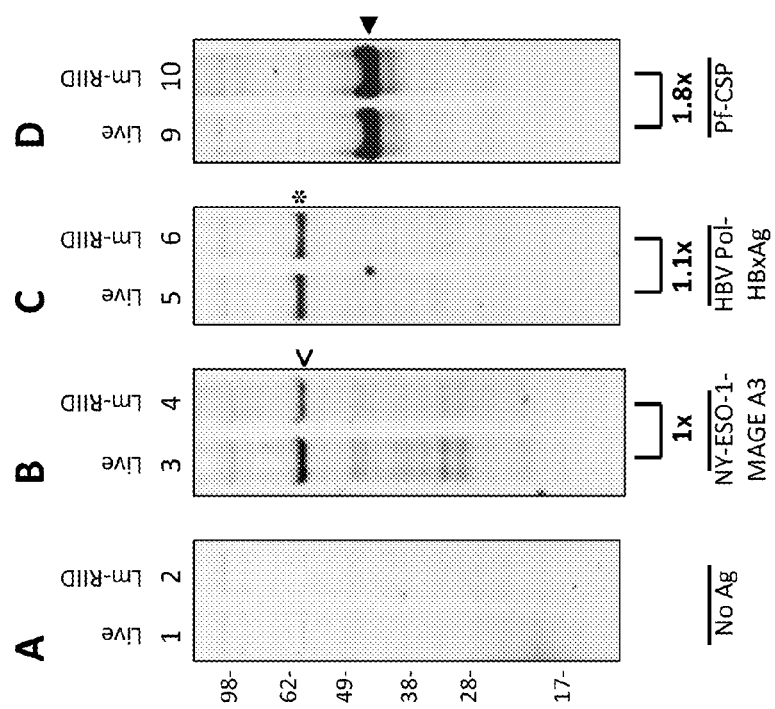
FIG. 7. Comparison of intracellular expression of various antigens from live attenuated (Lm11) and Lm-RIID (BH3618) platforms. A-D: Intracellular Western blot of four pairs of strains in the Lm11 or BH3618 strain background. (A) Lane 1: live Lm strain Lm11; Lane 2: Lm-RIID strain BH3618; platform strains without added antigen. (B) Lane 3: live Lm strain BH3943; lane 4: Lm-RIID strain BH3953; Antigen: ActAN100-Ny-ESO-1-MAGE A3 fusion protein (<). (C) Lane 5: Live Lm strain BH3947; lane 6: Lm-RIID strain BH3957; Antigen: ActAN100-HBV Polymerase-HBxAg fusion protein (*). (D) Lane 9: Live Lm strain BH3951; lane 10: Lm-RIID strain BH3961; Antigen: ActAN100-*Plasmodium falciparum* CSP fusion protein (◄).
Figure 8:
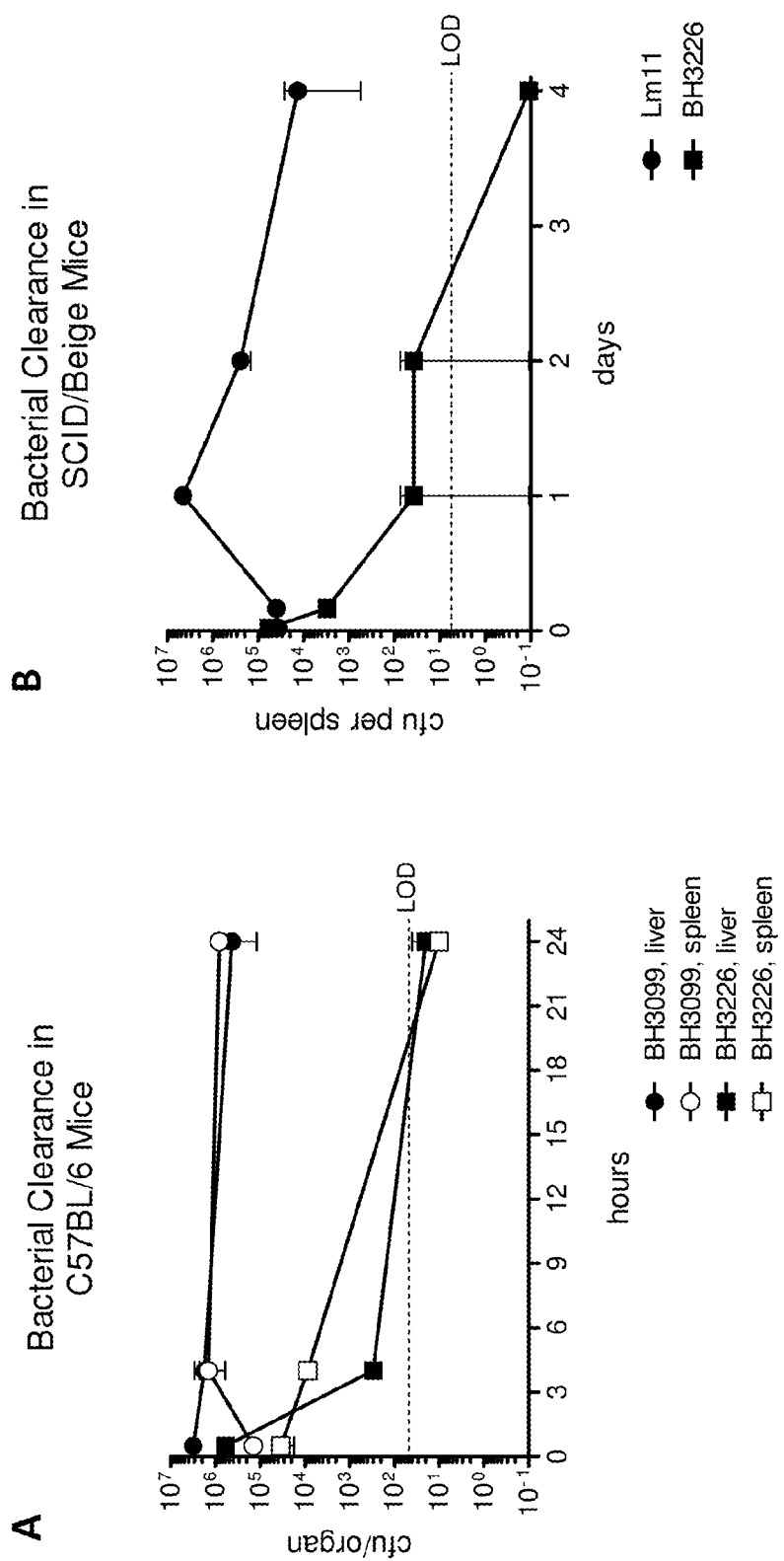
FIG. 8. Accelerated clearance and safety of Lm-RIID strains in immune-competent and immune-deficient mice.

The skilled artisan will recognize that alternative recombinase systems can be used to selectively delete Lm genes required for multiplication in the cytosol of the infected host cell. The growth characteristics of Lm-RIID strain BH3602 in broth culture and after infection of DC2.4 cells was compared to the live-attenuated parental strain Lm11 (Lm ΔactA/ΔinlB). BH3602 targeted essential genes yaaA, recF, gyrB, gyrA for deletion, which was similar to the genes targeted in Deletion 1 of Lm-RIID strains BH3226 and BH3618, except Lm-RIID strain BH3602 utilizes the alternate recombinase system FLP/frt (FIG. 6A). The in vitro growth kinetics of the Lm-RIID strain BH3602 and the Lm11 parental strain were indistinguishable. In contrast, following infection of DC2.4 mouse dendritic cells, the Lm-RIID strain BH3602 rapidly lost viability (approximately 2 logs in cfu) over the 7 hour time course, while the Lm 11 parental strain multiplied by >2 logs in cfu, a 4-log difference compared to the Lm-RIID strain (FIG. 5C).

The following table provides a list of bacterial strains prepared as described herein:

artisan that the magnitude of antigen expression can impact the magnitude of the vaccine-induced immune response. The intracellular level of encoded heterologous antigen expression by Lm-RIID vaccines following infection of mouse DC2.4 dendritic cells was measured. As a non-limiting example, the antigen expression level of four independent Lm-RIID strains encoding distinct heterologous was measured. All antigen expression cassette constructs encoded a fusion protein consisting of the amino terminal

TABLE 6

Bacterial strains.

| Strain | Genotype | Parent Strain | Recombinase expr. cassette & locus | Antigen expr. cassette & locus |
|---|---|---|---|---|
| Lm11 | ΔactA, ΔinlB | | none | none |
| BH1959 | ΔactA, ΔinlB, ΔuvrAB | | none | inlB::ActAN100-QuadVac |
| BH1960 | ΔactA, ΔinlB, ΔuvrAB, prfAG155S | | none | inlB::ActAN100-QuadVac |
| BH3141 | ΔactA, ΔinlB, ΔuvrAB, lmo0003-lox71-yaaA | BH1959 | none | inlB::ActAN100-QuadVac |
| BH3210 | ΔactA, ΔinlB, ΔuvrAB, lmo0003-lox71-yaaA, gyrA-lox66-lmo0008 | BH3141 | none | inlB::ActAN100-QuadVac |
| BH3226 | ΔactA, ΔinlB, ΔuvrAB, lmo0003-lox71-yaaA, gyrA-lox66-lmo0008 | BH3210 | tRNA$^{Arg}$::PactA-Cre | inlB::ActAN100-QuadVac |
| BH3099 | ΔactA ΔinlB ΔuvrAB | BH1959 | tRNA$^{Arg}$::PactA-Cre | inlB::ActAN100-QuadVac |
| BH3291 | ΔactA, ΔinlB, gyrA-lox66-lmo0008 | Lm11 | none | none |
| BH3339 | ΔactA, ΔinlB, lmo0003-lox71-yaaA, gyrA-lox66-lmo0008 | BH3291 | none | none |
| BH3618 | ΔactA, ΔinlB, lmo0003-lox71-yaaA, gyrA-lox66-lmo0008 | BH3339 | ΔactA::PactA-Cre | none |
| BH3408 | ΔactA, ΔinlB, lmo2851-lox71-lmo2852 | Lm11 | lmo2851-PactA-Cre-lmo2852 | none |
| BH3410 | ΔactA, ΔinlB, lmo2851-lox71-lmo2852, gyrA-lox66-lmo0008 | BH3291 | lmo2851-PactA-Cre-lmo2852 | none |
| BH3558 | ΔactA, ΔinlB, lmo0003-frt-yaaA | Lm11 | none | none |
| BH3578 | ΔactA, ΔinlB, lmo0003-frt-yaaA, gyrA-frt-lmo0008 | BH3558 | none | none |
| BH3602 | ΔactA, ΔinlB, lmo0003-frt-yaaA, gyrA-frt-lmo0008 | BH3578 | tRNA$^{Arg}$::PactA-FLP | none |
| BH3943 | ΔactA, ΔinlB | Lm11 | none | tRNA$^{Arg}$::ActAN100-NY-ESO-1-MAGE A3 |
| BH3953 | ΔactA, ΔinlB, lmo0003-lox71-yaaA, gyrA-lox66-lmo0008 | BH3816 | ΔactA::PactA-Cre | tRNA$^{Arg}$::ActAN100-NY-ESO-1-MAGE A3 |
| BH3947 | ΔactA, ΔinlB | Lm11 | none | tRNA$^{Arg}$::ActAN100-HBV Polymerase-HBxAg |
| BH3957 | ΔactA, ΔinlB, lmo0003-lox71-yaaA, gyrA-lox66-lmo0008 | BH3816 | ΔactA::PactA-Cre | tRNA$^{Arg}$::ActAN100-HBV Polymerase-HBxAg |
| BH3951 | ΔactA, ΔinlB | Lm11 | none | tRNA$^{Arg}$::ActAN100-PfCSP |
| BH3961 | ΔactA, ΔinlB, lmo0003-lox71-yaaA, gyrA-lox66-lmo0008 | BH3816 | ΔactA::PactA-Cre | tRNA$^{Arg}$::ActAN100-PfCSP |
| BH892 | ΔactA, ΔinlB | Lm11 | none | tRNA$^{Arg}$::ActAN100-OVA |
| BH3709 | ΔactA, ΔinlB, lmo0003-lox71-yaaA, gyrA-lox66-lmo0008 | BH3816 | ΔactA::PactA-Cre | tRNA$^{Arg}$::ActAN100-AH1-OVA |

Example 6

Use as an Antigen Expression Platform

A prerequisite for vaccine potency is delivery of the target antigen in an immunologically relevant context. For Lm-based vaccines, antigens must be expressed and delivered to the host antigen presenting cell (e.g., dendritic cells) cytosol, were encoded antigens are expressed, secreted from the bacterium into the cytosol, where subsequent antigen processing and presentation on MHC class I molecules results in CD8+ T cell priming. It will be appreciated by the skilled 100 amino acids of the *Listeria* ActA protein (ActAN100) cloned the in-frame with the heterologous antigen, as described previously (Lauer et. al., 2008). Detection of intracellular antigen expression was by Western blot analysis of infected cell lysates, using a polyclonal antibody raised against the mature amino terminus of ActA (described in Example 1). Expression of all antigens was functionally linked the actA promoter, which is minimally expressed in broth culture, and induced approximately 200-fold in the host cell cytosol (Shetron-Rama et al., 2002). The actA promoter was also used for Cre or FLP recombinase expression, to link the temporal expression of the vaccine antigen with the intracellular death of the bacterium in the cytosol of the infected host cell of the vaccinated recipient. All antigen expression cassettes were cloned into a derivative of the site-specific integration vector pPL2 and integrated at the tRNA$^{Arg}$ locus of both Lm11 (live-attenuated) and BH3618 (Lm-RIID) strains, as described previously (Lauer et. al., 2008).

Genes for all antigens were codon-optimized for expression in *Listeria* and synthesized de novo (DNA2.0, Menlo Park, Calif.). Fusions were then assembled by PCR and cloning for a fusion of the cancer antigens NY-ESO-1 and MAGE A3 (FIG. 7B), and the infectious disease antigens HBV polymerase and HBxAg (FIG. 7C) or the *Plasmodium falciparum* circumsporozoite protein (PfCSP) (FIG. 7D). Expression was normalized to the *Listeria* P60 protein as described in Example 1. Relative expression from Lm-RIID was calculated as the ratio of expression measured from the Lm-RIID strain divided by the expression from the paired live attenuated control strain. The measured ratio of expression were 1× for NY-ESO-1-MAGE A3, 1.1× for the HBV polymerase-HBxAg fusion, and 1.8× for the Pf-CSP antigen construct. These results demonstrate that concurrently with intracellular bacterial death, Lm-RIID strains expressed robust levels of encoded vaccine antigens and delivered them to the host-cell for processing and the induction of an immune response, significantly at levels that were comparable with that observed with parental recombinant live-attenuated Lm vaccine strains.

Example 7

Clearance of Lm-RIID Vaccine Strains In Vivo

The principal organs that are infected in the mouse following intravenous (IV) administration of *L. monocytogenes* (Lm) are the liver and spleen (Portnoy et al., 2002). The acute toxicity determined by median lethality of the live-attenuated Lm ΔactA/ΔinlB vaccine platform is attenuated by more than 3 logs in the mouse listeriosis model as compared to wild-type Lm (WT Lm), which is reflected by rapid clearance in the liver and spleen in infected mice, measured by quantification of colony forming units (cfu) in cell lysates prepared from harvested organs (Brockstedt et al., 2004).

As shown in the examples contained herein, Lm-RIID can be derived from the live-attenuated Lm ΔactA/ΔinlB (i.e., deletion or mutation of actA and inlB virulence genes) vaccine strain. However, in contrast to Lm ΔactA/ΔinlB, Lm-RIID vaccines are pre-programmed (i.e., engineered) to spontaneously initiate its own suicide within the context of infected cells of the vaccinated mammal. To illustrate the increased safety profile of vaccine strains based on Lm-RIID vaccines compared to Lm ΔactA/ΔinlB vaccines, the kinetics of clearance in both immune competent C57BL/6 mice and in immune deficient SCID-Beige mice lacking functional innate and adaptive immunity were compared. Groups of 5 female C57BL/6 mice were given $5\times10^6$ cfu of Lm-RIID (BH3226) or Lm ΔactA/ΔinlB (BH3099) vaccine strains by IV injection, and the bacterial burden in the livers and spleens were determined by plating on nutrient agar serial dilutions of clarified lysates processed from harvested organs at 0.2, 4 and 24 hours post injection. The amount of Lm ΔactA/ΔinlB (BH3099) vaccine strain measured in the liver or spleen was at similar levels at the 4 and 24 hour time points; i.e., the Lm ΔactA/ΔinlB (BH3099) vaccine strain bacterial burden did not diminish during this period (FIG. 8A). In striking contrast, the quantity of Lm-RIID (BH3226) rapidly decreased at 4 hours post injection as compared to the 0.2 hours post injection time point, and no Lm-RIID (BH3226) colonies could be detected by culture at the final time point evaluated at 24 hours post infection (FIG. 8A).

These results provide unequivocal evidence that Lm-RIID (BH3226) is cleared significantly more rapidly from the livers and spleens of mice following IV administration as compared to live-attenuated Lm ΔactA/ΔinlB (BH3099). To assess the dependence of the host immune response on the clearance of live-attenuated Lm ΔactA/ΔinlB and Lm-RIID vaccine strains, in a separate experiment, groups of 4 female SCID/Beige immune deficient mice were given $5\times10^6$ cfu of Lm-RIID (BH3226) or Lm ΔactA/ΔinlB (BH3099) vaccine strains by IV injection, and the bacterial burden in the spleens were determined by plating on nutrient agar serial dilutions of clarified lysates processed from organs harvested at 20 minutes, 1, 2 and 4 days post injection. The bacterial burden measured in the spleens of SCID/Beige immune mice given live-attenuated Lm ΔactA/ΔinlB (BH3099) increased at 1 day compared to the level measured at 20 minutes after injection, indicating multiplication of the input bacteria. The peak level of bacteria observed at 1 day post injection with Lm ΔactA/ΔinlB (BH3099) was at least $5\times10^6$ cfu per spleen, and then decreased over the next 2 time points evaluated to a level of about $5\times10^4$ cfu per spleen measured at the last 4 day post injection time point evaluated (FIG. 8B). In striking contrast, no multiplication of bacteria, as determined by an increase in cfu between time points, could be measured in the spleens of SCID/Beige immune mice given Lm-RIID (BH3226) vaccine strain; the bacterial burden rapidly declined following the first time point evaluated at 20 minutes post injection, and by the 4 day post injection time point, no Lm-RIID (BH3226) colonies could be detected in the spleens (FIG. 8B). Taken together, the results shown in FIGS. 8A and 8B demonstrate that Lm-RIID vaccine strains spontaneously initiate its own clearance from the vaccinated host, and, essentially, a functioning immune response is not required for clearance. The skilled artisan will recognize that this characteristic of spontaneous clearance is a desirable feature for broad application of Lm-RIID based strains for both prophylactic and therapeutic vaccines.

Example 8

Immunogenicity of Lm-RIID Strains

Recombinant *L. monocytogenes* has been shown to induce potent CD4+ and CD8+ T cell immunity to encoded heterologous antigens in mice and in humans (Brockstedt et al., 2004; Le et al., 2012). The immunogenicity of Lm-RIID in mice was compared to live-attenuated Lm ΔactA/ΔinlB and Killed But Metabolically Active (KBMA; Lm ΔactA/ΔinlB/ΔuvrAB) was compared. To enable the immunogenicity of the Lm-RIID, Lm ΔactA/ΔinlB, and KBMA vaccines to be compared, each vaccine strain contained the same Ag expression cassette encoding five defined $H-2^b$-restricted major histocompatibility complex (MHC) class I epitopes that have previously been shown to elicit a range of CD8+ T-cell responses in mice, when encoded by live-attenuated Lm ΔactA/ΔinlB, and KBMA vaccines (Lauer et al., 2008). The use of an array of precise class I restricted epitopes provides an optimized method for assessing immunogenicity in vivo, simplifying comparisons of the Lm-RIID, Lm ΔactA/ΔinlB, and KBMA vaccine platforms.

The Ag expression cassette construct encodes four tandemly spaced vaccinia virus (A42R, C4L, K3L, and B8R)

class I epitopes and the chicken OVA (SL8) epitope, and was synthesized and then cloned under the control of the PrfA-regulated actA promoter as a fusion protein with the 100 N-terminal amino acids of ActA (Lauer et al., 2008). The construct is known as Quadvac and was cloned into a derivative of the pPL2 integration vector and then integrated into the tRNA$^{Arg}$ site of Lm-RIID, Lm ΔactA/ΔinlB, and KBMA vaccine strains as described previously (Lauer et al., 2002; Lauer et al., 2008).

Figure 9:
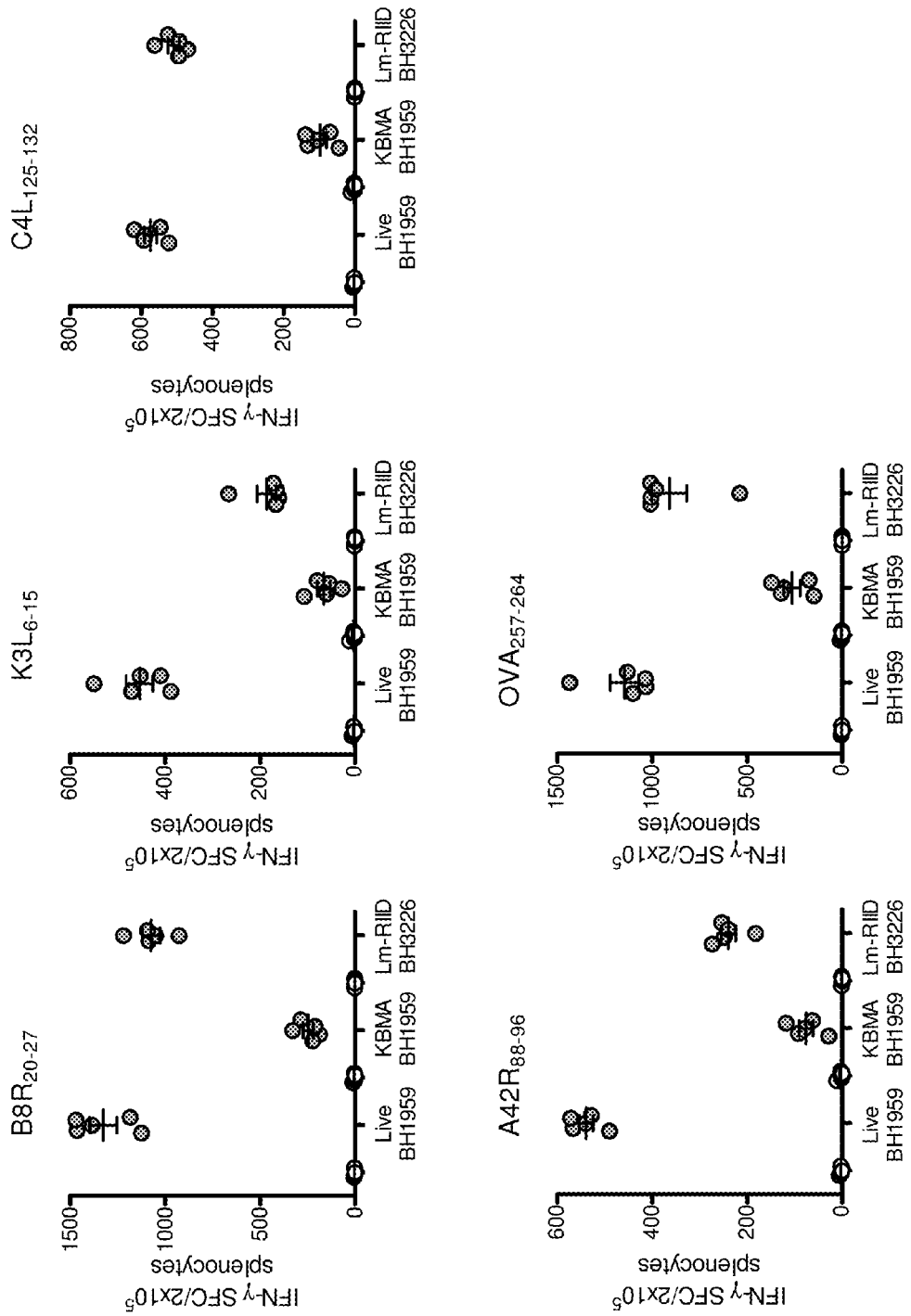
FIG. 9. Immunogenicity of Lm-RIID strains. Open circles: unstimulated; gray: stimulated with peptide noted above.

To evaluate relative immunogenicity, groups of 5 female C57BL/6 (H-2$^b$) mice were immunized twice at an interval of 36 days with the Lm-RIID, Lm ΔactA/ΔinlB, and KBMA vaccine strains each encoding Quadvac, at a dose level of $5 \times 10^6$ colony forming units (CFU). The KBMA vaccine dose level was measured prior to photochemical inactivation, as described previously (Brockstedt et al., 2005). Five days following the second immunization, spleens were harvested from vaccinated mice, and the magnitude of the CD8+T cell responses specific for the 5 encoded epitopes was measured by ELISpot analysis of splenocytes following overnight stimulation with 1 µM of peptides corresponding to each of the MHC class I epitopes having the amino acid sequence as follows, as described previously: A42R$_{88-96}$, YAPVSPIVI (SEQ ID NO: 52); C4L$_{125-132}$, LNFRFENV (SEQ ID NO: 53); K3L$_{6-15}$, YSLPNAGDVI (SEQ ID NO: 54); B8R$_{20-27}$, TSYKFESV (SEQ ID NO: 55); and, SL8$_{257-264}$, SIINFEKL (SEQ ID NO: 56) (Lauer et al., 2008; Moutaftsi et al., 2006). Lm-RIID vaccines induced CD8+T cell responses specific for the 5 MHC class I epitopes that were comparable in magnitude to mice immunized with live-attenuated Lm ΔactA/ΔinlB vaccine strains, and that were significantly higher than the magnitude of the CD8+T cell responses measured in mice immunized with KBMA vaccines (FIG. 9).

These results demonstrate that although Lm-RIID vaccines are engineered initiate a program to commit suicide within infected cells of the vaccinated recipient and do not require a functional immune response for clearance, surprisingly, Lm-RIID vaccines retain the capacity to induce a robust specific CD8 T cell response that is comparable to live-attenuated Lm vaccines. The skilled artisan will understand that these results demonstrate that Lm-RIID vaccines have general utility for preventative or therapeutic vaccination in humans to induce a T cell response specific for desired Ags, due to the characteristics of having similar immunologic potency to live-attenuated Lm vaccines, but having a significantly improved safety profile due to its feature of immune-response independent spontaneous clearance.

Example 9

Protective Immunity Afforded by Vaccination with Lm-RIID Based Vaccine Strains

The Examples provided herein demonstrate that Lm-RIID vaccines self-initiate a pre-programmed suicide within the host cell, do not require a functioning immune response for clearance from the vaccinated host, yet retain the capacity to induce cellular immunity specific for an encoded antigen that is comparable to vaccination with live-attenuated Lm ΔactA/ΔinlB vaccine strains. However, the skilled artisan will recognize that one important measure of effective immunization is whether a vaccine candidate can confer protection against subsequent challenge with a virulent pathogen.

It is well-recognized in the field that a single immunization of mice with sub-lethal doses of wild-type Lm (WT Lm) or appropriate live-attenuated strains affords life-long protection against lethal challenge with WT Lm, measured by bacterial burden in the liver or spleen at three days post challenge (Bahjat et al., 2006). The correlates of protection are CD4+ and CD8+ T cell immunity, and humoral immunity plays no role in protection (Berche et al., 1987). To evaluate the relative capacity of Lm-RIID vaccination to provide protective immunity, groups of 5 female C57BL/6 mice were vaccinated with Hanks-balanced salt solution (HBSS) as a negative control, or with $5 \times 10^6$ cfu of Lm-RIID or live-attenuated Lm ΔactA/ΔinlB vaccines, or with $1 \times 10^8$ cfu (determined prior to photochemical inactivation) of KBMA vaccines. Vaccinated and control mice were challenged at 41 days post vaccination in order to assess the capacity of the vaccine-induced memory T cell response to provide protection against lethal bacterial challenge with 20 LD$_{50}$ doses ($2 \times 10^5$ cfu) of WT Lm.

Figure 10:
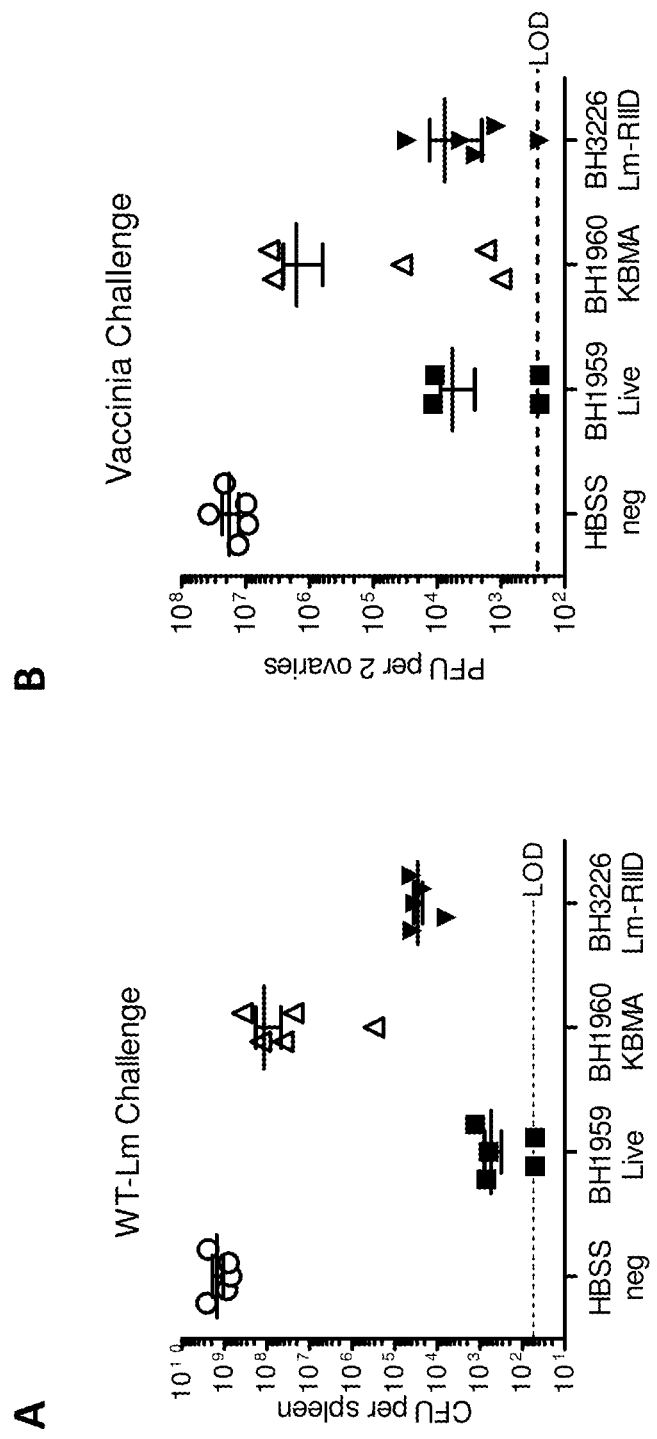
FIG. 10. Protective immunity to heterologous challenge. (A) Protection from WT-Lm challenge with live attenuated, KBMA, and Lm-RIID strains. (B) Protection from a heterologous challenge with WT vaccinia virus with live-attenuated, KBMA, and Lm-RIID strains.
Figure 11:
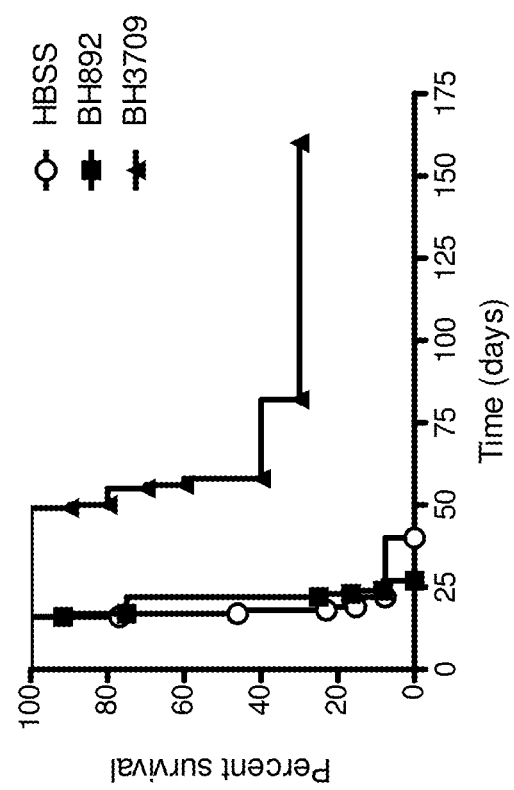
FIG. 11. Therapeutic efficacy of Lm-RIID vaccines in a CT-26 tumor model.

Vaccination with Lm-RIID provided 4 logs of protection against WT Lm challenge as compared to the HBSS negative control group (FIG. 10A). While the level of protection afforded by Lm-RIID was approximately 20-fold less than vaccination with Lm ΔactA/ΔinlB, it was more than 3 logs better compared to vaccination with KBMA vaccines (FIG. 10A). As a second measure to assess the functional capacity of Lm-RIID vaccine-induced T cell responses to afford protection against pathogen challenge, we utilized the vaccinia virus challenge model. With this model, protection is measured by quantitating challenge virus in the ovaries of mice by plaque assay 5 days following challenge with vaccinia virus encoding an antigen that is cognate to the test vaccine used for immunization (Belyakov et al., 1998; Brockstedt et al., 2005). To assess protective immunity, mice were vaccinated twice with an interval of 29 days with $5 \times 10^6$ cfu of Lm-RIID or live-attenuated Lm ΔactA/ΔinlB vaccines, or with $1 \times 10^8$ cfu (determined prior to photochemical inactivation) of KBMA vaccines. All test vaccines encoded the Quadvac vaccinia virus CD8+ T cell epitopes and SL8 CD8+ T cell epitope described in Example 9. 49 days following the boost vaccination, mice were challenged by intraperitoneal challenge with $1 \times 10^6$ plaque forming units (pfu) with vaccinia virus encoding chicken Ovalbumin, and pfu in the ovaries was measured 4 days later by plaque assay on BSC cells of serial dilutions of clarified processed organ homogenates.

Strikingly, the level of protection afforded by immunization with Lm-RIID or live-attenuated Lm ΔactA/ΔinlB vaccines was indistinguishable, and was greater than 1000-fold compared to the HBSS negative control group, and was more than 100-fold better than the level of protection afforded by vaccination with KBMA vaccines (FIG. 10B). The skilled artisan will readily recognize that the Lm-RIID vaccines have a desirable safety profile compared to live-attenuated Lm ΔactA/ΔinlB vaccines, yet provide comparable immunologic potency, as measured by the extent of protection against pathogen challenge.

Example 10

Lm-RIID Vaccine Induced Therapeutic Anti-Tumor Efficacy

Having demonstrated that Lm-RIID vaccines stimulate CD4+ and CD8+ T cell immunity specific for vector encoded antigens which function to provide protection against challenge with a pathogen encoding the cognate antigen, that is comparable to live-attenuated Lm ΔactA/ ΔinlB vaccine strains, the skilled artisan will recognize that Lm-RIID vaccines will also have application for cancer immunotherapy. It is well-appreciated that barriers to effective immune therapies include tolerance to the targeted tumor-associated antigen(s) that can limit induction of cytotoxic CD8+ T cells of appropriate magnitude and function, poor trafficking of the generated T cells to sites of malignant cells, and poor persistence of the induced T cell response (Blankenstein et al., 2012; Topalian et al., 2011). One measure of potency is to evaluate the capacity of a selected platform to reverse tumor progression and increase survival time compared to controls, when administered to tumor-bearing animals.

The CT-26 murine colon tumor cell line was used to test the benefit of therapeutic vaccination with Lm-RIID vaccines (Slansky et al., 2000). The CT-26 tumor cells were given by intravenous (IV) inoculation, which results in the establishment of lung tumor nodules that can be quantitated in the lungs harvested from treated mice at desired time points post implantation, or, alternatively, mice can be monitored for survival, and sacrificed when moribund, due to excessive tumor growth preventing adequate respiration. Therapeutic efficacy in the CT26 tumor model requires breaking of self-tolerance to the H-2$L^d$-restricted immunodominant epitope AH1 from the gp70 endogenous tumor antigen (Slansky et al., 2000). Lm-RIID vaccines were constructed that expressed the altered peptide ligand AH1-A5 epitope (SPSYAYHQF (SEQ ID NO: 57)), containing a heteroclitic valine to alanine change in the fifth position of the MHC class I epitope, embedded in-frame within a unique Ava II restriction endonuclease site in chicken ovalbumin (OVA), as described previously (Brockstedt et al., 2004). To evaluate the therapeutic efficacy of Lm-RIID, 30 Female BALB/c mice were each given $2\times10^5$ CT26 cells suspended in 100 μl of HBSS by tail vein injection, and then randomized to 3 groups of 10 mice. 4 days later, the 3 groups of mice were given 100μl of HBSS, or $5\times10^6$ cfu of live-attenuated Lm ΔactA/ΔinlB expressing OVA (BH892), or $5\times10^6$ cfu of Lm RIID expressing OVA-AH1-A5 (BH3709). Fourteen days later, the same injections were given to all 3 groups of mice, and all mice were then monitored daily for survival.

Tumor-bearing animals in negative controls groups treated with HBSS or live-attenuated Lm ΔactA/ΔinlB expressing OVA had a median survival time of about 24 days post CT-26 tumor cell implantation (FIG. 11). In striking contrast, the group of mice given Lm RIID expressing OVA-AH1-A5 had a median survival time of 55 days, that was significantly longer than either control group ($p<0.001$, log-rank Mantel-Cox test) (FIG. 11). Furthermore, 30% of the animals treated with Lm-RIID vaccines expressing OVA-AH1-A5 were long-term survivors, when the experiment was terminated 160 days following tumor cell implantation (FIG. 11). These results provide unequivocal evidence that Lm-RIID vaccines although pre-programmed to commit suicide within host cells of the vaccinated recipient, retain the capacity to initiate a functional tumor-specific CD8+ T cell response in tumor-bearing animals, and provide significant benefit and overall survival, as compared to negative controls. The skilled artisan will recognize that Lm-RIID vaccines are a platform with direct application to clinical cancer immunotherapy, due to the combined properties of safety and therapeutic efficacy.

Example 11

REFERENCES

1. Albert, H., Dale, E. C., Lee, E., and Ow, D. W. (1995). Site-specific integration of DNA into wild-type and mutant lox sites placed in the plant genome. The Plant Journal: For Cell And Molecular Biology 7, 649-659.

2. Bahjat, K. S., Liu, W., Lemmens, E. E., Schoenberger, S. P., Portnoy, D. A., Dubensky, T. W., Jr., and Brockstedt, D. G. (2006). Cytosolic entry controls CD8+-T-cell potency during bacterial infection. Infect Immun 74, 6387-6397.

3. Belyakov, I. M., Ahlers, J. D., Brandwein, B. Y., Earl, P., Kelsall, B. L., Moss, B., Strober, W., and Berzofsky, J. A. (1998). The importance of local mucosal HIV-specific CD8 (+) cytotoxic T lymphocytes for resistance to mucosal viral transmission in mice and enhancement of resistance by local administration of IL-12. J Clin Invest 102, 2072-2081.

4. Berche, P., Gaillard, J. L., and Sansonetti, P. J. (1987). Intracellular growth of *Listeria monocytogenes* as a prerequisite for in vivo induction of T cell-mediated immunity. J Immunol 138, 2266-2271.

5. Bishop, D. K., and Hinrichs, D. J. (1987). Adoptive transfer of immunity to *Listeria monocytogenes*. The influence of in vitro stimulation on lymphocyte subset requirements. J Immunol 139, 2005-2009.

6. Blankenstein, T., Coulie, P. G., Gilboa, E., and Jaffee, E. M. (2012). The determinants of tumour immunogenicity. Nature reviews. Cancer 12, 307-313.

7. Brockstedt, D. G., Bahjat, K. S., Giedlin, M. A., Liu, W., Leong, M., Luckett, W., Gao, Y., Schnupf, P., Kapadia, D., Castro, G., et al. (2005). Killed but metabolically active microbes: a new vaccine paradigm for eliciting effector T-cell responses and protective immunity. Nat Med 11, 853-860.

8. Brockstedt, D. G., Giedlin, M. A., Leong, M. L., Bahjat, K. S., Gao, Y., Luckett, W., Liu, W., Cook, D. N., Portnoy, D. A., and Dubensky, T. W., Jr. (2004). *Listeria*-based cancer vaccines that segregate immunogenicity from toxicity. Proc Natl Acad Sci USA 101, 13832-13837.

9. Camilli, A., Tilney, L. G., and Portnoy, D. A. (1993). Dual roles of plcA in *Listeria monocytogenes* pathogenesis. Mol Microbiol 8, 143-157.

10. Horton, R. M. (1993). In Vitro Recombination and Mutagenesis of DNA: SOEing Together Tailor-Made Genes. Methods Mol Biol 15, 251-261.

11. Lauer, P., Chow, M. Y., Loessner, M. J., Portnoy, D. A., and Calendar, R. (2002). Construction, characterization, and use of two *Listeria monocytogenes* site-specific phage integration vectors. J Bacteriol 184, 4177-4186.

12. Lauer, P., Hanson, B., Lemmens, E. E., Liu, W., Luckett, W. S., Leong, M. L., Allen, H. E., Skoble, J., Bahjat, K. S., Freitag, N. E., et al. (2008). Constitutive Activation of the PrfA regulon enhances the potency of vaccines based on live-attenuated and killed but metabolically active *Listeria monocytogenes* strains. Infect Immun 76, 3742-3753.

13. Le, D. T., Brockstedt, D. G., Nir-Paz, R., Hampl, J., Mathur, S., Nemunaitis, J., Sterman, D. H., Hassan, R., Lutz, E., Moyer, B., et al. (2012). A live-attenuated *Listeria* vaccine (ANZ-100) and a live-attenuated *Listeria* vaccine expressing mesothelin (CRS-207) for advanced cancers: phase I studies of safety and immune induction. Clin Cancer Res 18, 858-868.

14. Moutaftsi, M., Peters, B., Pasquetto, V., Tscharke, D. C., Sidney, J., Bui, H. H., Grey, H., and Sette, A. (2006). A consensus epitope prediction approach identifies the breadth of murine T(CD8+)-cell responses to vaccinia virus. Nat Biotechnol 24, 817-819.

15. Portnoy, D. A., Auerbuch, V., and Glomski, I. J. (2002). The cell biology of *Listeria monocytogenes* infection: the intersection of bacterial pathogenesis and cell-mediated immunity. J Cell Biol 158, 409-414.

16. Portnoy, D. A., Jacks, P. S., and Hinrichs, D. J. (1988). Role of hemolysin for the intracellular growth of *Listeria monocytogenes*. J Exp Med 167, 1459-1471.

17. Shen, Z., Reznikoff, G., Dranoff, G., and Rock, K. L. (1997). Cloned dendritic cells can present exogenous antigens on both MHC class I and class II molecules. J Immunol 158, 2723-2730.

18. Shetron-Rama, L. M., Marquis, H., Bouwer, H. G., and Freitag, N. E. (2002). Intracellular induction of *Listeria monocytogenes* actA expression. Infect Immun 70, 1087-1096.

19. Simon, R., Priefer, U., and Pulhler, A. (1983). A broad host range mobilization system for in vivo genetic engineering: transposon mutagenesis in gram negative bacteria. Nature Biotech 1, 784-791.

20. Slansky, J. E., Rattis, F. M., Boyd, L. F., Fahmy, T., Jaffee, E. M., Schneck, J. P., Margulies, D. H., and Pardoll, D. M. (2000). Enhanced antigen-specific antitumor immunity with altered peptide ligands that stabilize the MHC-peptide-TCR complex. Immunity 13, 529-538.

21. Smith, K., and Youngman, P. (1992). Use of a new integrational vector to investigate compartment-specific expression of the *Bacillus subtilis* spoIIM gene. Biochimie 74, 705-711.

22. Topalian, S. L., Weiner, G. J., and Pardoll, D. M. (2011). Cancer immunotherapy comes of age. Journal of clinical oncology: official journal of the American Society of Clinical Oncology 29, 4828-4836.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

---

We claim:

1. A method for configuring a bacterium to delete one or more genes in the bacterial genome which are essential for multiplication of the bacterium, the deletion occurring preferentially when the bacterium is introduced into a mammalian host, comprising:
   (i) introducing into the bacterium a nucleic acid encoding a recombinase heterologous to the bacterium operably connected to regulatory sequences which preferentially induce expression of the recombinase in the mammalian host, and
   (ii) introducing in the bacterial genome a first attachment site for the recombinase upstream from the gene(s) essential for multiplication of the bacterium, and a second attachment site for the recombinase downstream from the gene(s) essential for multiplication of the bacterium, such that the recombinase, when expressed in the mammalian host, catalyzes a site specific recombination event which deletes the gene(s) essential for multiplication of the bacterium flanked by the first and second attachment sites, wherein the bacterium is deficient for multiplication following the site specific recombination event.

2. A method according to claim 1, wherein the bacterium is an intracellular pathogen, and the regulatory sequences preferentially induce expression of the recombinase when the bacterium is in a mammalian host cell, and is most preferably a facultative intracellular bacterium.

3. A method according to claim 1, wherein the bacterium is of a genus selected from the group consisting of *Listeria, Neisseria, Mycobacterium, Francisella, Bacillus, Salmonella, Shigella, Yersinia, Brucella, Legionella, Rickettsia,* and *Chlamydia.*

4. A method according to claim 1, wherein the bacterium is *Listeria monocytogenes.*

5. A method according to claim 4, wherein the bacterium is *Listeria monocytogenes.*, wherein the *Listeria monocytogenes* is ΔActA/ΔInlB.

6. A method according to claim 4, wherein the regulatory sequences comprise a *Listeria monocytogenes* promoter which is PrfA-dependent.

7. A method according to claim 6, wherein PrfA-dependent promoter is selected from the group consisting of the inlA promoter, the inlB promoter, the inlC promoter, the hpt promoter, the hly promoter, the plcA promoter, the mpl promoter, and the actA promoter.

8. A method according to claim 6, wherein the PrfA-dependent promoter is an actA promoter.

9. A method according to claim 1, wherein the recombinase is selected from the group consisting of φC31 integrase, R4 integrase, TP901 integrase, φBT1 integrase, BxB1 integrase, PSA integrase, Cre recombinase, Flp recombinase, XerC recombinase, λ integrase, HK022 integrase, P22 integrase, HP1 integrase, L5 integrase, γδ recombinase, Tn3 recombinase, gin recombinase, RV integrase, SPBc integrase, TG1 integrase, φC1 integrase, MR11 integrase, φ370 integrase, φK38 integrase, Wβ integrase, and BL3 integrase.

10. A method according to claim 1, wherein the first attachment site is an attB site and the second attachment site is an attP site.

11. A method according to claim 1, wherein the one or more genes essential for multiplication of the bacterium comprise at least one gene involved in DNA replication.

12. A method according to claim 11, wherein the at least one gene involved in DNA replication is selected from the group consisting of ori, dnaA, dnaN, gyrA, gyrB, polC, dnaE, ftsK, ftsZ, ligA, dnaG, parC, parE, holB, dnaX, SMC, and ftsY.

13. A method according to claim 1, wherein the one or more genes essential for multiplication of the bacterium are part of an operon, and the first attachment site is upstream of all or a portion of the operon, and the second attachment site is downstream of all or a portion of the operon.

14. A method according to claim 13, wherein the first attachment site is upstream of all of the operon, and the second attachment site is downstream of all of the operon.

15. A method according to claim 1, wherein the recombinase is a Cre recombinase, the regulatory sequences comprise an actA promoter, the first and second attachment sites comprise loxP sites, and the gene(s) essential for multiplication of the bacterium flanked by the first and second attachment sites are involved in DNA replication.

16. A method according to claim 1, wherein the first and second attachment sites flank a nucleic acid sequence about 20 kb in length or less.

17. A method according to claim 16, wherein the nucleic acid sequence is about 10 kb in length or less.

18. A method according to claim 16, wherein the nucleic acid sequence is about 6 kb in length.

19. A method according to claim 1, wherein the bacterium comprises within the bacterial genome an exogenous nucleic acid sequence encoding a heterologous polypeptide, wherein the exogenous nucleic acid sequence is operably connected to regulatory sequences which preferentially induce expression of the heterologous polypeptide when the bacterium is in a mammalian host.

20. A method according to claim 1, further comprising:
   introducing the bacterium according to claim 1 to a mammalian host under conditions wherein the recombinase is expressed by the bacterium, and wherein the expressed recombinase deletes the one or more genes essential for multiplication of the bacterium by the site specific recombination event.

21. A method according to claim 20, wherein the bacterium comprises within the bacterial genome an exogenous nucleic acid sequence encoding a heterologous polypeptide, wherein the exogenous nucleic acid sequence is operably connected to regulatory sequences which preferentially induce expression of the heterologous polypeptide when the bacterium is in the mammalian host, and wherein the bacterium expresses the heterologous polypeptide within the mammalian host.

* * * * *